(12) United States Patent
Schulze et al.

(10) Patent No.: US 7,511,059 B2
(45) Date of Patent: Mar. 31, 2009

(54) THIAZOLIDINONES, THEIR PRODUCTION AND USE AS PHARMACEUTICAL AGENTS

(75) Inventors: Volker Schulze, Berlin (DE); Knut Eis, Berlin (DE); Lars Wortmann, Berlin (DE); Dirk Kosemund, Erfurt (DE); Olaf Prien, Berlin (DE); Gerhard Siemeister, Berlin (DE); Holger Hess-Stumpp, Berlin (DE); Uwe Eberspaecher, Berlin (DE); Damian O Arnaiz, El Sobrante, CA (US)

(73) Assignee: Schering Ag, Berlin (DE)

( * ) Notice: Subject to any disclaimer, the term of this patent is extended or adjusted under 35 U.S.C. 154(b) by 4 days.

(21) Appl. No.: 11/345,666

(22) Filed: Feb. 2, 2006

(65) Prior Publication Data

US 2006/0223833 A1  Oct. 5, 2006

Related U.S. Application Data

(60) Provisional application No. 60/651,232, filed on Feb. 10, 2005.

(30) Foreign Application Priority Data

Feb. 3, 2005  (DE)  ........................ 10 2005 005 395

(51) Int. Cl.
C07D 417/06 (2006.01)
C07D 417/14 (2006.01)
A61K 31/422 (2006.01)
A61K 31/423 (2006.01)
A61K 31/427 (2006.01)
A61K 31/4439 (2006.01)

(52) U.S. Cl. ........................ 514/307; 514/342; 514/364; 514/369; 546/145; 546/269.7; 548/131; 548/147; 548/181; 548/186; 548/187

(58) Field of Classification Search ................. 546/145, 546/269.7; 548/131, 147, 181, 186, 187; 514/307, 342, 364, 369

See application file for complete search history.

(56) References Cited

U.S. PATENT DOCUMENTS

| 2006/0079503 | A1 | 4/2006 | Schering | |
| 2007/0010565 | A1* | 1/2007 | Prien et al. | 514/369 |
| 2007/0010566 | A1* | 1/2007 | Prien et al. | 514/369 |
| 2007/0015759 | A1* | 1/2007 | Schulze et al. | 514/242 |
| 2007/0037862 | A1* | 2/2007 | Siemeister et al. | 514/369 |

FOREIGN PATENT DOCUMENTS

| WO | WO 03/093249 A1 | 11/2003 |
| WO | WO 2004/043936 A1 | 5/2004 |
| WO | WO 2005/042505 A1 | 5/2005 |

* cited by examiner

*Primary Examiner*—Fiona T Powers
(74) *Attorney, Agent, or Firm*—Millen, White, Zelano & Branigan, P.C.

(57) ABSTRACT

The invention relates to thiazolidinones of general formula (I)

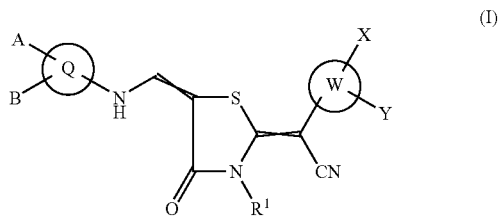

their production and use as inhibitors of polo-like kinases (Plk) for treating various diseases.

15 Claims, No Drawings

THIAZOLIDINONES, THEIR PRODUCTION AND USE AS PHARMACEUTICAL AGENTS

This application claims the benefit of the filing date of U.S. Provisional Application Ser. No. 60/651,232 filed Feb. 10, 2005, which is incorporated by reference herein.

The invention relates to thiazolidinones, their production and use as inhibitors of polo-like kinases (Plk) for treating various diseases.

Tumor cells are distinguished by an uninhibited cell-cycle process. On the one hand, this is based on the loss of control proteins, such as RB, p16, p21, p53, etc., as well as the activation of so-called accelerators of the cell-cycle process, the cyclin-dependent kinases (Cdks). The Cdks are an antitumor target protein that is acknowledged in pharmaceutics. In addition to the Cdks, serine/threonine kinases that regulate the new cell cycle, so-called 'polo-like kinases,' were described, which are involved not only in the regulation of the cell cycle but also in the coordination with other processes during mitosis and cytokinesis (formation of the spindle apparatus, chromosome separation). This class of proteins therefore represents an advantageous point of application for therapeutic intervention of proliferative diseases such as cancer (Descombes and Nigg. Embo J, 17; 1328 ff, 1998; Glover et al. Genes Dev 12, 3777 ff, 1998).

A high expression rate of Plk-1 was found in 'non-small cell lung' cancer (Wolf et al. Oncogene, 14, 543ff, 1997), in melanomas (Strebhardt et al. JAMA, 283, 479ff, 2000), in 'squamous cell carcinomas' (Knecht et al. Cancer Res, 59, 2794ff, 1999) and in 'esophageal carcinomas' (Tokumitsu et al. Int J Oncol 15, 687ff, 1999).

A correlation of a high expression rate in tumor patients with poor prognosis was shown for the most varied tumors (Strebhardt et al. JAMA, 283, 479ff, 2000, Knecht et al. Cancer Res, 59, 2794ff, 1999 and Tokumitsu et al. Int J Oncol 15, 687ff, 1999).

The constitutive expression of Plk-1 in NIH-3T3 cells resulted in a malignant transformation (increased proliferation, growth in soft agar, colony formation and tumor development in hairless mice ) (Smith et al. Biochem Biophys Res Comm, 234, 397ff., 1997).

Microinjections of Plk-1 antibodies in HeLa cells resulted in improper mitosis (Lane et al.; Journal Cell Biol, 135, 1701ff, 1996).

With a '20-mer' antisense oligo, it was possible to inhibit the expression of Plk-1 in A549 cells, and to stop their ability to survive. It was also possible to show a significant anti-tumor action in hairless mice (Mundt et al., Biochem Biophys Res Comm, 269, 377ff., 2000).

The microinjection of anti-Plk antibodies in non-immortalized human Hs68 cells showed, in comparison to HeLa cells, a significantly higher fraction of cells, which remained in a growth arrest at G2 and showed far fewer signs of improper mitosis (Lane et al.; Journal Cell Biol, 135, 1701ff, 1996).

In contrast to tumor cells, antisense-oligo-molecules did not. inhibit the growth and the viability of primary human mesangial cells (Mundt et al., Biochem Biophys Res Comm, 269, 377ff., 2000).

In mammals, to date in addition to the Plk-1, three other polo-kinases were described that are induced as a mitogenic response and exert their function in the GI phase of the cell cycle. These are, on the one hand, the so-called Prk/Plk-3 (the human homolog of the mouse-Fnk=fibroblast growth factor-induced kinase; Wiest et al, Genes, Chromosomes & Cancer, 32: 384ff, 2001), Snk/Plk-2 (Serum-Induced Kinase, Liby et al., DNA Sequence, 11, 527-33, 2001) and sak/Plk4 (Fode et al., Proc. Natl. Acad. Sci. U.S.A., 91, 6388ff; 1994).

The inhibition of Plk-1 and the other kinases of the polo family, such as Plk-2, Plk-3 and Plk-4, thus represents a promising approach for the treatment of various diseases.

The sequence identity within the Plk domains of the polo family is between 40 and 60%, so that partial interaction of inhibitors of a kinase occurs with one or more other kinases of this family. Depending on the structure of the inhibitor, however, the action can also take place selectively or preferably on only one kinase of the polo family.

In International Application WO03/093249, thiazolidinone compounds that inhibit the kinases of the polo family are disclosed.

The properties of the compounds of the prior art are always in need of improvement, however.

An object of this invention is thus to provide compounds that are improved, compared to the prior art, in particular improved in the inhibition of polo-like kinases and/or cell proliferation, and/or to make available alternative compounds that inhibit kinases, in particular polo-like kinases and/or the cell proliferation.

It has now been found, surprisingly enough, that compounds of general formula I

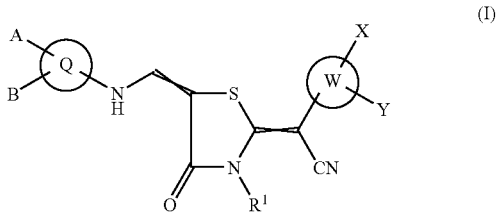

in which
Q stands for aryl or heteroaryl,
A and B, independently of one another, stand for hydrogen, halogen, hydroxy, amino or nitro, or
for $C_1$-$C_6$-alkyl or $C_1$-$C_6$-alkoxy that optionally is substituted in one or more places, in the same way or differently, with halogen, hydroxy, $C_2$-$C_9$-heterocycloalkyl or with the group —$NR^3R^4$ or —$CO(NR^3)$-M, whereby the heterocycloalkyl in the ring contains at least one atom, which is the same or different, from the following group of nitrogen, oxygen or sulfur and optionally can be interrupted by one or more —(CO)— or —$SO_2$— groups in the ring, and optionally one or more double bonds can be contained in the ring, and the ring itself optionally can be substituted in one or more places, in the same way or differently, with cyano, halogen or with $C_1$-$C_6$-alkyl, $C_3$-$C_6$-cycloalkyl, or $C_1$-$C_6$-hydroxyalkyl that is substituted in one or more places, in the same way or differently, with halogen, or with the group —$COR^2$ or —$NR^3R^4$, or
for —$NR^3R^4$, —$NR^3$ (CO)-L, —$NR^3(CO)$—$NR^3$-L, —$COR^2$, —$CO(NR^3)$-M, —$NR^3(CS)NR^3R^4$, —$NR^3SO_2$-L, —$SO_2$—$NR^3R^4$ or —$SO_2(NR^3)$-M,
L stands for $C_1$-$C_6$-atkyl or heteroaryl that optionally is substituted in one or more places, in the same way or differently, with hydroxy, $C_1$-$C_6$-hydroxyalkoxy, $C_1$-$C_6$-alkoxyalkoxy, $C_2$-$C_6$-heterocycloalkyl or with the group —$NR^3R^4$, whereby the heterocycloalkyl in the ring contains at least one atom, which is the same or different, from the following group of nitrogen, oxygen or sulfur and optionally can be interrupted by one or more —(CO)— or —SO$_2$— groups in the ring, and optionally one or more double bonds can be contained in the ring, and the ring itself optionally can be substituted in one or more places, in the same way or differently, with cyano, halogen, or with C$_1$-C$_6$-alkyl, C$_3$-C$_6$-cycloalkyl, or C$_1$-C$_6$-hydroxyalkyl that is substituted in one or more places, in the same way or differently, with halogen, or with the group —COR$^2$ or —NR$^3$R$^4$, M stands for C$_1$-C$_6$-alkyl that optionally is substituted in one or more places, in the same way or differently, with the group —NR$^3$R$^4$ or C$_2$-C$_6$-heterocycloalkyl, whereby the heterocycloalkyl in the ring contains at least one atom, which is the same or different, from the following group of nitrogen, oxygen or sulfur and optionally can be interrupted by one or more —(CO)— or —SO$_2$— groups in the ring, and optionally one or more double bonds can be contained in the ring, and the ring itself optionally can be substituted in one or more places, in the same way or differently, with cyano, halogen or with C$_1$-C$_6$-alkyl, C$_3$-C$_6$-cycloalkyl, or C$_1$-C$_6$-hydroxyalkyl that can be substituted in one or more places, in the same way or differently, with halogen, or with the group —COR$^2$ or —NR$^3$R$^4$, W stands for heteroaryl or C$_2$-C$_9$-heterocycloalkyl, whereby the heterocycloalkyl in the ring contains at least one atom, which is the same or different, from the following group of nitrogen, oxygen or sulfur and optionally can be interrupted by one or more —(CO)— or —SO$_2$— groups in the ring, and optionally one or more double bonds can be contained in the ring, X and Y, independently of one another, stand for hydrogen or C$_1$-C$_6$-alkyl or aryl that optionally is substituted in one or more places, in the same way or differently, with halogen, hydroxy, C$_1$-C$_6$-alkoxy, C$_1$-C$_6$-alkylthio or aryl, or for the group —COOR$^5$ or —CONR$^3$R, or X and Y together are formed by the same atom or by adjacent atoms of W from a C$_3$-C$_6$-cycloalkyl ring or a C$_2$-C$_6$-heterocycloalkyl ring, whereby the heterocycloalkyl in the ring contains at least one atom, which is the same or different, from the following group of nitrogen, oxygen or sulfur and optionally can be interrupted by one or more —(CO)— or —SO$_2$— groups in the ring, and optionally one or more double bonds can be contained in the ring, and the ring itself optionally can be substituted in one or more places, in the same way or differently, with C$_1$-C$_6$-alkyl, C$_3$-C$_6$-cycloalkyl, C$_1$-C$_6$-hydroxyalkyl or with the group —NR$^3$R$^4$, R$^1$ stands for C$_1$-C$_4$-alkyl, C$_3$-cycloalkyl, allyl or propargyl that optionally is substituted in one or more places, in the same way or differently, with cyano or halogen, R$^2$ stands for hydroxy, C$_1$-C$_6$-alkyl, C$_1$-C$_6$-alkoxy or for the group —NR$^3$R$^4$, R$^3$ and R$^4$, independently of one another, stand for hydrogen or for C$_1$-C$_6$-alkyl, C$_1$-C$_6$-alkoxy, —CO—C$_1$-C$_6$-alkyl or aryl that optionally is substituted in one or more places, in the same way or differently, with halogen, hydroxy, C$_2$-C$_6$-heterocycloalkyl, C$_1$-C$_6$-hydroxyalkoxy or with the group —NR$^3$R$^4$, whereby the heterocycloalkyl in the ring contains at least one atom, which is the same or different, from the following group of nitrogen, oxygen or sulfur and optionally can be interrupted by one or more —(CO)— or —SO$_2$— groups in the ring, and optionally one or more double bonds can be contained in the ring, and whereby the C$_2$-C$_6$-heterocycloalkyl ring itself in each case optionally can be substituted in one or more places, in the same way or differently, with cyano, halogen, C$_1$-C$_6$-alkyl, C$_1$-C$_6$-hydroxyalkyl, C$_1$-C$_6$-alkoxy, C$_3$-C$_6$-cycloalkyl, or with the group —NR$^3$R$^4$ or —CO—NR$^3$R$^4$, or R$^3$ and R$^4$ together form a C$_2$-C$_6$-heterocycloalkyl ring, whereby the heterocycloalkyl in the ring contains at least one atom, which is the same or different, from the following group of nitrogen, oxygen or sulfur and optionally can be interrupted by one or more —(CO)— or —SO$_2$— groups in the ring, and optionally one or more double bonds can be contained in the ring, and the heterocycloalkyl ring itself optionally can be substituted in one or more places, in the same way or differently, with halogen, C$_1$-C$_6$-alkyl, C$_3$-C$_6$-cycloalkyl, C$_1$-C$_6$-hydroxyalkyl, C$_1$-C$_6$-alkoxyalkyl, cyano, hydroxy or with the group —NR$^3$R$^4$, and R$^5$ stands for C$_1$-C$_6$-alkyl that optionally is substituted in one or more places, in the same way or differently, with halogen, hydroxy, C$_2$-C$_6$-heterocycloalkyl, C$_1$-C$_6$-hydroxyalkoxy or with the group —NR$^3$R$^4$, whereby the heterocycloalkyl in the ring contains at least one atom, which is the same or different, from the following group of nitrogen, oxygen or sulfur and optionally can be interrupted by one or more —(CO)— or —SO$_2$— groups in the ring, and optionally one or more double bonds can be contained in the ring, and the heterocycloalkyl ring itself optionally can be substituted in one or more places, in the same way or differently, with C$_1$-C$_6$-alkyl, C$_3$-C$_6$-cycloalkyl, C$_1$-C$_6$-hydroxyalkyl, C$_1$-C$_6$-alkoxyalkyl, cyano, hydroxy or with the group —NR$^3$R$^4$, as well as their solvates, hydrates, stereoisomers, diastereomers, enantiomers and salts, achieve the object.

The compounds of general formula I according to the invention essentially inhibit the polo-like kinases, upon which is based their action against, for example, cancer, such as solid tumors and leukemia; auto-immune diseases, such as psoriasis, alopecia, and multiple sclerosis, chemotherapy agent-induced alopecia and mucositis; cardiovascular diseases, such as stenoses, arterioscleroses and restenoses; infectious diseases, such as those, e.g., produced by unicellular parasites, such as trypanosoma, toxoplasma or plasmodium, or produced by fingi; nephrological diseases, such as, e.g., glomerulonephritis, chronic neurodegenerative diseases, such as Huntington's disease, amyotropic lateral sclerosis, Parkinson's disease, AIDS, dementia and Alzheimer's disease; acute neurodegenerative diseases, such as ischemias of the brain and neurotraumas; viral infections, such as, e.g., cytomegalic infections, herpes, hepatitis B and C, and HIV diseases.

Alkyl is defined in each case as a straight-chain or branched alkyl radical, such as, for example, methyl, ethyl, propyl, isopropyl, butyl, isobutyl, sec.-butyl, tert.-butyl, pentyl, isopentyl, neopentyl, hexyl, heptyl, octyl, nonyl and decyl.

The alkyl groups of the substituents A, B, L, M, X, Y, R$^1$, R$^2$, R$^3$, R$^4$ and R$^5$ of general formula (I) have the meaning mentioned in the paragraph above. For substituents A, B, M, R$^2$, R$^3$, R$^4$, and R$^5$, C$_1$-C$_6$-alkyl radicals are preferred and C$_1$-C$_3$-alkyl radicals are especially preferred. An alkyl group that is quite especially preferred for M is propyl. Alkyl groups that are quite especially preferred for R$^3$ and R$^4$ are methyl and ethyl. An alkyl group that is quite especially preferred for R$^5$ is methyl. For substituents L, X and Y, C$_1$-C$_6$-alkyl radicals are preferred, and C$_1$-C$_4$-alkyl radicals are especially preferred. For substituents R$^1$, a C$_1$-C$_4$-alkyl group is preferred, and an ethyl group is especially preferred.

Alkoxy is defined in each case as a straight-chain or branched alkoxy radical, such as, for earplug, methyloxy, ethyloxy, propyloxy, isopropyloxy, butyloxy, isobutyloxy, sec.-butyloxy, pentyloxy, isopentyloxy, hexyloxy, heptyloxy, octyloxy, nonyloxy or decyloxy.

The alkoxy groups of the substituents of general formula (I) have the meaning that is mentioned in the paragraph above. $C_1$-$C_6$-Alkoxy groups are preferred, and $C_1$-$C_3$-alkoxy groups are especially preferred. In the case of substituents of general formula (I), preferred alkoxyalkoxy groups are $C_1$-$C_3$-alkoxy-$C_1$-$C_3$-alkoxy groups. A $C_1$-alkoxy-$C_2$-alkoxy group is especially preferred.

The alkenyl substituents in each case are straight-chain or branched, whereby, for example, the following radicals are meant: vinyl, propen-1-yl, propen-2-yl, but-1-en-1-yl, but-1-en-2-yl, but-2-en-1-yl, but-2-en-2-yl, 2-methyl-prop-2-en-1-yl, 2-methyl-prop-1-en-1yl, but-1-en-3-yl, but-3-en-1-yl, and allyl.

Alkinyl is defined in each case as a straight-chain or branched alkinyl radical that contains 2-6, preferably 2-4, C atoms. For example, the following radicals can be mentioned: acetylenyl, propin-1-yl, propin-3-yl, (propargyl), but-1-in-1-yl, but-1-in-4-yl, but-2-in-1-yl, but-1-in-3-yl, 3-methyl-but-1-in-3-yl, etc.

$C_2$-$C_9$-Heterocycloalkyl stands for a heterocycloalkyl ring that comprises 2-9 carbon atoms, whereby the heterocycloalkyl ring in addition contains at least one atom, which is the same or different, from the following group of oxygen, sulfur or nitrogen, and the ring optionally can be interrupted by one or more —(CO)—, (CS)— or —$SO_2$— groups, and optionally one or more double bonds can be contained in the ring, and the ring itself optionally can be substituted in one or more places, in the same way or differently. Only those combinations are meant, however, that are useful from the viewpoint of one skilled in the art, in particular in reference to ring strain.

As heterocycloalkyls, there can be mentioned, e.g.: oxiranyl, oxethanyl, dioxolanyl, dithianyl, dioxanyl, aziridinyl, azetidinyl, tetrahydrofuranyl, tetrahydropyranyl, dihydrooxazolyl, tetrahydrooxazolyl, tetrahydrothiazolyl, tetrahydroisoquinolinyl, octahydroisoquinolinyl, decahydroisoquinolinyl, tetrahydroquinolinyl, octahydroquinolinyl, tetrahydroimidazolonyl, pyrazolidinyl, pyrrolidinyl, pyyrolidonyl, piperidinyl, piperidonyl, piperazinyl, piperazinonyl, N-methylpyrolidinyl, 2-hydroxymethylpyrolidinyl, 3-hydroxypyrolidinyl, N-methylpiperazinyl, N-benzyl-piperazinyl, N-acetylpiperazinyl, N-methylsulfonylpiperazinyl, 4-hydroxypiperidinyl, 4-aminocarbonylpiperidinyl, 2-hydroxyethylpiperidinyl, 4-hydroxymethylpiperidinyl, imidazolidinyl, tetrahydroimidazolonyl, morpholinyl, thiomorpholinyl, 1,1-dioxo-thiomorpholinyl, trithianyl, tetrahydrotriazinothionyl, triazinothionyl, quinuclidinyl, nortropinyl, pyrridonyl, etc., or rings of the above-mentioned, which are benzocondensed, such as, for example, benzopyrrolidinyl, benzomorpholinyl, etc.

Substituents A, B and W according to general formula (I) have as preferred heterocycloalkyls those that have 5, 6 or 10 ring atoms. The heterocycloalkyls of substituent W have more preferably 5 or 6 ring atoms and most preferably 5 ring atoms. The heterocycloalkyls with 5, 6 or 10 ring atoms have 1 to 4 nitrogen atoms and/or 1 to 2 oxygen atoms and/or 1 to 2 sulfur atoms, which can occur in all subcombinations in the ring system as long as they do not exceed the number specified for the respective heteroatom and the total maximum number of four heteroatoms. Especially preferred heterocycloalkyls for substituents A and B according to general formula (I) are pyrrolidine, piperidine, piperazine, morpholine, thiomorpholine, tetrahydroisoquinoline and/or decahydroisoquinoline. The heterocycloalkyl of substituents A and B according to general formula (D) quite especially preferably stands for pyrrolidine and/or decahydroisoquinoline. Hydrogenated oxazoles and in particular 4,5-dihydrooxazole are especially preferred heterocycloalkyls for substituent W according to general formula (I).

Substituents L, M, X, Y, $R^3$, $R^4$ and $R^5$ according to general formula (I) have as preferred heterocycloalkyls those that have a heterocycloalkyl ring that comprises 2-6 carbon atoms. For L, M, X, Y, $R^3$, $R^4$ and $R^5$, other preferred heterocycloalkyls are those that have 5 or 6 ring atoms and have 1 to 4 nitrogen atoms and/or 1 to 2 oxygen atoms and/or 1 to 2 sulfur atoms, which can occur in all subcombinations in the ring system as long as they do not exceed the number specified for the respective heteroatom and the total maximum number of four heteroatoms. Especially preferred heterocycloalkyls for substituents L and M according to general formula (I) are pyrrolidine, piperidine, piperazine, morpholine, thiomorpholine and/or decahydroisoquinoline. According to general formula (I), the heterocycloalkyl of L quite especially preferably stands for piperidine and/or morpholine. According to general formula (I), the heterocycloalkyl of M quite especially preferably stands for pyrrolidine.

Substituents on the heterocycloalkyl ring can be, for example: cyano, halogen, hydroxy, $C_1$-$C_6$-alkyl, $C_1$-$C_6$-alkoxy, $C_1$-$C_6$-alkoxyalkyl, $C_1$-$C_6$-hydroxyalkyl, $C_3$-$C_6$-cycloalkyl, or aryl or $C_1$-$C_6$-alkyl that optionally is substituted in one or more places, in the same way or differently, with halogen, hydroxy or $C_1$-$C_6$-alkylthio, or a substituent from the group —(CO)—$C_1$-$C_6$-alkyl, —(CO)—O—$C_1$-$C_6$-alkyl, —($SO_2$)—$C_1$-$C_6$-alkyl, —$SO_2$)-phenyl, —$NH_2$, —N($C_1$-$C_6$-alkyl)$_2$, —NH($C_1$-$C_6$-alkyl), etc.

Cycloalkyls are defined as monocyclic alkyl rings, such as cyclopropyl, cyclobutyl, cyclopentyl, cyclohexyl or cycloheptyl, but also bicyclic rings or tricyclic rings, such as, for example, adamantanyl. The cycloalkyl can optionally also be benzocondensed, such as, e.g., (tetralin)yl, etc. The cycloalkyl for cyclopentyl or cyclohexyl preferably stands for substituents X and Y of general formula (I). The cycloalkyl for cyclopropyl preferably stands for substituents $R^1$ of general formula (I).

Halogen is defined in each case as fluorine, chlorine, bromine or iodine. Fluorine and chlorine are preferred.

The heteroaryl radical comprises a monovalent, aromatic ring system with 5-16 ring atoms in each case, preferably 5 to 10 ring atoms, and especially preferably 5 to 6 ring atoms, and with at least one heteroatom that is different from a carbon, such as oxygen, nitrogen or sulfur. The heteroaryl radical can be monocyclic, bicyclic or tricyclic, and in addition can be benzocondensed in each case. Only those combinations are meant, however, that are useful from the viewpoint of one skilled in the art, in particular in reference to ring strain.

For example, there can be mentioned:

Thienyl, furanyl, pyrrolyl, oxazolyl, thiazolyl, imidazolyl, pyrazolyl, isoxazolyl, isothiazolyl, oxadiazolyl, triazolyl, thiadiazolyl, etc., and benzo derivatives thereof, such as, e.g., benzofuranyl, benzothienyl, benzoxazolyl, benzimidazolyl, indazolyl, indolyl, isoindolyl, etc.; or pyridyl, pyridazinyl, pyrimidinyl, pyrazinyl, triazinyl, etc., and benzo derivatives thereof, such as, e.g., quinolyl, isoquinolyl, etc.; or oxepinyl, azocinyl, indolizinyl, indolyl, indolinyl, isoindolyl, indazolyl, benzimidazolyl, benzothiazolyl, purinyl, cinnolinyl, phthalazinyl, quinazolinyl, quinoxalinyl, naphthyridinyl, pteridinyl, carbazolyl, acridinyl, phenazinyl, phenothiazinyl, phenoxazinyl, xanthenyl, tetralinyl, etc.

Preferred heteroaryl radicals are thienyl, furanyl, oxazolyl, oxadiazolyl, triazolyl, thiazolyl, thiophenyl, imidazolyl, indolyl, indazolyl, pyridinyl, pyrimidinyl, triazinyl, quinolinyl, pyrrolyl, isoquinolinyl and benzo derivatives thereof.

For substituent Q according to general formula (I), an especially preferred heteroaryl radical is a pyridyl, quinolinyl, benzimidazolyl, indolyl, indazolyl, thiazolyl, imidazolyl or pyrimidinyl. According to general formula (I), the heteroaryl radical of substituent Q stands more preferably for pyridyl, indolyl or pyrimidinyl and most preferably for pyridyl. For substituent W according to general formula (I), an especially preferred heteroaryl radical is an oxazolyl, oxadiazolyl, triazolyl, thiazolyl, pyridinyl, thienyl, benzo[b]thiophenyl, benzoimidazolyl, benzothiazolyl or a pyrrolyl.

The aryl radical comprises 3-12 carbon atoms in each case and can be benzocondensed in each case.

For example, there can be mentioned: cyclopropenyl, cyclopentadienyl, phenyl, tropyl, cyclooctadienyl, indenyl, naphthyl, azulenyl, biphenyl, fluorenyl, anthracenyl, tetralinyl, etc. A preferred aryl radical of this invention is a phenyl radical with 6 carbon atoms and/or a naphthyl radical with 10 carbon atoms. A phenyl radical is especially preferred.

Thus, as used in this application, for example in connection with the definition of "$C_1$-$C_6$-alkyl," "$C_1$-$C_6$" refers to an alkyl group with a finite number of 1 to 6 carbon atoms, i.e., 1, 2, 3, 4, 5, or 6 carbon atoms. The definition of "$C_1$-$C_6$" is further interpreted that any possible sub-area, such as, for example, $C_1$-$C_6$, $C_2$-$C_6$, $C_3$-$C_6$, $C_4$-$C_6$, $C_5$-$C_6$, $C_2$-$C_5$, $C_3$-$C_4$, $C_1$-$C_2$, $C_1$-$C_3$, $C_1$-$C_4$, $C_1$-$C_5$, or $C_1$-$C_6$, is co-contained Analogously to this, "$C_1$-$C_6$," for example in connection with the definition of "$C_1$-$C_6$-alkoxy," refers to an alkoxy group with a finite number of 1 to 6 carbon atoms, i.e., 1, 2, 3, 4, 5 or 6 carbon atoms. The definition of "$C_1$-$C_6$" is thus interpreted that any possible subarea, such as, for example, $C_1$-$C_6$, $C_2$-$C_6$, $C_3$-$C_6$, $C_4$-$C_6$, $C_5$-$C_6$, $C_2$-$C_5$, $C_3$-$C_4$, $C_1$-$C_2$, $C_1$-$C_3$, $C_1$-$C_4$, $C_1$-$C_5$, or $C_1$-$C_6$, is co-contained in the definition.

All area information of the application not explicitly cited here is defined analogously to the above areas of "$C_1$-$C_6$" that are mentioned by way of example.

Isomers are defined as chemical compounds of the same summation formula but different chemical structure. In general, constitutional isomers and stereoisomers are distinguished.

Constitutional isomers have the same summation formula but are distinguished by the way in which their atoms or atom groups are linked. These include functional isomers, position isomers, tautomers or valence isomers.

Stereoisomers have basically the same structure (constitutional)—and thus also the same summation formula—but are distinguished by the spatial arrangement of the atoms.

In general, configurational isomers and conformational isomers are distinguished. Configurational isomers are stereoisomers that can be converted into one another only by bond breaking. These include enantiomers, diastereomers and E/Z (cis/trans)isomers.

Enantiomers are stereoisomers that behave like image and mirror image to one another and do not exhibit any plane of symmetry. All stereoisomers that are not enantiomers are referred to as diastereomers. E/Z (cis/trans)isomers on double bonds are a special case.

Conformational isomers are stereoisomers that can be converted into one another by the rotation of single bonds.

To delimit types of isomerism from one another, see also the IUPAC Rules, Section E (Pure Appl. Chem. 45, 11-30, 1976).

The compounds of general formula I according to the invention also contain the possible tautomeric forms and comprise the E-or Z-isomers or, if a chiral center is present, also the racemates and enantiomers. Among the latter, double-bond isomers are also defined.

The compounds according to the invention can also be present in the form of solvates, especially hydrates, whereby the compounds according to the invention consequently contain polar solvents, especially water, as structural elements of the crystal lattice of the compounds according to the invention. The portion of polar solvent, especially water, can be present in a stoichiometric or else unstoichiometric ratio. In the case of stoichiometric solvates and hydrates, hemi-, (semi-), mono-, sesqui-, di-, tri-, tetra-, penta-, etc., solvates or hydrates are also mentioned.

If an acid group is included, the physiologically compatible salts of organic and inorganic bases are suitable as salts, such as, for example, the readily soluble alkali and alkaline-earth salts, as well as N-methyl-glucamine, dimethyl-glucamine, ethyl-glucamine, lysine, 1,6-hexadiamine, ethanolamine, glucosamine, sarcosine, serinol, tris-hydroxy-methyl-amino-methane, aminopropane diol, Sovak base, and 1-amino-2,3,4-butanetriol.

If a basic group is included, the physiologically compatible salts of organic and inorganic acids are suitable, such as hydrochloric acid, sulfuric acid, phosphoric acid, citric acid, tartaric acid, fumaric acid, maleic acid, malic acid, i.a.

Of these compounds of general formula (I), those compounds are preferred in which
  Q stands for phenyl, pyridyl, naphthyl, quinolinyl, benzimidazolyl, indolyl, indazolyl, thiazolyl, imidazolyl or pyrimidinyl, as well as their solvates, hydrates, stereoisomers, diastereomers, enantiomers and salts.

Further preferred are those compounds of general formula (I), in which
  Q stands for phenyl, pyridyl, naphthyl, indolyl or pyrimidinyl,
  M stands for $C_1$-$C_6$-alkyl that optionally is substituted in one or more places, in the same way or differently, with $C_2$-$C_6$-heterocycloalkyl, whereby the heterocycloalkyl in the ring contains at least one atom, which is the same or different, from the following group of nitrogen, oxygen or sulfur,
  $R^3$ and $R^4$, independently of one another, stand for hydrogen or for $C_1$-$C_6$-alkyl, $C_1$-$C_6$-alkoxy or —CO—$C_1$-$C_6$-alkyl that optionally is substituted in one or more places, in the same way or differently, with halogen, hydroxy, or $C_1$-$C_6$-hydroxyalkoxy,
  $R^5$ stands for $C_1$-$C_6$-alkyl that optionally is substituted in one or more places, in the same way or differently, with halogen, hydroxy, $C_2$-$C_6$-heterocycloalkyl, $C_1$-$C_6$-hydroxyalkoxy or with the group —$NR^3R^4$, whereby the heterocycloalkyl in the ring contains at least one atom, which is the same or different, from the following group of nitrogen, oxygen or sulfur, and optionally can be interrupted by one or more —(CO)— or —$SO_2$— groups in the ring, and optionally one or more double bonds can be contained in the ring, as well as their solvates, hydrates, stereoisomers, diastereomers, enantiomers and salts.

In addition, those compounds of general formula (I), in which
  Q stands for phenyl or pyridyl,
  W stands for oxazole, 4,5-dihydrooxazole, oxadiazole, triazole, thiazole, pyridine, thiophene, benzo[b]thiophene, benzoimidazole, benzothiazole or pyrrole,
  X and Y, independently of one another, stand for hydrogen or for $C_1$-$C_6$-alkyl or aryl that optionally is substituted in one or more places, in the same way or differently, with halogen, hydroxy, $C_1$-$C_6$-alkoxy, $C_1$-$C_6$-alkylthio or aryl, or for the group —$COOR^5$ or —$CONR^3R^4$, or X and Y together are formed by the same atom or by adjacent atoms of W from a cyclopropyl ring, a cyclobutyl ring, a cyclopentyl ring or a cyclohexyl ring, $R^1$ stands for $C_1$-$C_4$-alkyl that optionally is substituted in one or more places, in the same way or differently, with halogen, $R^5$ stands for $C_1$-$C_6$-alkyl that optionally is substituted in one or more places, in the same way or differently, with halogen, hydroxy, or $C_1$-$C_6$-hydroxyalkoxy, as well as their solvates, hydrates, stereoisomers, diastereomers, enantiomers and salts, are preferred.

In turn, those substances of general formula (I), in which

A and B, independently of one another, stand for hydrogen or halogen or for $C_1$-$C_3$-alkyl or $C_1$-$C_6$-alkoxy that optionally is substituted in one or more places, in the same way or differently, with pyrrolidinyl, piperidinyl, piperazinyl, morpholinyl, thiomorpholinyl, tetrahydroisoquinolinyl or decahydroisoquinolinyl, whereby pyrrolidinyl, piperidinyl, piperazinyl, morpholinyl, thiomorpholinyl, tetrahydroisoquinolinyl or decahydroisoquinolinyl itself optionally can be substituted in one or more places, in the same way or differently, with halogen or with $C_1$-$C_6$-alkyl that optionally is substituted in one or more places, in the same way or differently, with halogen, or with the group —$COR^2$, or for —$NR^3R^4$, —$NR^3(CO)$-L or —$CO(NR^3)$-M, L stands for $C_1$-$C_6$-alkyl that optionally is substituted in one or more places, in the same way or differently, with hydroxy, $C_1$-$C_6$-alkoxyalkoxy, pyrrolidinyl, piperidinyl, piperazinyl, morpholinyl, thiomorpholinyl or decahydroisoquinolinyl, whereby pyrrolidinyl, piperidinyl, piperazinyl, morpholinyl, thiomorpholinyl or decahydroisoquinolinyl itself optionally can be substituted in one or more places, in the same way or differently, with halogen or with $C_1$-$C_6$-alkyl that optionally is substituted in one or more places, in the same way or differently, with halogen, or with the group —$COR^2$, M stands for $C_1$-$C_6$-alkyl that optionally is substituted in one or more places, in the same way or differently, with pyrrolidinyl, X and Y, independently of one another, stand for hydrogen, or for $C_1$-$C_6$-alkyl or phenyl that optionally is substituted in one or more places, in the same way or differently, with halogen, $C_1$-$C_6$-alkoxy, $C_1$-$C_6$-alkylthio or phenyl, or for the group —$COOR^5$ or —$CONR^3R^4$, or X and Y together are formed by the same atom or by adjacent atoms of W from a cyclopentyl ring or a cyclohexyl ring, $R^2$ stands for $C_1$-$C_6$-alkyl, $R^3$ and $R^4$, independently of one another, stand for hydrogen or $C_1$-$C_6$-alkyl, and $R^5$ stands for $C_1$-$C_6$-alkyl, as well as their solvates, hydrates, stereoisomers, diastereomers, enantiomers and salts, are preferred.

Those compounds of general formula (I), in which

A and B, independently of one another, stand for hydrogen or halogen, or for $C_1$-$C_3$-alkyl that optionally is substituted in one or more places, in the same way or differently, with pyrrolidinyl, piperidinyl, piperazinyl, morpholinyl, thiomorpholinyl, tetrahydroisoquinolinyl or decahydroisoquinolinyl, or for —$NR^3R^4$, —$NR^3(CO)$-L or —$CO(NR^3)$-M, L stands for $C_1$-$C_6$-alkyl that optionally is substituted in one or more places, in the same way or differently, with hydroxy, or $C_1$-$C_6$-alkoxy-$C_1$-$C_6$-alkoxy, M stands for $C_1$-$C_6$-alkyl that is substituted with pyrrolidinyl, $R^1$ stands for $C_1$-$C_4$-alkyl, as well as their solvates, hydrates, stereoisomers, diastereomers, enantiomers or salts, are especially preferred.

Those substances of general formula (I), in which

A and B, independently of one another, stand for hydrogen or halogen, or for $C_1$-$C_3$-alkyl that optionally is substituted in one or more places, in the same way or differently, with pyrrolidinyl or decahydroisoquinolinyl, or for —$NR^3R^4$, —$NR^3(CO)$-L or —$CO(NR^3)$-M, L stands for isopropyl, tert-butyl or methyl that optionally is substituted in one or more places, in the same way or differently, with hydroxy or $C_1$-$C_6$-alkoxyalkoxy, M stands for $C_1$-$C_3$-alkyl that is substituted with pyrrolidinyl, X and Y, independently of one another, stand for hydrogen, or for methyl, ethyl, isopropyl, propyl, isobutyl, tert-butyl or phenyl that optionally is substituted in one or more places, in the same way or differently, with halogen, $C_1$-$C_6$-alkoxy, $C_1$-$C_6$-alkylthio or phenyl, or for the group —$COOR^5$ or —$CONR^3R^4$, or X and Y together are formed by the same atom or by adjacent atoms of W from a cyclopentyl ring or a cyclohexyl ring, $R^1$ stands for ethyl, $R^3$ and $R^4$, independently of one another, stand for hydrogen or $C_1$-$C_3$-alkyl, and $R^5$ stands for methyl, as well as their solvates, hydrates, stereoisomers, diastereomers, enantiomers and salts, are preferred in particular.

Compounds of general formula I according to one of claims 1-7, in which $R^1$ stands for $C_1$-$C_4$-alkyl, or preferably for ethyl, are another preferred subject of the invention.

Compounds of general formula I according to one of claims 1-7, in which $R^2$ stands for $C_1$-$C_6$-alkyl, are another preferred subject of the invention.

Compounds of general formula I according to one of claims 1-7, in which $R^3$ and $R^4$, independently of one another, stand for hydrogen or $C_1$-$C_6$-alkyl, or preferably for hydrogen or $C_1$-$C_3$-alkyl, are another preferred subject of the invention.

Compounds of general formula I according to one of claims 1-7, in which $R^5$ stands for $C_1$-$C_6$-alkyl, preferably for $C_1$-$C_3$-alkyl and more preferably for methyl, are another preferred subject of the invention.

Compounds of general formula I according to one of claims 1-7, in which X and Y, independently of one another, stand for hydrogen or for $C_1$-$C_6$-alkyl or phenyl that optionally is substituted in one or more places, in the same way or differently, with halogen, $C_1$-$C_6$-alkoxy, $C_1$-$C_6$-alkylthio or phenyl, or for the group —$COOR^5$ or —$CONR^3R^4$, or X and Y together are formed by the same atom or by adjacent atoms of W from a cyclopentyl ring or a cyclohexyl ring, are another preferred subject of the invention.

Compounds of general formula I according to one of claims 1-7, in which M stands for $C_1$-$C_6$-alkyl that optionally is substituted in one or more places, in the same way or differently, with pyrrolidinyl, but preferably for $C_1$-$C_3$-alkyl that is substituted with pyrrolidinyl, are another preferred subject of the invention.

Compounds of general formula I according to one of claims 1-7, in which Q stands for phenyl, pyridyl, naphthyl, indolyl or pyrimidinyl are another preferred subject of the invention. In this case, Q quite especially preferably stands for phenyl or pyridyl.

Compounds of general formula I according to one of claims 1-7 in which W stands for oxazole, 4,5-dihydrooxazole, oxadiazole, triazole, thiazole, pyridine, thiophene, benzo[b]thiophene, benzoimidazole, benzothiazole or pyrrole are another preferred subject of the invention.

Another subject of this invention includes intermediate products of general formula (II)

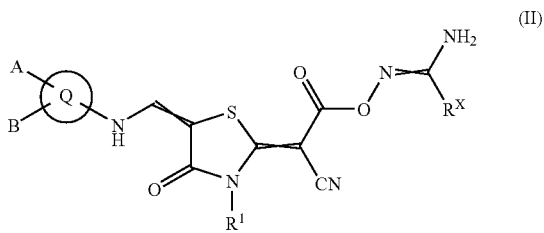

in which A, B, Q and $R^1$ have the meaning that is indicated in general formula (I), according to one of claims 1 to 7, and $R^x$ stands for $C_1$-$C_3$-alkyl, as well as their solvates, hydrates, stereoisomers, diastereomers, enantiomers and salts for the production of compounds of general formula (I).

Another preferred subject of this invention includes intermediate products of general formula (II), in which Q stands for phenyl; A and B, independently of one another, stand for hydrogen or for the group —NH(CO)—$C_1$-$C_6$-alkyl or —NH(CO)-$C_1$-$C_6$-alkoxyalkoxy, $R^1$ stands for ethyl, and $R^x$ stands for methyl.

An especially preferred subject of this invention are intermediate products of general formula (II) with the following formulas:

3-{[2-[1-Cyano-1-((S)-2-hydroxy-1-methyl-ethylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide, 3-{[2-[1-Cyano-1-((S)-1-hydroxymethyl-propylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide, 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((1S,2S)-2-hydroxy-cyclopentyl)-acetamide, 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-(2-hydroxy-propyl)-acetamide, 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((1S,2S)-2-hydroxy-cyclohexyl)-acetamide, 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((1R,2S)-2-hydroxy-1-methyl-2-phenyl-ethyl)-acetamide, 2-Cyano-2-[3-ethyl-5-[1-[3-(2-hydroxy-2-methyl-propionylamino)-phenylamino]-meth-(E/Z)-ylidene]-4-oxo-thiazolidin-(2-(E or Z))-ylidene]-N-((1S,2S)-2-hydroxy-cyclopentyl)-acetamide, 2-Cyano-2-[3-ethyl-5-[1-{3-[2-(2-methoxy-ethoxy)-acetylamino]-phenylamino}-(E/Z)-ylidene]-4-oxo-thiazolidin-(2-(E or Z))-ylidene]-N-((1S,2S)-2-hydroxy-cyclopentyl)-acetamide, 2-Cyano-2-[5-[1-[6-(2,2-dimethyl-propionylamino)-pyridin-2-ylamino]-meth-(E/Z)-ylidene]-3-ethyl-4-oxo-thiazolidin-(2-(E or Z))-ylidene]-N-((1S,2S)-2-hydroxy-cyclopentyl)-acetamide, 2-Cyano-2-[3-ethyl-5-[1-{6-[2-(2-methoxy-ethoxy)-acetylamino]-pyridin-2-ylamino}-meth-(E/Z)-ylidene]-4-oxo-thiazolidin-(2-(E or Z))-ylidene]-N-((1S,2S)-2-hydroxy-cyclopentyl)-acetamide and 2-Cyano-2-[3-ethyl-5-[1-(2-ethylamino-pyridin-4-ylamino)-meth-(E/Z)-ylidene]-4-oxo-thiazolidin-(2-(E or Z))-ylidene]-N-((1S,2S)-2-hydroxy-cyclopentyl)-acetamide.

Another subject of the invention includes the use of intermediate products of general formula (II) for the production of compounds of general formula (I).

To use the compounds of general formula I according to the invention as pharmaceutical agents, the latter are brought into the form of a pharmaceutical preparation, which in addition to the active ingredient for enteral or parenteral administration contains suitable pharmaceutical, organic or inorganic inert support media, such as, for example, water, gelatin, gum arabic, lactose, starch, magnesium stearate, talc, vegetable oils, polyalkylene glycols, etc. The pharmaceutical preparations can be present in solid form, for example as tablets, coated tablets, suppositories, or capsules, or in liquid form, for example as solutions, suspensions, or emulsions. Moreover, they optionally contain adjuvants, such as preservatives, stabilizers, wetting agents or emulsifiers; salts for changing the osmotic pressure or buffers. These pharmaceutical preparations are also subjects of this invention.

For parenteral administration, especially injection solutions or suspensions, especially aqueous solutions of active compounds in polyhydroxyethoxylated castor oil, are suitable.

As carrier systems, surface-active adjuvants, such as salts of bile acids or animal or plant phospholipids, but also mixtures thereof, as well as liposomes or their components can also be used.

For oral administration, especially tablets, coated tablets or capsules with talc and/or hydrocarbon vehicles or binders, such as, for example, lactose, corn or potato starch, are suitable. The administration can also be carried out in liquid form, such as, for example, as a juice, to which optionally a sweetener is added.

Enteral, parenteral and oral administrations are also subjects of this invention.

The dosage of the active ingredients can vary depending on the method of administration, age and weight of the patient, type and severity of the disease to be treated and similar factors. The daily dose is 0.5-1000 mg, preferably 50-200 mg, whereby the dose can be given as a single dose to be administered once or divided into two or more daily doses.

A subject of this invention is also the use of compounds of general formula I for the production of a pharmaceutical agent. Another subject of this invention is the use of the compounds of general formula I for the production of a pharmaceutical agent for treating cancer, auto-immune diseases, cardiovascular diseases, chemotherapy agent-induced alopecia and mucositis, infectious diseases, nephrological diseases, chronic and acute neurodegenerative diseases and viral infections, whereby cancer is defined as solid tumors and leukemia; auto-immune diseases are defined as psoriasis, alopecia and multiple sclerosis; cardiovascular diseases are defined as stenoses, arterioscleroses and restenoses; infectious diseases are defined as diseases that are caused by unicellular parasites; nephrological diseases are defined as glomerulonephritis; chronic neurodegenerative diseases are defined as Huntington's disease, amyotrophic lateral sclerosis, Parkinson's disease, AIDS-induced dementia and Alzheimer's disease; acute neurodegenerative diseases are defined as ischemias of the brain and neurotraumas; and viral infections are defined as cytomegalic infections, herpes, hepatitis B or C, and HIV diseases.

Subjects of this invention also include pharmaceutical agents for treating the above-cited diseases, which contain at least one compound according to general formula I, as well as pharmaceutical agents with suitable formulation substances and vehicles.

The compounds of general formula I according to the invention are, i.a., excellent inhibitors of the polo-like kinases, such as Plk1, Plk2, Plk3, and Plk4.

If the production of the starting compounds is not described, the latter are known or can be produced analogously to known compounds or to processes that are described here. It is also possible to perform all reactions that are described here in parallel reactors or by means of combinatory operating procedures. The isomer mixtures can be separated into the isomers, such as, e.g., into the enantiomers, diastereomers or E/Z isomers, according to commonly used methods, such as, for example, crystallization, chromatography or salt formation, if the isomers are not in a state of equilibrium with one another.

The production of the salts is carried out in the usual way by a solution of the compound of formula I being mixed with the equivalent amount of or excess base or acid, which optionally is in solution, and the precipitate being separated or the solution being worked up in the usual way.

SYNTHESIS DIAGRAMS

Synthesis Diagram 1

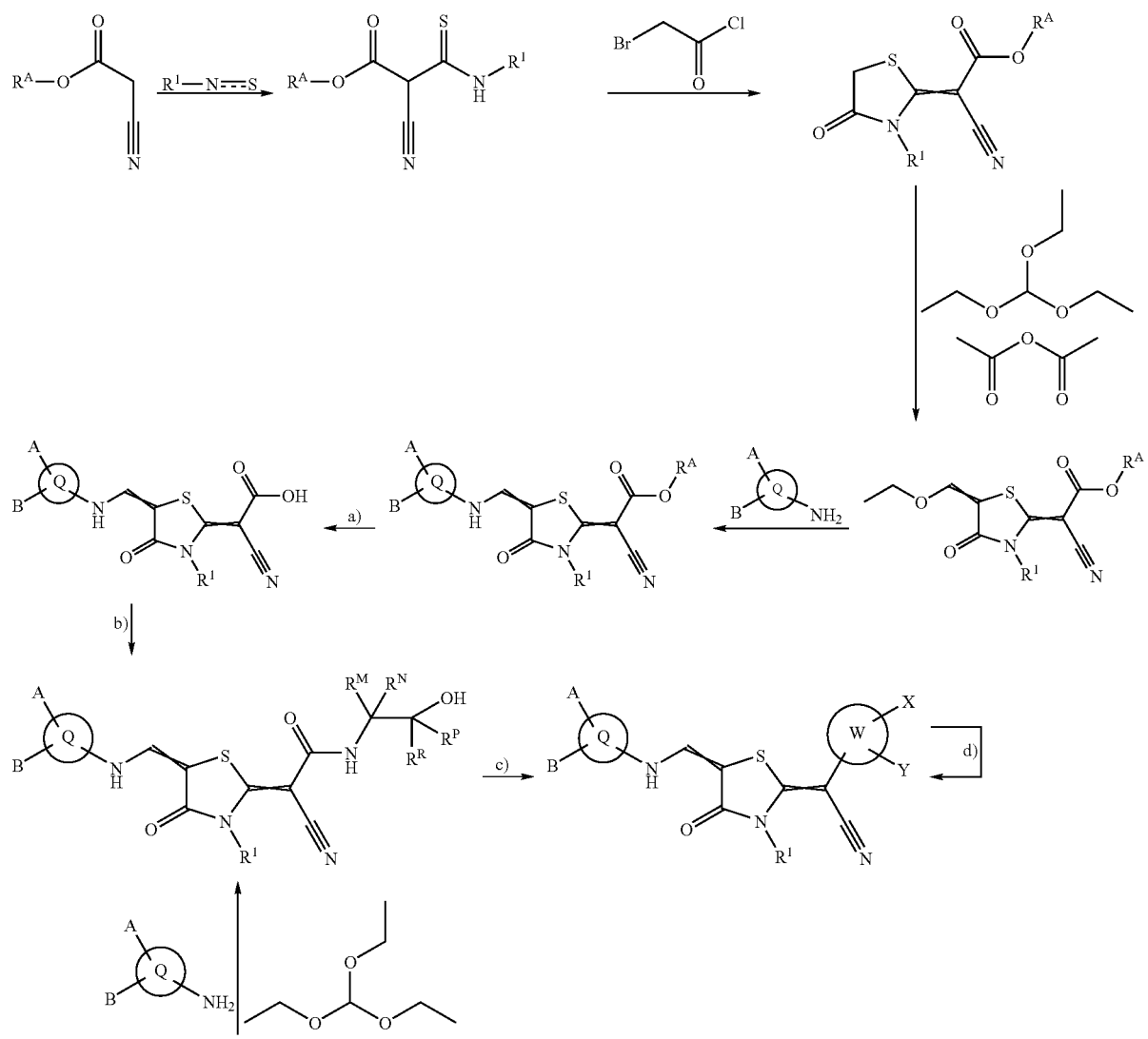

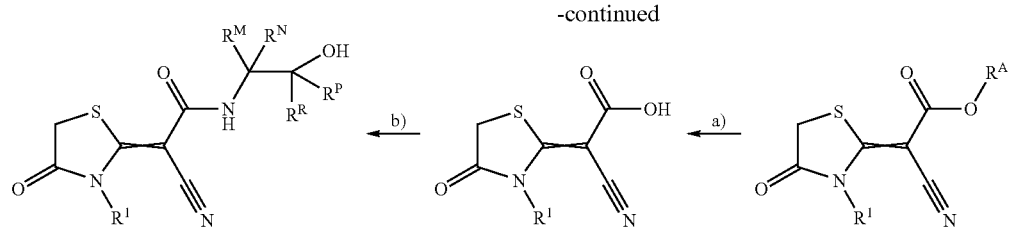
a) Ester cleavage; b) Coupling reaction; c) Cyclization; d) Subsequent reaction whereby $R^1$, A, B, X, Y, Q and W have the meaning that is indicated in general formula (I).
$R^A$=Ethyl, Allyl
$R^M$, $R^N$, $R^P$ and $R^R$=H or X or Y
Synthesis Diagram 2
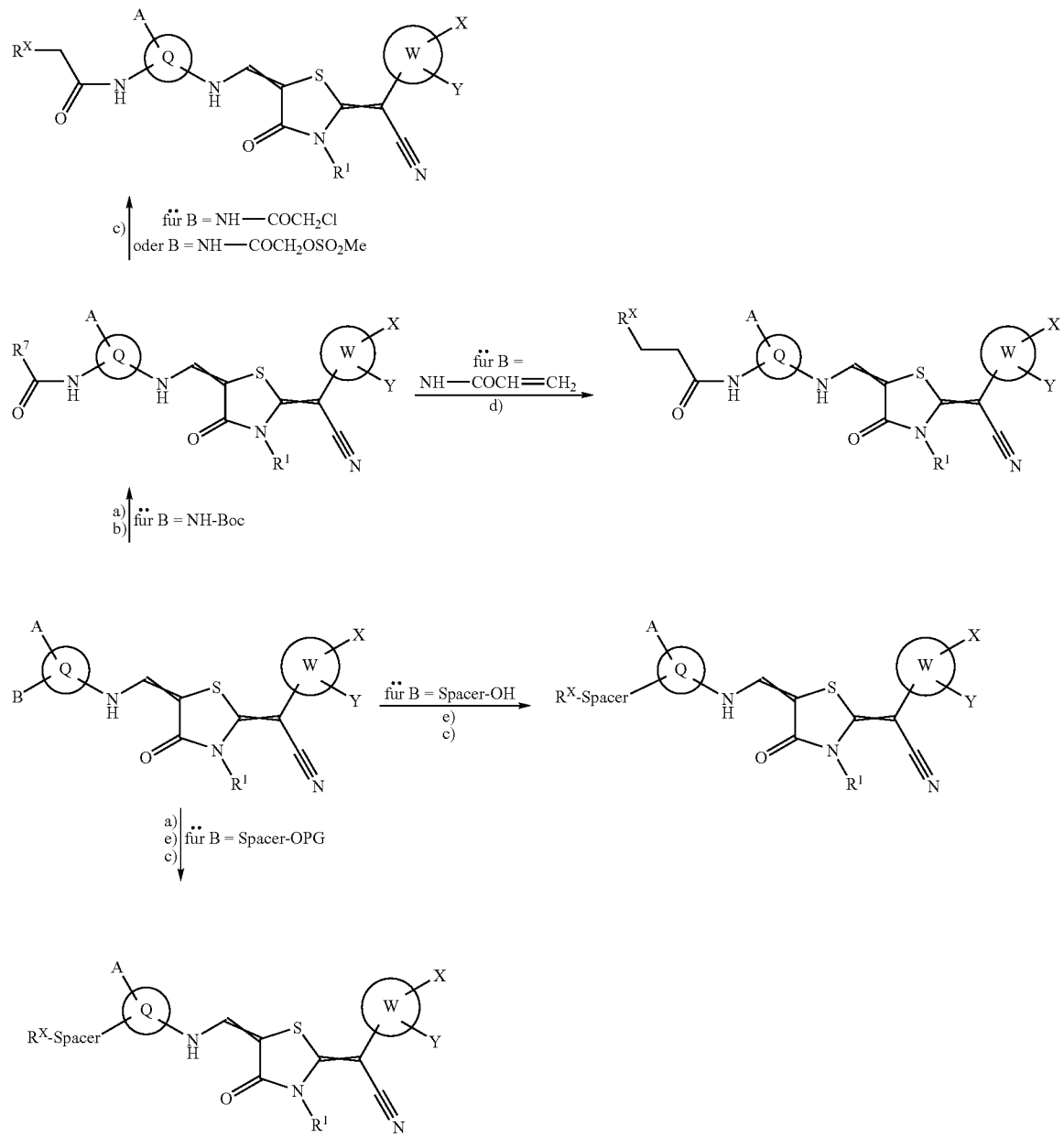

[Key to Synthesis Diagram 2:]
für=for
oder=or
a) Protection removal; b) Coupling reaction; c) Substitution; d) 1,4-Addition; e) To convert alcohol into the leaving group
PG=Protective group
Spacer=$C_1$-$C_6$-alkyl or NH—(CO)—$C_1$-$C_6$-alkyl.
$R^X$=—$NR^3R^4$ or $C_2$-$C_6$-heterocycloalkyl, whereby the heterocycloalkyl in the ring contains at least one atom, which is the same or different, from the following group of nitrogen, oxygen or sulfur and optionally can be interrupted by one or more —(CO)— or —$SO_2$— groups in the ring, and optionally one or more double bonds can be contained in the ring, and the ring itself optionally can be substituted in one or more places, in the same way or differently, with cyano or halogen, or with $C_1$-$C_6$-alkyl, $C_3$-$C_6$-cycloalkyl, or $C_1$-$C_6$-hydroxyalkyl that is substituted in one or more places, in the same way or differently, with halogen, or with the group —$COR^2$ or —$NR^3R^4$,
whereby $R^1$, $R^2$, $R^3$, $R^4$, A, B, X, Y, Q and W have the meaning that is indicated in general formula (I).

a) Deprotonation and successive reaction with isothiocyanate $R^1NCS$ and bromoacetyl chloride or chloroacetyl chloride,
whereby $R^1$, A, B, X, Y, Q and W have the meaning that is indicated in general formula (I).

Diagram No. 1 for Synthesis of Anilines

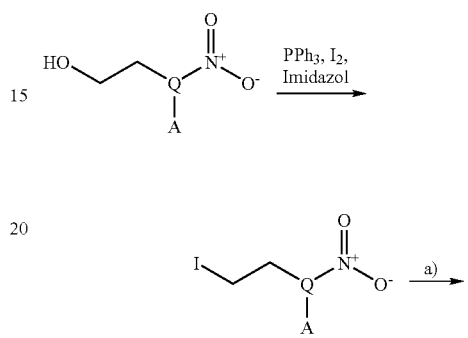

Synthesis Diagram 3

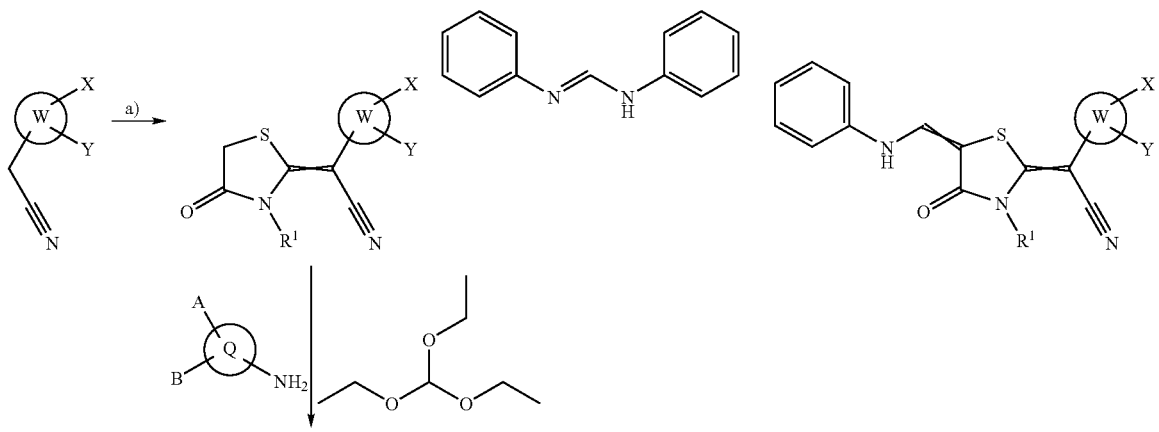

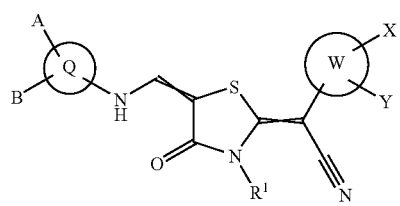

-continued

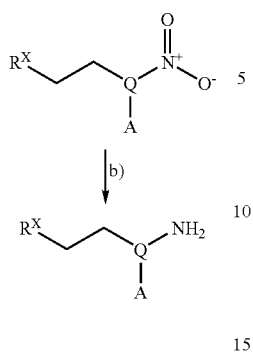

[Key:]
Imidazol=Imidazole
a) Substitution, b) Reduction whereby A, Q and Rx have the meaning that is indicated in Synthesis Diagram 2.

Diagram No. 2 for Synthesis of Anilines

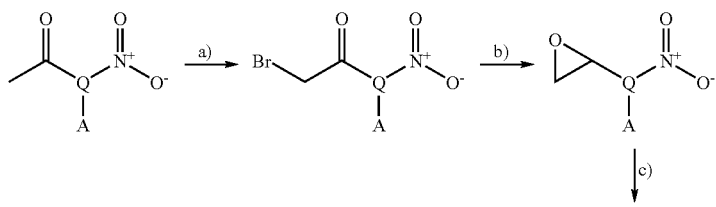

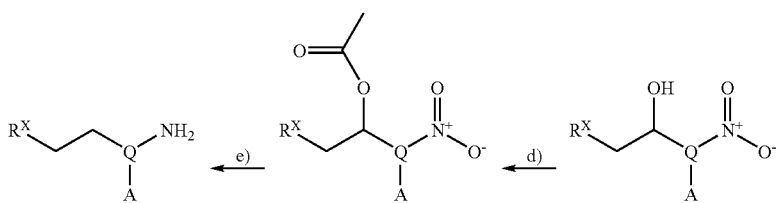

a) Bromination, b) Reduction of the ketone, followed by cyclization, c) Epoxide opening with $R^x$, d) Acetylation, e) Reduction whereby A, Q and Rx have the meaning that is indicated in Synthesis Diagram 2.

Diagram No. 3 For Synthesis of Anilines

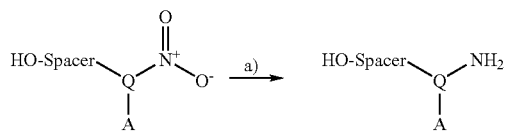

a) Reduction whereby A, Q and Spacer have the meaning that is indicated in Synthesis Diagram 2.

Diagram No. 4 for Synthesis of Anilines

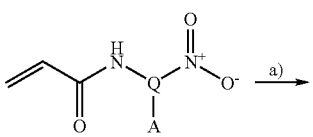

-continued

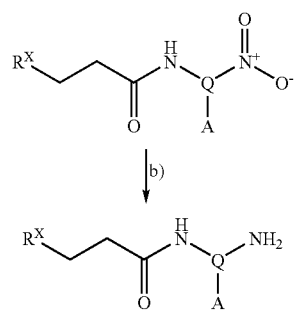

a) 1,4-Addition, b) Reduction whereby A, Q and $R^x$ have the meaning that is indicated in Synthesis Diagram 2.

Diagram No. 5 for Synthesis of Anilines

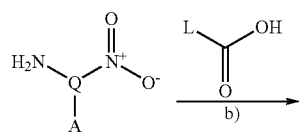

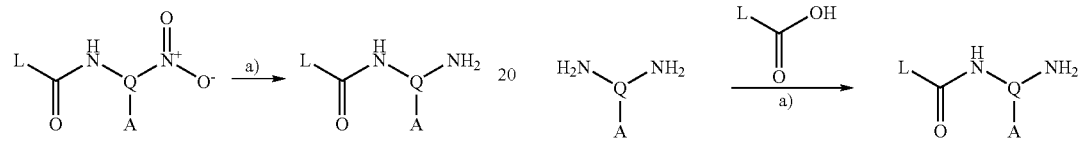

a) Reduction; b) Coupling reagent whereby A, Q and L have the meaning that is indicated in general formula (I).

Diagram No. 6 for Synthesis of Anilines

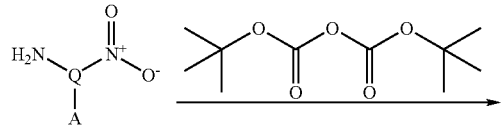

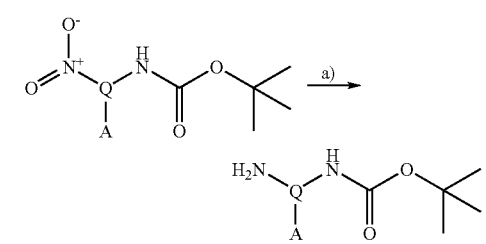

a) Reduction whereby A and Q have the meaning that is indicated in general formula (I).

Diagram No. 7 for Synthesis of Anilines

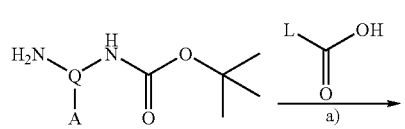

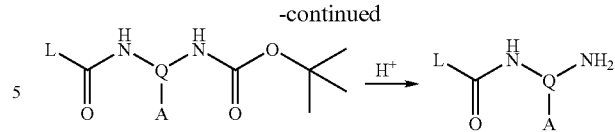

a) Coupling reagent whereby A, Q and L have the meaning that is indicated in general formula (I).

Diagram No. 8 for Synthesis of Anilines

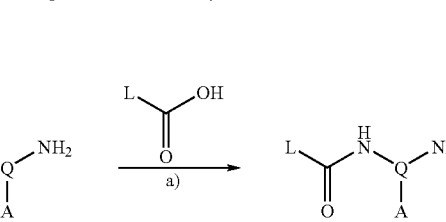

a) Coupling reagent whereby A, Q and L have the meaning that is indicated in general formula (I).

Diagram No. 9 for Synthesis of Anilines

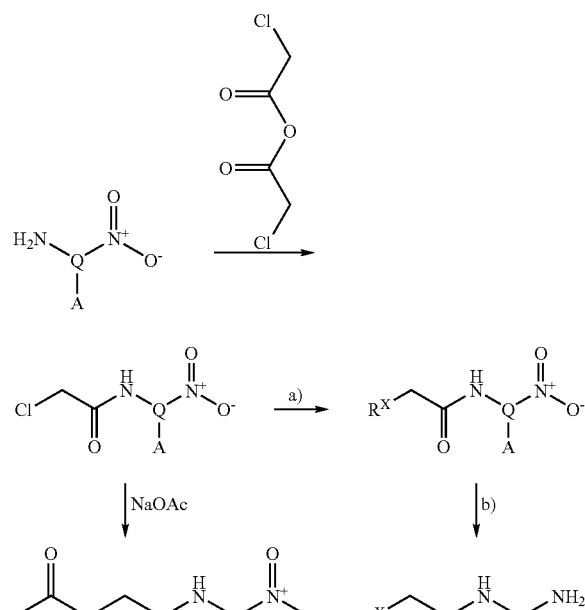

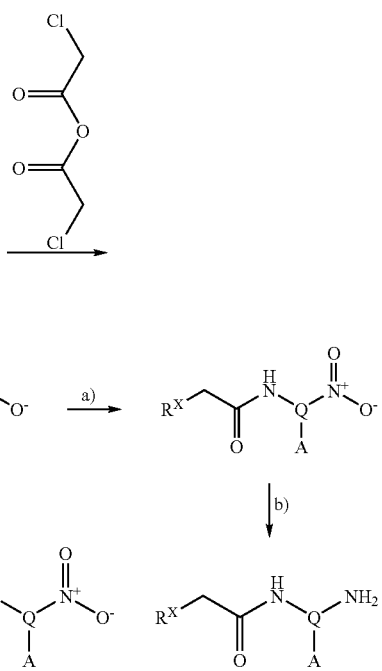

a) Substitution, b) Reduction whereby A, Q and $R^x$ have the meaning that is indicated in Synthesis Diagram 2.

Diagram No. 10 for Synthesis of Anilines

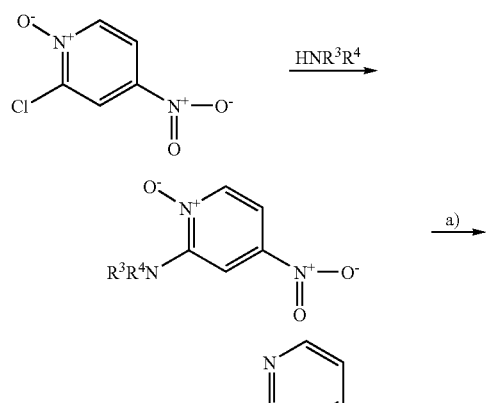

a) Reduction whereby $R^3$ and $R^4$ have the meaning that is indicated in general formula (I).

Diagram No. 11 for Synthesis of Anilines

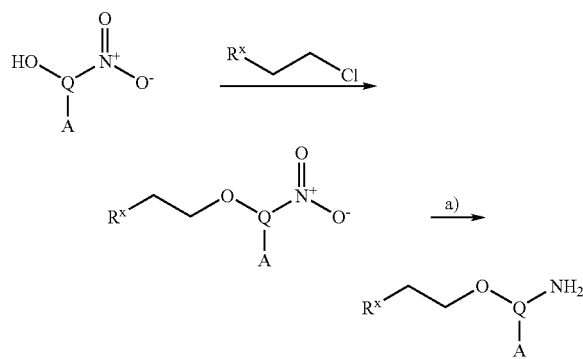

a) Reduction whereby A, Q and Rx have the meaning that is indicated in Synthesis Diagram 2.

Diagram No. 12 for Synthesis of Anilines

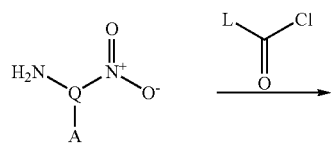

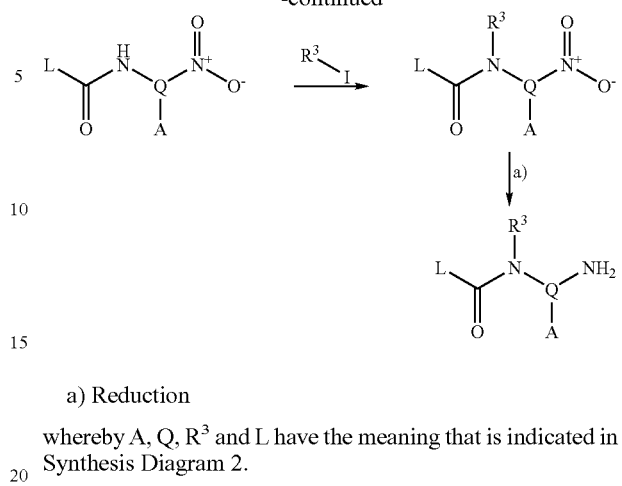

a) Reduction whereby A, Q, $R^3$ and L have the meaning that is indicated in Synthesis Diagram 2.

Diagram No. 13 for Synthesis of Anilines

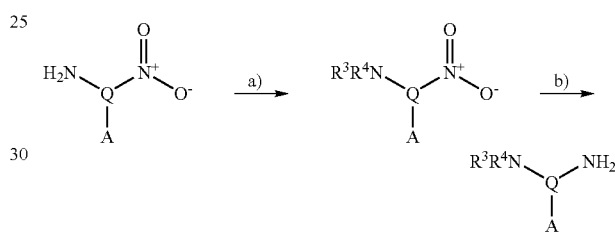

a) Reductive Amination; b) Reduction whereby A, Q, $R^3$ and $R^4$ have the meaning that is indicated in Synthesis Diagram 2, whereby $R^3$ or $R^4$=H.

Diagram No. 14 for Synthesis of Anilines

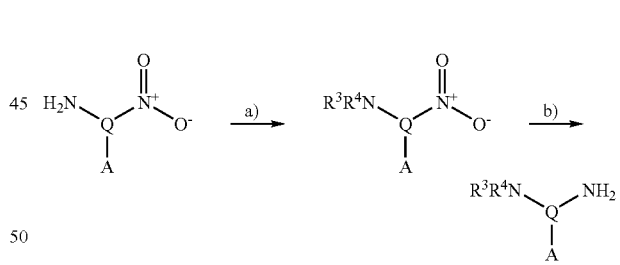

a) Substitution; b) Reduction whereby A, Q, $R^3$ and $R^4$ have the meaning that is indicated in Synthesis Diagram 2, whereby $R^3$ or $R^4$=H.

Diagram No. 15 for Synthesis of Anilines

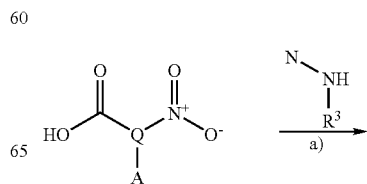

-continued

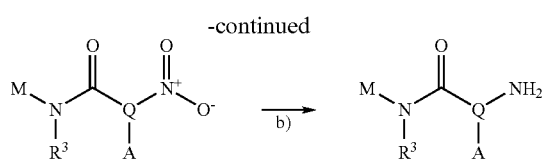

a) Coupling reagent; b) Reduction whereby A, Q, R³ and M have the meaning that is indicated in general formula (I).

SYNTHESIS OF INTERMEDIATE PRODUCTS

Intermediate Compound INT1

1-(2-Iodo-ethyl)-3-nitro-benzene

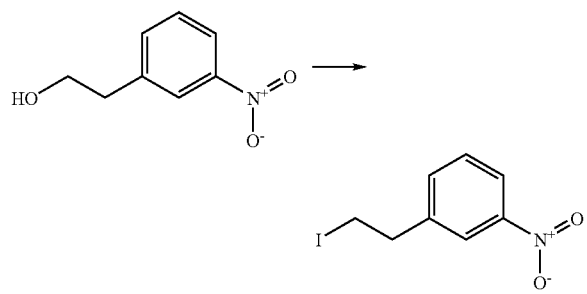

5 g of 3-nitrophenylethanol, 9.4 g of triphenylphosphine and 3.1 g of imidazole are dissolved in 250 ml of THF, mixed in portions with 9.1 g of iodine and stirred for 15 hours at room temperature. The reaction mixture is mixed with ammonium chloride solution and extracted with dichloromethane. The organic phase is washed in succession with sodium thiosulfate solution and water and dried on sodium sulfate. After purification by chromatography on silica gel, 7.51 g of the title compound is obtained.

1H-NMR (DMSO-d6): δ=3.31 (t, 2H); 3.41 (t, 2H); 7.46-7.60 (m, 2H); 8.09 (s, 1H); 8.16 (d, 1H); ppm.

Intermediate Compound INT2

1-[2-(3-Nitro-phenyl)-ethyl]-pyrrolidine

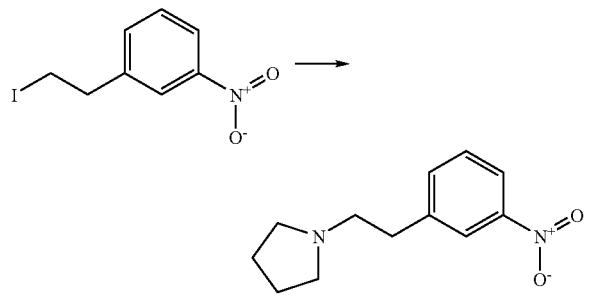

1.88 g of the compound that is described under Intermediate Compound INT1) is dissolved in 10 ml of dimethylformamide, mixed slowly with 0.85 ml of pyrrolidine and stirred for 15 hours at room temperature. The solvent is condensed under high vacuum, the residue is taken up in ethyl acetate and washed three times with water. The organic phase is dried on sodium sulfate. After purification by chromatography on silica gel, 350 mg of the title compound is obtained.

1H-NMR (CDCl3): δ=1.81 (m, 4H); 2.57 (m, 4H); 2.74 (t, 2H); 2.93 (t, 2H); 7.45 (t, 1H); 7.56 (d, 1H); 8.03-8.13 (m, 2H) ppm.

Intermediate Compound INT3

3-(2-Pyrrolidin-1-yl-ethyl)-phenylamine

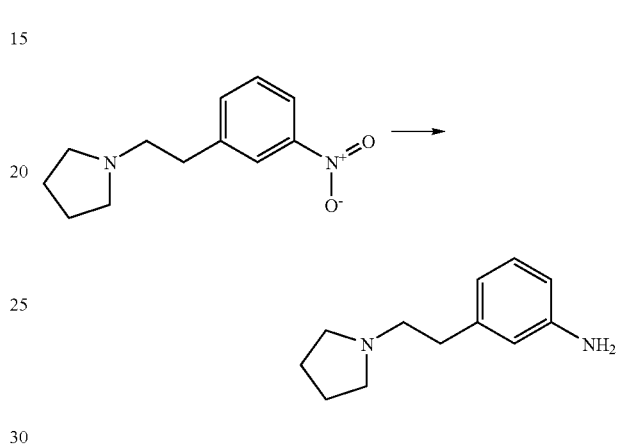

650 mg of the compound that is described under Intermediate Compound INT2) is dissolved in 250 ml of ethanol and mixed with 130 mg of palladium on carbon (10%). It is stirred for 15 hours under hydrogen atmosphere at room temperature. After filtration on diatomaceous earth is done and the solvent is condensed off in a rotary evaporator, 540 mg of the title compound is obtained.

1H-NMR (DMSO-d6): δ=1.78 (m, 4H); 2.65 (t, 2H); 2.70-2.92 (m, 6H); 4.99 (s, 2H); 6.31-6.45 (m, 3H); 6.92 (t, 1H) ppm.

Intermediate Compound INT4

1-(2-Iodo-ethyl)-4-nitro-benzene

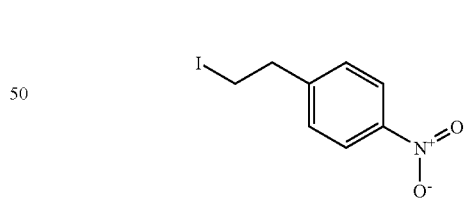

15 g of 4-nitrophenylethanol, 28.1 g of triphenylphosphine and 9.2 g of imidazole are dissolved in 500 ml of THF, mixed in portions with 27.77 g of iodine and stirred for 2 hours at room temperature. The reaction mixture is mixed with ammonium chloride solution and extracted with dichloromethane. The organic phase is washed in succession with sodium thiosulfate solution and water and dried on sodium sulfate. After purification by chromatography on silica gel, 23.22 g of the title compound is obtained.

1H-NMR (DMSO-d6): δ=3.30 (t, 2H); 3.54 (t, 2H); 7.57 (d, 2H); 8.18 (d, 2H) ppm.

Intermediate Compound INT5

1-[2-(4-Nitro-phenyl)-ethyl]-pyrrolidine

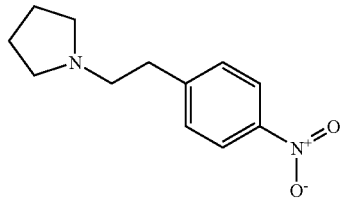

8 g of the compound that is described under Intermediate Compound INT4, 26.4 g of potassium carbonate and 3.6 ml of pyrrolidine are dissolved in 20 ml of dimethylformamide and stirred for 5 hours at room temperature. The solvent is condensed under high vacuum, the residue is taken up in ethyl acetate, and it is washed three times with water. The organic phase is dried on sodium sulfate. After purification by chromatography on silica gel, 5.6 g of the title compound is obtained.

1H-NMR (DMSO-d6): δ=1.68 (m, 4H); 2.48 (m, 4H); 2.67 (t, 2H); 2.89 (t, 2H); 7.52 (d, 2H); 8.13 (d, 2H) ppm.

Intermediate Compound INT6

4-(2-Pyrrolidin-1-yl-ethyl)-phenylamine

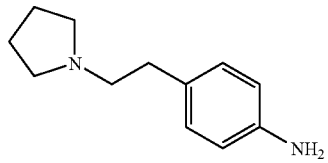

5.67 g of the compound that is described under Intermediate Compound INT5 is dissolved in 500 ml of ethanol and mixed with 1 g of palladium on carbon (10%). It is stirred for 2 hours under hydrogen atmosphere at room temperature. After filtration on diatomaceous earth is done and the solvent is condensed off in a rotary evaporator, 4.8 g of the title compound is obtained.

1H-NMR (DMSO-d6): δ=1.67 (m, 4H); 2.31-2.60 (m, 8H); 4.81 (s, 2H); 6.48 (d, 2H); 6.84 (d, 2H) ppm.

Intermediate Compound INT7

3-Nitro-N-(3-pyrrolidin-1-yl-propyl)-benzamide

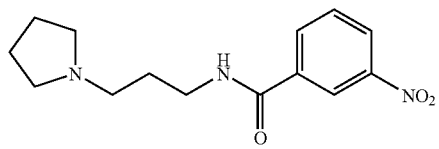

500 mg of 4-nitrobenzoic acid is dissolved in 20 ml of dimethylformamide, mixed with 370 μl of triethylamine, 342 mg of N-(3-aminopropyl)-pyrrolidine and 866 mg TBTU, and stirred for 20 hours at room temperature. The reaction mixture is mixed with semi-saturated sodium bicarbonate solution and extracted with dichloromethane. The organic solution is washed with saturated sodium chloride solution, dried on sodium sulfate, concentrated by evaporation, and after purification by chromatography on silica gel, 502 mg of the title compound is obtained.

1H-NMR (DMSO): δ=1.84 (m, 6H), 2.63 (m, 4H), 2.78 (m, 2H), 7.61 (m, 1H), 8.22 (dd, 1H), 8.32 (dd, 1H), 8.53 (m, 1H), 9.41 (s, 1H) ppm.

Intermediate Compound INT8

3-Amino-N-(3-pyrrolidin-1-yl-propyl)-benzamide

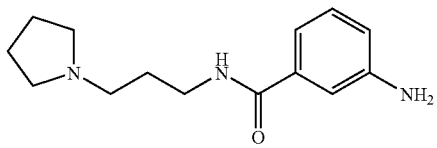

1 g of the compound that is described under Intermediate Compound INT7) is dissolved in 50 ml of THF and mixed with 1 g of Raney nickel. It is stirred for 3 hours under hydrogen atmosphere at room temperature. After filtration on diatomaceous earth is done and the solvent is condensed off in a rotary evaporator, 810 mg of the title compound is obtained.

1H-NMR (DMSO d6): δ=1.79 (m, 6H), 2.57 (m, 4H), 2.69 (m, 2H), 3.55 (m, 2H), 3.73 (s, 2H), 6.76 (dd, 1H), 7.02 (m, 1H), 7.17 (m, 2H), 8.52 (s, 1H) ppm.

Intermediate Compound INT9

N-(3-Amino-phenyl)-2,2-dimethyl-propionamide

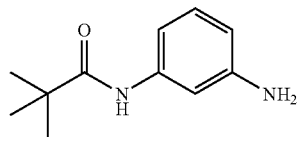

5.0 g of 1,3-diaminobenzene is dissolved in 50 ml of dichloromethane and mixed at 0° C. with 24 ml of diisopropylethylamine and 10.4 ml of pivalic acid anhydride. It is stirred for 2 hours at 0° C. and for 18 hours at room temperature. The reaction mixture is mixed with semi-saturated sodium bicarbonate solution and extracted with ethyl acetate. The organic solution is washed with saturated sodium chloride solution, dried on sodium sulfate, concentrated by evaporation, and after purification by chromatography on silica gel, 5.7 g of the title compound is obtained.

1H-NMR (DMSO-d6): δ=1.20 (s, 9H); 4.98 (s, 2H); 6.24 (d, 1H); 6.70 (d, 1H); 6.83-6.96 (m, 2H) ppm.

Intermediate Compound INT10

N-(3-Amino-5-chloro-phenyl)-2,2-dimethyl-propionamide

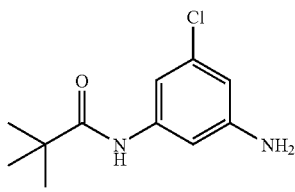

5.0 g of 5-chloro-1,3-diaminobenzene is dissolved in 50 ml of dichloromethane and 5 ml of dimethylformamide and mixed at 0° C. with 18.5 ml of diisopropylethylamine and 8.5 ml of pivalic acid anhydride. It is stirred for one hour at 0° C. and for 5 hours at room temperature. The reaction mixture is mixed with semi-saturated sodium bicarbonate solution and extracted with a mixture that consists of ethyl acetate and hexane (1:3). The organic solution is washed with saturated sodium chloride solution, dried on sodium sulfate, concentrated by evaporation, and after purification by chromatography on silica gel, 2.5 g of the title compound is obtained.

1H-NMR (DMSO-d6): (DMSO-d6): δ=5.37 (s, b, 2H); 6.28 (s, b, 1H); 6.88 (s, b, 1H); 7.48 (s, 1H); 9.00 (s, 1H) ppm.

Intermediate Compound INT11

1-(2-Iodo-ethyl)-3-nitro-benzene

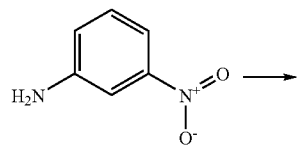

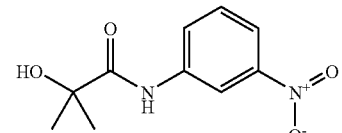

1.5 g of 2-hydroxy-2-methyl-propionic acid in 50 ml of dimethylacetamide is mixed at –10° C. with 1.05 ml of thionyl chloride and stirred for 30 minutes at –10° C. A solution of 2 g of 3-nitroaniline in 10 ml of dimethylacetamide is added in drops at –10° C. and stirred in succession for one hour at –10° C., for one hour at 0° C. and for 15 hours at room temperature. The solvent is condensed under high vacuum, the residue is taken up in a mixture that consists of ethyl acetate and dichloromethane (1:3) and washed twice with semi-saturated sodium bicarbonate solution. The organic phase is dried on sodium sulfate. After purification by chromatography on silica gel, 2.42 g of the title compound is obtained.

1H-NMR (CDCl3): δ=1.49 (s, 6H); 2.35 (s, 1H); 7.50 (t, 1H); 7.98 (d, 2H); 8.49 (s, 1H); 8.98 (s, b, 1H) ppm.

Intermediate Compound INT12

N-(3-Amino-phenyl)-2-hydroxy-2-methyl-propionamide

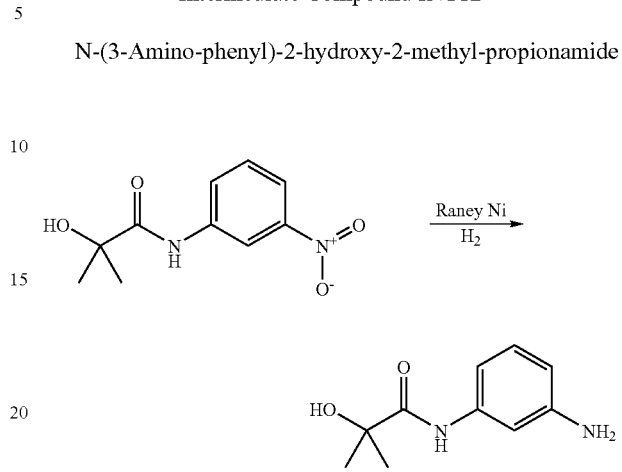

1.92 g of the compound that is described under Intermediate Compound INT11) is dissolved in 400 ml of ethanol and mixed with 50 mg of Raney nickel. It is stirred for 18 hours under hydrogen atmosphere at room temperature. After filtration on diatomaceous earth is done and the solvent is condensed off in a rotary evaporator, 1.9 g of the title compound is obtained.

1H-NMR (CDCl$_3$): δ=1.51 (s, 6H); 2.68 (s, 1H); 3.71 (s, b, 2H); 6.42 (d, 7.08 (t, 1H); 7.20 (s, 1H); 8.60 (s, b, 1H) ppm.

Intermediate Compound INT13

2-(2-Methoxy-ethoxy)-N-(3-nitro-phenyl)-acetamide

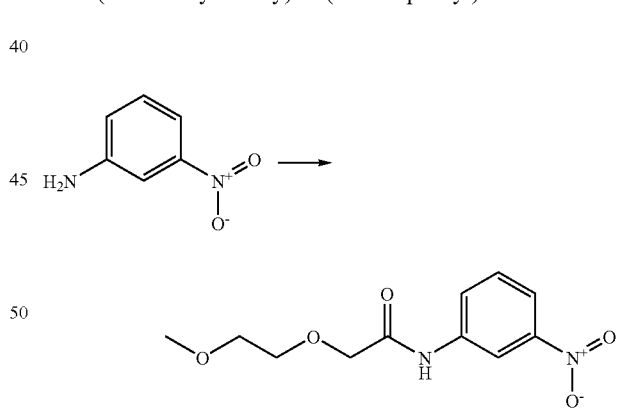

5 g of (2-methoxyethoxy)-acetic acid is dissolved in 500 ml of tetrahydrofuran. 9.7 ml of triethylamine and 5.6 ml of isobutyl chloroformate are added at 0° C., and it is stirred for 30 minutes at 0° C. 5.0 g of 3-nitroaniline is added, and it is stirred for another 15 hours at room temperature. The reaction mixture is mixed with semi-saturated sodium bicarbonate solution and extracted with ethyl acetate. The organic solution is washed with saturated sodium chloride solution, dried on sodium sulfate, concentrated by evaporation and, after purification by chromatography on silica gel, 7.5 g of the title compound is obtained.

1H-NMR (DMSO-d6): δ=3.30 (s, 3H); 3.53 (m, 2H); 3.70 (m, 2H); 4.04 (s, 1H); 7.62 (t, 1H); 7.93 (d, 1H); 8.02 (d, 1H); 8.69 (s, 1H); 10.20 (s, b, 1H) ppm.

Intermediate Compound INT14

N-(3-Amino-phenyl)-2-(2-methoxy-ethoxy)-acetamide

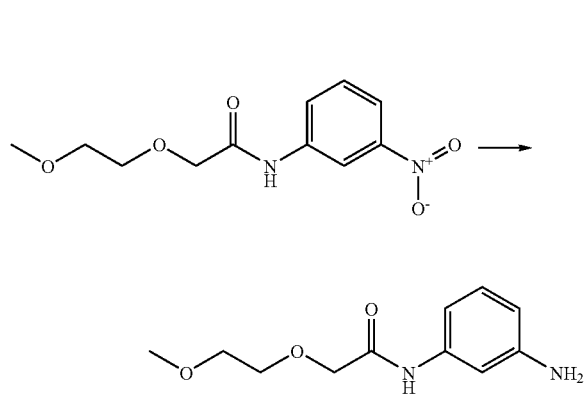

7.5 g of the compound described under Intermediate Compound INT13) is dissolved in 150 ml of ethanol and mixed with 1.3 g of palladium on carbon (10%). It is stirred for 15 hours under hydrogen atmosphere at room temperature. After filtration on diatomaceous earth is done and the solvent is condensed off in a rotary evaporator, 6.5 g of the title compound is obtained.

1H-NMR (DMSO-d6): δ=3.31 (s, 3H); 3.51 (m, 2H); 3.65 (m, 2H); 4.02 (s, 2H); 6.10 (s, 2H); 6.28 (d, 1H); 6.70 (d, 1H); 6.87-6.98 (m, 2H); 9.27 (s, 1H) ppm.

Intermediate Compound INT15

N-(6-Amino-pyridin-2-yl)-2,2-dimethyl-propionamide

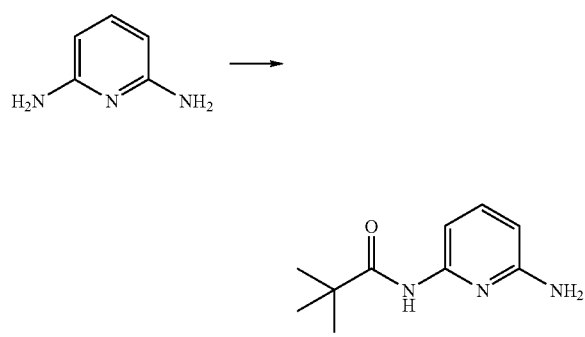

10 g of 2,6-diaminopyridine is dissolved in 150 ml of tetrahydrofuran. 48 ml of diisopropylethylamine and 20.8 ml of pivalic acid anhydride are added, and it is stirred for 15 hours at room temperature. The solvent is condensed in a rotary evaporator. After purification by chromatography on silica gel, 10.6 g of the title compound is obtained.

1H-NMR (DMSO-d6): δ=1.20 (s, 9H); 5.72 (s, 2H); 6.07 (d, 1H); 7.18 (d, 1H); 7.33 (t, 1H); 8.93 (s, 1H) ppm.

Intermediate Compound INT16

N-(6-Amino-pyridin-2-yl)-2-(2-methoxy-ethoxy)-acetamide

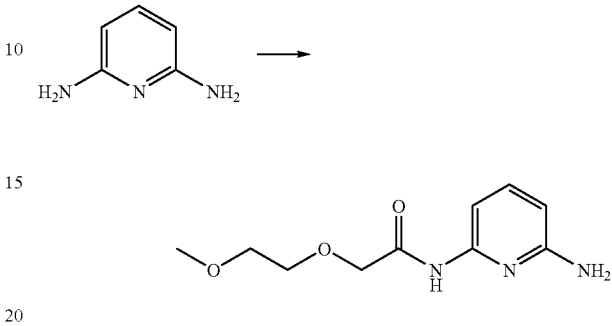

4.9 ml of (2-methoxyethoxy)-acetic acid is dissolved in 500 ml of tetrahydrofuran. 9.7 ml of triethylamine and 5.6 ml of isobutyl chloroformate are added at 0° C., and it is stirred for 30 minutes at 0° C. 3.96 g of 2,6-diaminopyridine is added, and it is stirred for another 4 hours at room temperature. The reaction mixture is mixed with semi-saturated sodium bicarbonate solution and extracted with ethyl acetate. The organic solution is washed with saturated sodium chloride solution, dried on sodium sulfate, concentrated by evaporation, and after purification by chromatography on silica gel, 5.04 g of the title compound is obtained.

1H-NMR (DMSO-d6): δ=3.31 (s, 3H); 3.50 (m, 2H); 3.67 (m, 2H); 4.07 (s, 2H); 5.88 (s, 2H); 6.19 (d, 1H); 7.21 (d, 1H); 7.36 (t, 1H); 9.13 (s, 1H) ppm.

Intermediate Compound INT17

Ethyl-(4-nitro-1-oxy-pyridin-2-yl)-amine

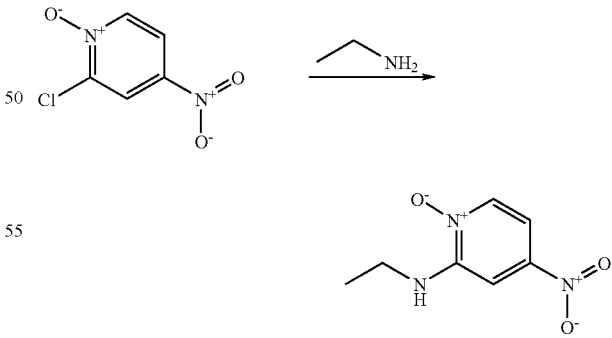

2.0 g of 2-chloro-4-nitro-pyridine 1-oxide is dissolved in 20 ml of ethanol. 11.5 ml of triethylamine is added, and it is stirred under reflux for 4 hours. The solvent is condensed in a rotary evaporator. After purification by chromatography on silica gel, 1.5 g of the title compound is obtained.

1H-NMR (DMSO-d6): δ=1.19 (t, 3H); 3.39 (pentuplet, 2H); 7.39 (dd, 1H); 7.47 (d, 1H); 7.64 (t, 1H); 8.35 (d, 1H) ppm.

Intermediate Compound INT18

4-Amino-2-ethylamino-pyridine

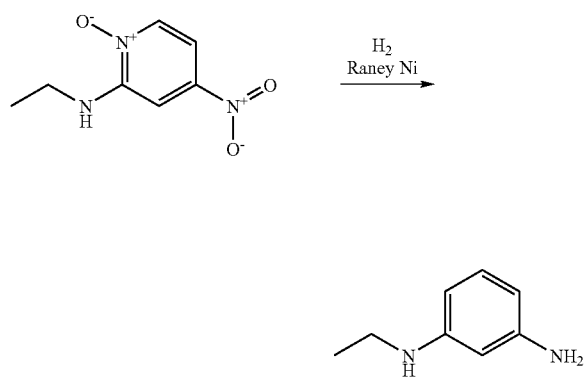

800 mg of the compound that is described under Intermediate Compound INT17) is dissolved in 50 ml of ethanol and mixed with 50 mg of Raney nickel. It is hydrogenated for 5 hours under a 3.5 bar hydrogen atmosphere at room temperature. After filtration on diatomaceous earth is done and the solvent is condensed off in a rotary evaporator, 610 mg of the title compound is obtained.

1H-NMR (DMSO-d6): δ=1.09 (t, 3H); 3.11 (m, 2H); 5.48 (s, 2H); 5.52 (d, 1H); 5.71 (t, 1H); 5.78 (dd, 1H); 7.49 (d, 1H) ppm.

Intermediate Compound INT19

2-(3-Nitro-phenyl)-oxirane

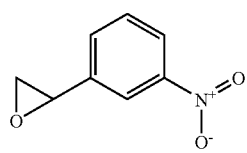

10 g of 2-bromo-1-(3-nitro-phenyl)-ethanone is dissolved in 200 ml of ethanol, mixed with 1.55 g of sodium borohydride and stirred for 1 hour at room temperature. 2.1 g of potassium hydroxide is added, and it is stirred for another 15 hours at room temperature. 1000 ml of ethyl acetate is added, and it is washed twice with 300 ml of semi-saturated ammonium chloride solution and once with 100 ml of water. The organic phase is dried on sodium sulfate. After purification by chromatography on silica gel, 7.48 g of the title compound is obtained.

$^1$H NMR (CDl$_3$):

δ=2.79 (dd, 1H); 3.19 (dd, 1H); 3.93 (dd, 1H); 7.50 (t, 1H); 7.60 (d, 1H); 8.08-8.16 (m, 2H) ppm.

Intermediate Compound INT20

1-(3-Nitro-phenyl)-2-(4aR,8aS)-decahydro-isoquinolin-2-yl-ethanol (Diastereomer Mixture)

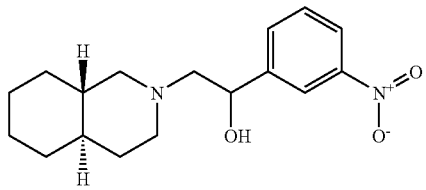

5.0 g of the compound that is described under INT19 is dissolved in 50 ml of tetrahydrofuran and mixed with 7.3 g of trans-decahydroisoquinoline and stirred for 20 hours under reflux. The solvent is distilled off in a rotary evaporator, and after purification by chromatography on silica gel, 5.75 g of the title compound is obtained.

$^1$H NMR (CDCl$_3$):

δ=0.72-1.45 (m, 7H); 1.45-1.85 (m, 6H); 1.95-3.20 (m, 5H); 4.43 (b, 1H); 4.75-4.86 (m, 1H); 7.51 (t, 1H); 7.72 (d, 1H); 8.13 (d, 1H); 8.25 (s, 1H) ppm.

Intermediate Compound INT21

Acetic Acid (4aR,8aS)-1-(3-nitro-phenyl)-2-decahydro-isoquinolin-2-yl-ethyl Ester

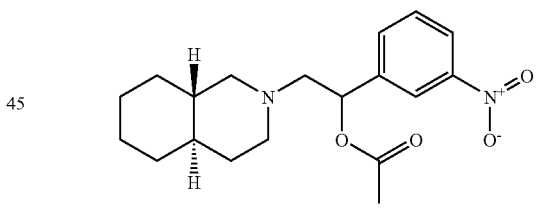

5.75 g of the compound that is described under INT20 is dissolved in 100 ml of tetrahydrofuran and mixed at 0° C. with 5.4 ml of triethylamine and 3.6 ml of acetic anhydride and then stirred for 48 hours at room temperature. Half of the solvent is distilled off in a rotary evaporator, 100 ml of semi-saturated sodium bicarbonate solution is added, and it is extracted three times with 150 ml of dichloromethane each. The combined organic phases are dried on sodium sulfate. After purification by chromatography on silica gel and subsequent recrystallization, 4.07 g of the title compound is obtained.

$^1$H NMR (CDCl$_3$; main isomer):

δ=0.72-1.05 (m, 3H); 1.06-1.35 (m, 4H); 1.40-1.89 (m, 6H); 2.00-2.22 (m, 4H); 2.55 (dd, 1H); 2.64-2.96 (m, 3H); 5.97 (dd, 1H); 7.51 (t, 1H); 7.68 (d, 1H); 8.14 (d, 1H); 8.22 (s, 1H) ppm.

Intermediate Compound INT22

3-[(4aR,8aS)-2-(Decahydro-isoquinolin-2-yl)-ethyl]-phenylamine

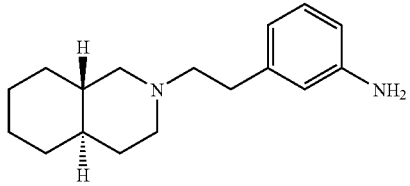

4.07 g of the compound that is described under INT21) is dissolved in 400 ml of ethyl acetate and 100 ml of glacial acetic acid, and it is mixed with 400 mg of palladium on carbon (10%). It is hydrogenated for 15 hours under 100 bar of hydrogen at room temperature. Another 1000 mg of palladium on carbon (10%) is added, and it is hydrogenated for another 15 hours under 100 bar of hydrogen at room temperature. Half of the solvent is distilled off in a rotary evaporator, and about 1 l of 2N sodium hydroxide solution is added until the solution has a pH of 9.5. The solution is extracted in succession with 300 ml of ethyl acetate and with 500 ml of a mixture that consists of chloroform and methanol (10:1). The combined organic phases are washed with water (100 ml) and saturated common salt solution (100 ml) and dried on sodium sulfate. After the solvent is filtered and condensed off in a rotary evaporator, 2.57 g of the title compound is obtained.

$^1$H NMR (CDCl$_3$):

δ=0.69-1.03 (m, 3H); 1.03-1.33 (m, 4H); 1.39-1.73 (m, 6H); 1.86-2.00 (m, 1H); 2.41-2.53 (m, 2H); 2.61-2.71 (m, 2H); 2.75-2.83 (m, 1H); 2.88-3.00 (m, 1H); 3.37-3.70 (b, 2H); 6.40-6.50 (m, 2H); 6.54 (d, 1H); 7.00 (t, 1H) ppm.

Intermediate Compound INT23

2-Chloro-N-(3-nitro-phenyl)-acetamide

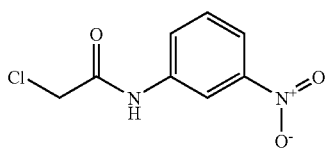

13.8 g of 3-nitroaniline is dissolved in 500 ml of tetrahydrofuran. 30.5 ml of triethylamine and 19.4 g of chloroformic acid anhydride are added at 0° C. It is stirred for 12 hours at room temperature. The reaction mixture is mixed with semi-saturated sodium bicarbonate solution and extracted with ethyl acetate. The organic solution is washed with saturated sodium chloride solution, dried on sodium sulfate, concentrated by evaporation and after purification by chromatography on silica gel, 20.0 g of the title compound is obtained.

1H-NMR (DMSO-d6): δ=4.31 (s, 2H); 7.64 (t, 1H); 7.89-8.00 (m, 2H); 8.61 (s, 1H); 10.79 (b, 1H) ppm.

Intermediate Compound INT24

N-(3-Nitro-phenyl)-2-piperidin-1-yl-acetamide

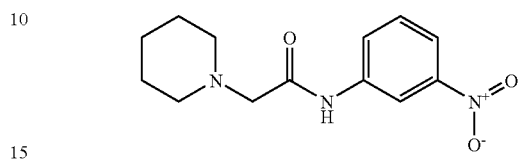

2.14 g of the compound that is described under Intermediate Compound INT23) is dissolved in 100 ml of dimethylformamide. 2.0 ml of triethylamine, 248 mg of potassium iodide, and 1.48 ml of piperidine are added. It is stirred for 4 hours at room temperature. The reaction mixture is mixed with semi-saturated sodium bicarbonate solution and extracted with ethyl acetate. The organic solution is washed with saturated sodium chloride solution, dried on sodium sulfate, concentrated by evaporation, and after purification by chromatography on silica gel, 1.97 g of the title compound is obtained.

1H-NMR (DMSO-d6): δ=1.34-1.48 (m, 2H); 1.51-1.63 (m, 4H); 2.45 (m, 4H); 3.12 (s, 2H); 7.60 (t, 1H); 7.91 (d, 1H); 8.02 (d, IH); 8.70 (s, 1H); 10.18 (s, 1H) ppm.

Intermediate Compound INT25

(1-Methyl-1H-benzimidazol-2-yl)-acetonitrile

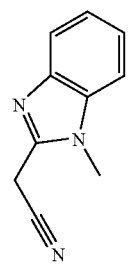

Methyl iodide (1.24 ml, 19.19 mmol) is added to a solution of (1H-benzoimidazol-2-yl)-acetonitrile (3.13 g, 19.91 mmol) and potassium carbonate (2.75 g, 19.91 mmol) in 20 ml of dimethylformamide. It is stirred for 24 hours at room temperature, and additional potassium carbonate (2.8 g, 20.27 mmol) and additional methyl iodide (1.3 ml, 20.12 mmol) are added. It is stirred for another 24 hours at room temperature, water and methanol are added, and the solvent is distilled off in a vacuum. The residue is mixed with 200 ml of water and extracted three times in succession with 200 ml each of dichloromethane. The combined organic phases are dried on sodium sulfate, concentrated by evaporation, and after purification by chromatography on silica gel, 502 mg of the title compound is obtained.

$^1$H NMR (DMSO-d6): δ=3.75 (s, 3H); 4.52 (s, 2H); 7.23 (m, 2H); 7.54 (d, 1H); 7.62 (d, 1H) ppm.

The compounds below are produced analogously to the above-described process.

TABLE 1

Aniline Intermediate Compound

| Intermediate Compound No. | Structure and Name | 1H-NMR | Molecular Weight// MS (ESI) [M + 1]+ | Educt/ Synthesis Analogous to |
|---|---|---|---|---|
| INT26 | 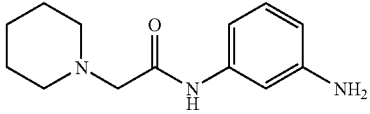<br>N-(3-Amino-phenyl)-2-piperidin-1-yl-acetamide | (DMSO-d6): δ = <br>1.45(m, 2H);<br>1.65(m, 4H);<br>2.78(m, 4H);<br>3.45(s, 2H);<br>4.70-6.00(b, 2H);<br>6.29(d, 1H);<br>6.72(d, 1H);<br>6.88-7.00(m, 2H);<br>9.80(s, 1H) ppm. | | INT20/ INT3 |

SYNTHESIS OF ADDITIONAL INTERMEDIATE PRODUCTS

Intermediate Compound INTT1)

Cyano-ethylthiocarbamoyl-acetic Acid Ethyl Ester

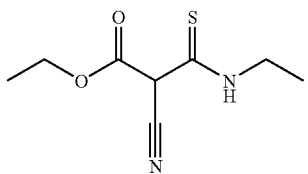

4.25 ml of ethyl isothiocyanate is added to a mixture that consists of 5 g of cyanoacetic acid ethyl ester and 5 ml of triethylamine at 25° C. Then, it is allowed to stir for 6 more hours at 50° C. Then, the reaction mixture is concentrated by evaporation in a vacuum. The residue is taken up in ethanol and poured into 150 ml of ice-cold IN hydrochloric acid. It is allowed to stir for 3 more hours at 25° C., and then the residue is filtered off. The solid that is obtained is rewashed with water. 7 g of product is obtained.

Molar Mass =200.261; MS (ESI): [M+1]+=201.

Intermediate Compound INTT2)

(E or Z)-Cyano-(3-ethyl-4-oxo-thiazolidin-2-ylidene)-acetic acid ethyl ester

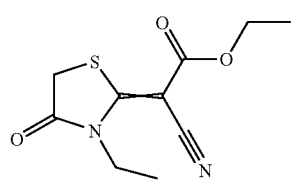

7.82 g of the compound that is described under Intermediate Compound INTT1) is dissolved in 100 ml of tetrahydrofuran. A solution of 3.9 ml of bromoacetyl chloride is slowly added and allowed to stir for 8 more hours at 25° C. Then, the reaction mixture is poured into saturated aqueous sodium bicarbonate solution. It is allowed to stir for 1 more hour and then extracted with ethyl acetate. The organic phase is washed with saturated sodium chloride solution, dried on sodium sulfate, and concentrated by evaporation in a vacuum. The crude product that is obtained is recrystallized from a mixture of ethyl acetate/diisopropyl ester. 7.7 g of product is obtained.

1H-NMR (CDCl3): δ=1.36 (6H); 3.70 (2H); 4.32 (4H) ppm.

Intermediate Compound INTT3)

(E or Z)-Cyano-(5-(E/Z)-ethoxymethylene-3-ethyl-4-oxo-thiazolidin-2-ylidene)-acetic acid ethyl ester

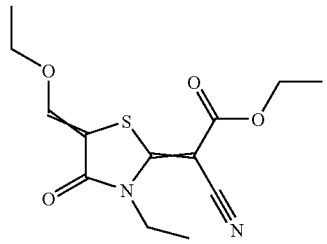

A mixture that consists of 1.54 g of the substance that is described under Intermediate Compound INTT2), 2.5 ml of triethyl orthoformate and 3.5 ml of acetic acid anhydride are refluxed for 8 hours. Then, the reaction mixture is poured into ice water. It is allowed to stir for 3 more hours, and then the residue is filtered off. The solid that is obtained is rewashed with water. 1.28 g of product is obtained.

1H-NMR (CDCl3): δ=1.38 (9H); 4.20-4.40 (6H); 7.72 (1H) ppm.

Intermediate Compound INTT4)

(E or Z)-Cyano-(3-ethyl-4-oxo-thiazolidin-2-ylidene)-acetic acid allyl ester

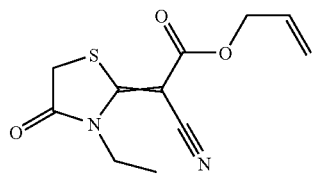

A solution of 37.6 ml of cyanoacetic acid allyl ester in 60 ml of dimethylformamide is added to a suspension of 12.8 g of sodium hydride (60%) in 200 ml of dimethylformamide at 0° C. It is stirred for 10 more minutes at 0° C., and then a solution of 28.0 ml of ethyl isothiocyanate in 60 ml of dimethylformamide is added. It is then stirred for 2 more hours at 25° C. Then, a solution of 32 ml of bromoacetyl chloride in 60 ml of dimethylformamide is added at 0° C., and it is stirred for 15 more hours at 25° C. Then, the reaction mixture is poured into saturated sodium bicarbonate solution. It is extracted with ethyl acetate, the organic phase is washed with saturated sodium chloride solution, dried on sodium sulfate and concentrated by evaporation in a vacuum. The crude product is purified by column chromatography on silica gel with a mixture that consists of hexane/ethyl acetate. 33.9 g of product is obtained.

1H-NMR (CDCl3): $\delta$=1.23 (3H); 4.11 (2H); 4.71 (2H); 5.25 (1H); 5.37 (1H); 5.90-6.04 (1H) ppm.

Intermediate Compound INTT5)

(E or Z)-Cyano-(5-(E/Z)-ethoxymethylene-3-ethyl-4-oxo-thiazolidin-2-ylidene)-acetic acid allyl ester

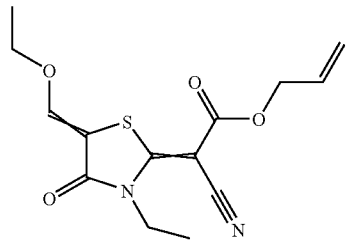

Analogously to Intermediate Compound INTT3), 14.8 g of product is obtained from 12.8 g of the compound that is described under Intermediate Compound INTT4), 20.9 ml of triethyl orthoformate and 29.4 ml of acetic acid anhydride.

1H-NMR (CDCl3): $\delta$=1.32-1.45 (6H); 4.23 (2H); 4.38 (2H); 4.73 (2H); 5.29 (1H); 5.41 (1H); 5.92-6.05 (1H); 7.72 (1H) ppm.

Intermediate Compound INTT6)

[3-Ethyl-4-oxo-thiazolidin-(2-(E or Z))-ylidene]-pyridin-2-yl-acetonitrile

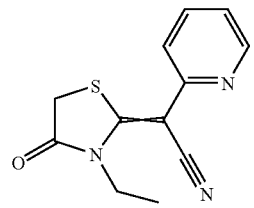

Sodium hydride (60% in oil; 0.73 g, 18.25 mmol) is added to 10 ml of dimethylformamide at 0° C. and under nitrogen-inert gas atmosphere. 2-Pyridylacetonitrile (2 ml, 17.93 mmol), dissolved in 30 ml of dimethylformamide, is added drop by drop within five minutes. It is stirred for 10 minutes, and then a solution of ethyl isothiocyanate (1.6 ml, 18.36 mmol) in 10 ml of dimethylformamide is added drop by drop within 5 minutes. The solution is stirred for two hours at room temperature, cooled again to 0° C., and then a solution of bromoacetyl chloride (2.3 ml, 27.59 mmol) in 10 ml of dimethylformamide is added drop by drop. It is stirred overnight at room temperature, the reaction mixture is poured into 300 ml of cold, saturated sodium bicarbonate solution, and extracted three times in succession with 300 ml each of ethyl acetate. The combined organic phases are washed with 900 ml of saturated common salt solution, dried on sodium sulfate, concentrated by evaporation, and after purification by chromatography on silica gel, 1.83 g of the title compound is obtained.

$^1$H NMR (DMSO-d6, main isomer): $\delta$=1.28 (t, 3H); 3.84 (s, 2H); 4.22 (q, 2H); 7.27 (dd, 1H); 7.61 (d, 1H); 7.90 (t, 1H); 8.58 (d, 1H) ppm.

The compounds below are produced analogously to the above-described process.

TABLE 2

| | | | | |
|---|---|---|---|---|
| | Intermediate Compounds | | | |
| Example No. | Structure and Name | $^1$H-NMR | Molecular Weight// MS (ESI) [M + 1]$^+$ | Educt/ Synthesis analogously to |
| INTT7 | | (DMSO-d6, Main Isomer): $\delta$ = 1.28(t, 3H); | MW: 245.30 | Commercial |

TABLE 2-continued

Intermediate Compounds

| Example No. | Structure and Name | ¹H-NMR | Molecular Weight// MS (ESI) [M + 1]⁺ | Educt/ Synthesis analogously to |
|---|---|---|---|---|
| | [3-Ethyl-4-oxo-thiazolidin-(2-(E or Z))-ylidene]-pyridin-3-yl-acetonitrile | 3.97(s, 2H); 4.09(q, 2H); 7.50(dd, 1H); 7.86(d, 1H); 8.59(dd, 1H); 8.62(d, 1H) ppm. | MS (ES+) [M + 1]+: 246 | INTT6 |
| INTT8 | [3-Ethyl-4-oxo-thiazolidin-(2-(E or Z))-ylidene]-pyridin-4-yl-acetonitrile | (DMSO-d6, Main Isomer): δ = 1.28(t, 3H); 4.02(s, 2H); 4.11(q, 2H); 7.49(d, 2H); 8.66(d, 2H) ppm. | MW: 245.30<br><br>MS (ES+) [M + 1]+: 246 | Commercial<br><br>INTT6 |
| INTT9 | [3-Ethyl-4-oxo-thiazolidin-(2-(E or Z))-ylidene]-thiophen-2-yl-acetonitrile | (DMSO-d6, Main Isomer): δ = 1.26(t, 3H); 4.00(s, 2H); 4.09(q, 2H); 7.13(t, 1H); 7.21(d, 1H); 7.69(d, 1H) ppm. | MW: 250.34<br><br>MS (ES+) [M + 1]+: 251 | Commercial<br><br>INTT6 |
| INTT10 | [3-Ethyl-4-oxo-thiazolidin-(2-(E or Z))-ylidene]-thiophen-3-yl-acetonitrile | (DMSO-d6, Main Isomer): δ = 1.26(t, 3H); 3.97(s, 2H); 4.09(q, 2H); 7.19(t, 1H); 7.68(d, 2H) ppm. | MW: 250.34<br><br>MS (ES+) [M + 1]+: 251 | Commercial<br><br>INTT6 |
| INTT11 | Benzo[b]thiophen-3-yl-[3-ethyl-4-oxo-thiazolidin-(2-(E or Z))-ylidene]-acetonitrile | | MW: 300.40<br><br>MS (ES+) [M + 1]+: 301 | Commercial<br><br>INTT6 |

TABLE 2-continued

Intermediate Compounds

| Example No. | Structure and Name | ¹H-NMR | Molecular Weight// MS (ESI) [M + 1]⁺ | Educt/ Synthesis analogously to |
|---|---|---|---|---|
| INTT12 | [3-Ethyl-4-oxo-thiazolidin-(2-(E or Z))-ylidene]-(1-methyl-1H-benzoimidazol-2-yl)-acetonitrile | | MW: 298.37  MS (ES+) [M + 1]+: 299 | INT25 INTT6 |
| INTT13 | Benzothiazol-2-yl-[3-ethyl-4-oxo-thiazolidin-(2-(E or Z))-ylidene] acetonitrile | (DMSO-d6, Main Isomer): δ = 1.29(t, 3H); 4.04(s, 2H); 4.19(q, 2H); 7.42(t, 1H); 7.52(t, 1H); 7.91(d, 1H); 8.11(d, 1H) ppm. | | Commercial  INTT6 |
| INTT14 | 3-Ethyl-4-oxo-thiazolidin-(2-(E or Z))-ylidene]-(4-methyl-thiazol-2-yl)-acetonitrile | (DMSO-d6, Main Isomer): δ = 1.28(t, 3H); 2.37(s, 3H); 3.96(s, 2H); 4.13(q, 2H); 7.24(s, 1H) ppm. | | Commercial  INTT6 |
| INTT15 | [3-Ethyl-4-oxo-thiazolidin-(2-(E or Z))-ylidene]-(1-methyl-1H-pyrrol-2-yl)-acetonitrile | | MW: 247.32  MS (ES+) [M + 1]+: 248 | Commercial  INTT6 |

SYNTHESIS OF ADDITIONAL INTERMEDIATE PRODUCTS

Intermediate Compound INTE1

Cyano-[3-ethyl-4-oxo-5-[1-[3-(2-pyrrolidin-1-yl-ethyl)-phenylamino]-meth-(E/Z)-ylidene]-thiazolidin-(2-(E or Z))-ylidene]-acetic acid ethyl ester

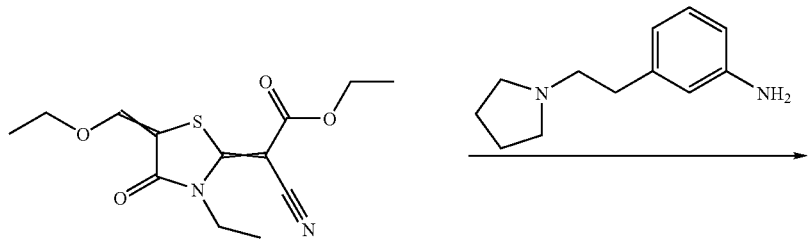

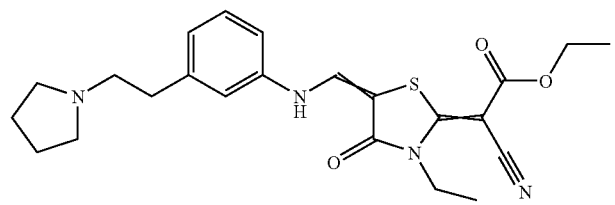

740 mg of the compound that is described under Intermediate Compound INT3) is dissolved in 50 ml of ethanol. 1.1 g of the compound that is described under Intermediate Compound INTT3) is added, and it is stirred for 5 hours under reflux. The solvent is condensed in a rotary evaporator. After purification by chromatography on silica gel, 540 mg of the title compound is obtained as a pH-dependent 5-(E/Z)-isomer mixture.

1H-NMR (CDCl3, main isomer): δ=1.38 (t, 3H); 1.42 (t, 3H); 1.83 (m, 4H); 2.60 (m, 4H); 2.72 (m, 2H); 2.86 (m, 2H); 4.31 (q, 2H); 4.43 (q, 2H); 6.87-6.97 (m, 2H); 7.00 (d, 1H); 7.29 (t, 1H); 7.62 (d, 1H); 10.56 (d, 1H) ppm.

Intermediate Compound INTE2

Cyano-[3-ethyl-4-oxo-5-[1-[3-(2-pyrrolidin-1-yl-ethyl)-phenylamino]-meth-(E/Z)-ylidene]-thiazolidin-(2-(E or Z))-ylidene]-acetic acid allyl ester

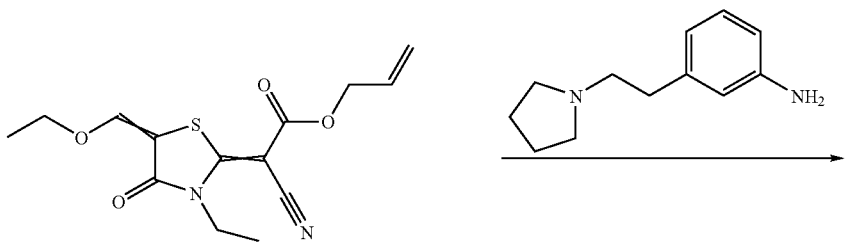

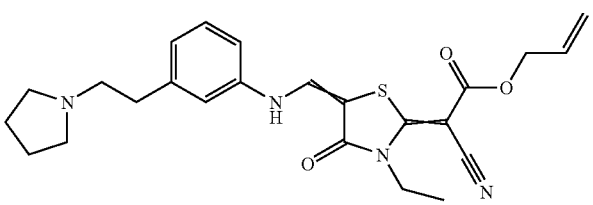

1.35 g of the compound that is described under Intermediate Compound INT3) is dissolved in 400 ml of ethanol. 2.19 g of the compound that is described under Intermediate Compound INTT5) is added, and it is stirred for 4 hours under reflux. The solvent is condensed in a rotary evaporator. After purification by chromatography on silica gel, 2.2 g of the title compound is obtained as a pH-dependent 5-(E/Z)-isomer mixture.

1H-NMR (DMSO-d6, stored with $K_2CO_3$, main isomer): δ=1.24 (t, 3H); 1.69 (m, 4H); 2.50 (m, 4H); 2.66 (m, 2H); 2.76 (m, 2H); 4.25 (q, 2H); 4.71 (d, 2H); 5.26 (d, 1H); 5.38 (d, 1H); 5.90-6.08 (m, 1H); 6.96 (d, 1H); 7.12 (d, 1H); 7.22 (s, 1H); 7.26 (t, 1H); 8.22 (s, 1H); 10.53 (s, b, 1H) ppm.

Intermediate Compound INTE3

Cyano-[3-ethyl-5-[1-[3-(2-hydroxy-2-methyl-propionylamino)-phenylamino]-meth-(E/Z)-ylidene]-4-oxo-thiazolidin-(2-(E or Z))-ylidene]-acetic acid allyl ester

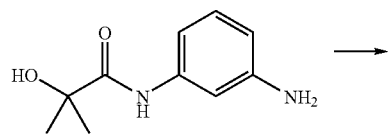

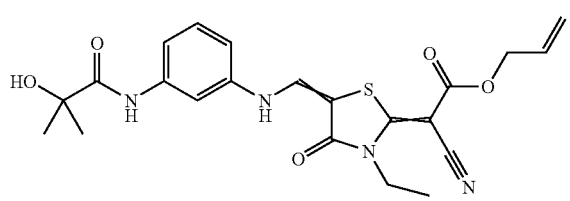

1.26 g of the compound that is described under Intermediate Compound INT12) is dissolved in 400 ml of ethanol. 2.0 g of the compound that is described under Intermediate Compound INTT5) is added, and it is stirred under reflux for 6 hours. After cooling, the reaction mixture is filtered, and the solid that is obtained is recrystallized from ethanol. 1.4 g of the title compound is obtained as a pH-dependent 5-(E/Z)-isomer mixture. The solution that is obtained with the filtration is concentrated by evaporation in a rotary evaporator. After purification by chromatography on silica gel, the residue produces another 1.1 g of the title compound as a pH-dependent 5-(E/Z)-isomer mixture.

1H-NMR (DMSO-d6, stored with K2CO3, main isomer): δ=1.28 (t, 3H); 1.38 (s, 6H); 4.26 (q, 2H); 4.72 (d, 2H); 5.27 (d, 1H); 5.39 (d, 1H); 5.76 (s, 1H); 5.90-6.08 (m, 1H); 6.99 (d, 1H); 7.27 (t, 1H); 7.46 (d, 1H); 7.89 (s, 1H); 8.16 (s, 1H); 9.67 (s, 1H); 10.63 (s, 1H) ppm.

Intermediate Compound INTE4

Cyano-[3-ethyl-5-[1-(2-ethylamino-pyridin-4-ylamino)-meth-(E/Z)-ylidene]-4-oxo-thiazolidin-(2-(E or Z))-ylidene]-acetic acid allyl ester

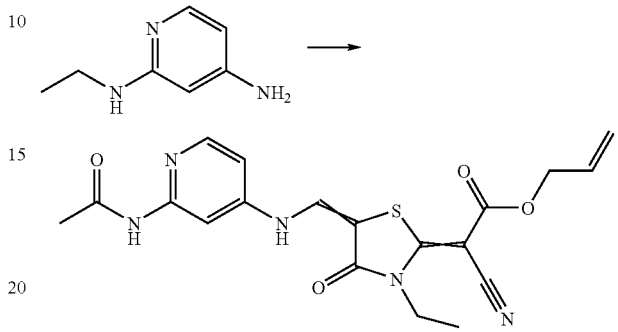

0.94 g of the compound that is described under Intermediate Compound INT18) is dissolved in 50 ml of 1-propanol. 1.85 g of the compound that is described under Intermediate Compound INTT5) is added, and it is stirred for 4 hours under reflux. After cooling, the reaction mixture is filtered. After purification by chromatography on silica gel, the solid that is obtained yields 1.48 g of the title compound as a pH-dependent 5-(E/Z)-isomer mixture.

1H-NM (DMSO-d6, stored with $K_2CO_3$, main isomer): δ=1.13 (t, 3H); 1.26 (t, 3H); 3.24 (pentuplet, 2H); 4.25 (q, 2H); 4.72 (d, 1H); 5.28 (d, 1H); 5.39 (d, 1H); 5.90-6.07 (m, 1H); 6.25 (d, 1H); 6.44 (dd, 1H); 6.49 (t, 1H); 7.85 (d, 1H); 8.13 (s, 1H); 10.47 (s, 1H) ppm.

Intermediate Compound INTE5

Cyano-[5-[1-[6-(2,2-dimethyl-propionylamino)-pyridin-2-ylamino]-meth-(E/Z)-ylidene]-3-ethyl-4-oxo-thiazolidin-(2-(E or Z))-ylidene]-acetic acid allyl ester

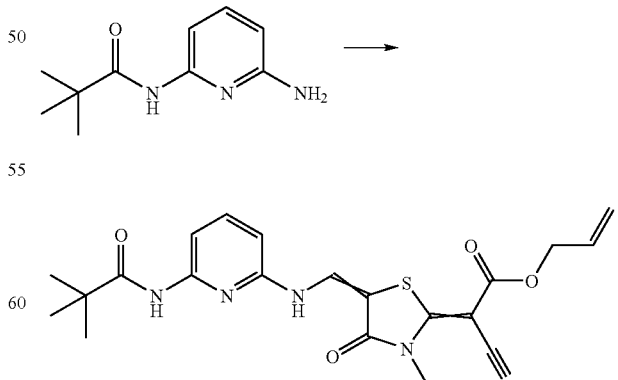

1.35 g of the compound that is described under Intermediate Compound INT15) is dissolved in 50 ml of 1-propanol.

2.0 g of the compound that is described under Intermediate Compound INTT5) is added, and it is stirred under reflux for 3 hours. After cooling, the reaction mixture is filtered, and the solid that is obtained is recrystallized from ethanol. 2.47 g of the title compound is obtained as a pH-dependent 5-(E/Z)-isomer mixture.

1H-NMR (DMSO-d6, stored with $K_2CO_3$, main isomer): δ=1.20-1.31 (m, 12H); 4.27 (q, 2H); 4.72 (d, 2H); 5.28 (d, 2H); 5.39 (d, 2H); 5.91-6.06 (m, 1H); 6.29 (d, 2H); 7.68-7.80 (m, 2H); 8.86 (s, 1H); 9.71 (s, 1H); 10.94 (s, 1H) ppm.

The compounds below are produced analogously to the above-described process.

TABLE 3

Ester Intermediate Compounds

| Example No. | Structure and Name | $^1$H-NMR | Molecular Weight/ MS (ESI) [M + 1]$^+$ | Educt/ Synthesis Analogously to |
|---|---|---|---|---|
| INTE6 | 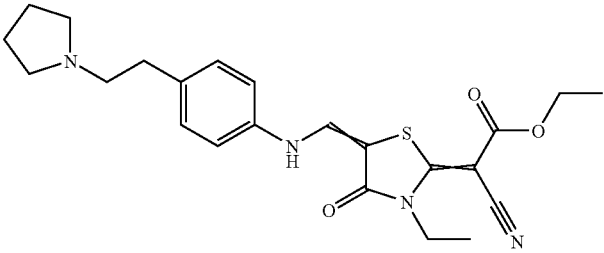<br>Cyano-[3-ethyl-4-oxo-5-[1-[4-(2-pyrrolidin-1-yl-ethyl)-phenylamino]-meth-(E/Z)-ylidene]-thiazolidin-(2-(E or Z))-ylidene]-acetic acid ethyl ester | $^1$H-NMR(DMSO-d6, stored with $K_2CO_3$, main isomer): δ = 1.16-1.33(m, 6H); 1.59-1.75(m, 4H); 2.38-2.50(m, 4H); 2.59(t, 2H); 2.69(t, 2H); 4.13-4.31(m,4H); 7.10-7.29(m, 4H); 8.19(s, 1H); 10.53(s, 1H) ppm. | MW: 440.57<br>MS (ESI) [M+1]$^+$: 441 | INTT3/ INTE1 |
| INTE7 | 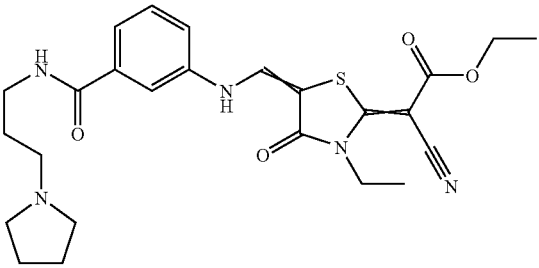<br>Cyano-[3-ethyl-4-oxo-5-[1-[3-(3-pyrrolidin-1-yl-propylcarbamoyl)-phenylamino]-meth-(E/Z)-ylidene]-thiazolidin-(2-(E or Z))-ylidene]-acetic acid ethyl ester | $^1$H-NMR(DMSO-d6, stored with $K_2CO_3$, main isomer): δ = 1.15-1.32(m,6H); 1.61-1.75(m, 6H); 2.38-2.49(m, 6H); 3.18-3.33(m, 2H); 4.18(q, 2H); 4.23(q, 2H); 7.29(d, 1H); 7.38(t, 1H); 7.48(d, 1H); 7.61(s, 1H); 8.36 (s, 1H); 8.58(t, 1H); 10.61(s, 1H) ppm. | MS (ESI) [M + 1]$^+$: 498 | INTT3/ INTE1 |
| INTE8 | 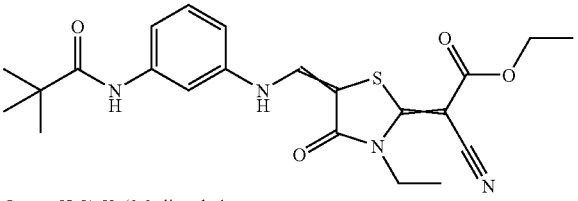<br>Cyano-[5-[1-[3-(2,2-dimethyl-propionylamino)-phenylamino]-meth-(E/Z)-ylidene]-3-ethyl-4-oxo-thiazolidin-(2-(E or Z))-ylidene]-acetic acid allyl ester | (DMSO-d6, stored with $K_2CO_3$, main isomer): δ = 1.19-1.32(m, 12H); 4.27(q, 2H); 4.72(d, 2H); 5.27(m, 1H); 5.39(m, 1H); 5.91-6.07(m, 1H); 6.99(d, 1H); | 454.55<br>455 | INTT5/ INTE2 |

TABLE 3-continued

Ester Intermediate Compounds

| Example No. | Structure and Name | ¹H-NMR | Molecular Weight/ MS (ESI) [M + 1]⁺ | Educt/ Synthesis Analogously to |
|---|---|---|---|---|
| | | 7.28(t, 1H); 7.39(d, 1H); 7.78(s, 1H); 8.13(d, 1H); 9.28(s, 1H); 10.67(d, 1H) ppm. | | |
| INTE9 | 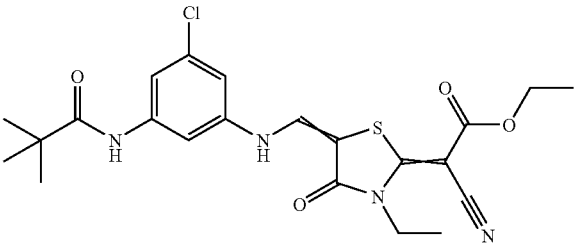<br>[5-[1-[3-Chloro-5-(2,2-dimethyl-propionylamino)-phenylamino]-meth-(E/Z)-ylidene]-3-ethyl-4-oxo-thiazolidin-(2-(E or Z))-ylidene]-cyano-acetic acid ethyl ester | (DMSO-d6, stored with K₂CO₃, main isomer): δ =<br><br>1.17-1.30(m, 15H); 4.16-4.30(m, 4H); 7.01(s, 1H); 7.51(s, 1H); 7.63(s, 1H); 8.15(s, 1H); 9.33(s, 1H); 10.60(s, 1H) ppm. | 476.98<br>477 | INTT3/<br>INTE1 |
| INTE10 | 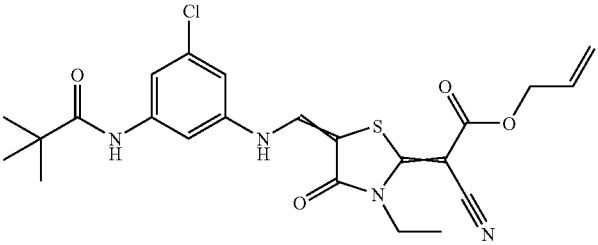<br>[5-[1-[3-Chloro-5-(2,2-dimethyl-propionylamino)-phenylamino]-meth-(E/Z)-ylidene]-3-ethyl-4-oxo-thiazolidin-(2-(E or Z))-ylidene]-cyano-acetic acid allyl ester | (DMSO-d6, stored with K₂CO₃, main isomer): δ =<br><br>1.17-1.31(m, 12H); 4.26(q, 2H); 4.72(d, 1H); 5.26(d, 1H); 5.38(d, 1H); 5.91-6.08(m, 1H); 7.06(s, 1H); 7.52(s, 1H); 7.70(s, 1H); 8.13(s, 1H); 9.38(s, 1H); 10.61(s, 1H) ppm. | 488.99<br>489 | INTT3/<br>INTE1 |
| INTE11 | 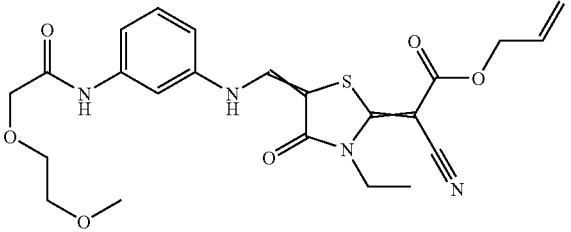<br>Cyano-[3-ethyl-5-[1-{3-[2-(2-methoxy-ethoxy)-acetylamino]-phenylamino}-meth-(E/Z)-ylidene]-4-oxo-thiazolidin-(2-(E or Z))-ylidene]-acetic acid allyl ester | (DMSO-d6, stored with K₂CO₃, main isomer): δ =<br><br>1.25(t, 3H); 3.30(s, 3H); 3.55(m, 2H); 3.68(m, 2H); 4.10(s, 2H); 4.26(q, 2H); 4.72(d, 2H); | 486.55<br>487 | INTT5/<br>INTE2 |

TABLE 3-continued

Ester Intermediate Compounds

| Example No. | Structure and Name | $^1$H-NMR | Molecular Weight/ MS (ESI) [M + 1]$^+$ | Educt/ Synthesis Analogously to |
|---|---|---|---|---|
| | | 5.77(d, 1H); 5.89(d, 1H); 5.90-6.07(m, 1H); 7.03(m, 1H); 7.24-7.36(m, 2H); 7.78(s, 1H); 8.15(s, 1H); 9.72(s, 1H); 10.69(s, 1H) ppm. | | |
| INTE12 | 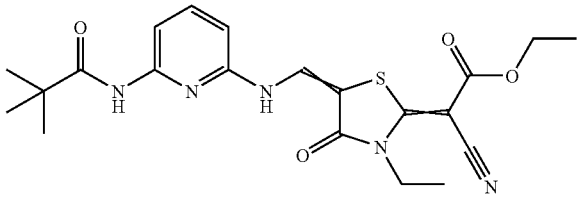 Cyano-[5-[1-[6-(2,2-dimethyl-propionylamino)-pyridin-2-ylamino]-meth-(E/Z)-ylidene]-3-ethyl-4-oxo-thiazolidin-(2-(E or Z))-ylidene]-acetic acid ethyl ester | (DMSO-d6, stored with K$_2$CO$_3$, main isomer): δ = 1.18-1.32(m, 15H); 4.16-4.31(m, 4H); 6.80(d, 1H); 7.68-7.79(m, 2H); 8.86(s, 1H); 9.70(s, 1H); 10.92(s, 1H) ppm. | 443.53 444 | INTT3/ INTE1 |
| INTE13 | 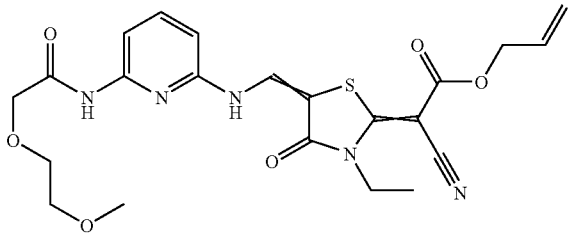 Cyano-[3-ethyl-5-[1-{6-[2-(2-methoxy-ethoxy)-acetylamino]-pyridin-2-ylamino}-meth-(E/Z)-ylidene]-4-oxo-thiazolidin-(2-(E or Z))-ylidene]-acetic acid allyl ester | (DMSO-d6, stored with K$_2$CO$_3$, main isomer): δ = 1.26(t, 3H); 3.33(s, 3H); 3.52(m, 2H); 3.70(m, 2H); 4.26(q, 2H); 4.71(d, 1H); 5.27(d, 1H); 5.39(d, 1H); 5.92-6.07(m, 1H); 6.80(d, 1H); 7.70-7.83(m, 2H); 8.80(s, 1H); 9.97(s, 1H); 11.01(s, 1H) ppm. | 487.53 488 | INTT5/ INTE2 |
| INTE14 | 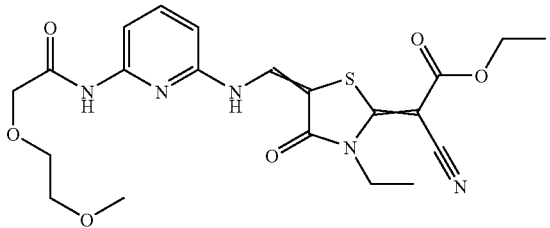 Cyano-[3-ethyl-5-[1-{6-[2-(2-methoxy-ethoxy)-acetylamino]-pyridin-2-ylamino}-meth-(E/Z)-ylidene]-4-oxo-thiazolidin-(2-(E or Z))-ylidene]-acetic acid ethyl ester | (DMSO-d6, stored with K$_2$CO$_3$, main isomer): δ = 1.20-1.32(m, 6H); 3.32(s, 3H); 3.53(m, 2H); 3.70(m, 2H); 4.25(s, 2H); 4.20-4.31(m, 4H); | 475.52 476 | INTT3/ INTE1 |

TABLE 3-continued

Ester Intermediate Compounds

| Example No. | Structure and Name | ¹H-NMR | Molecular Weight/ MS (ESI) [M + 1]⁺ | Educt/ Synthesis Analogously to |
|---|---|---|---|---|
| | | 6.82(d, 1H); 7.71-8.84(m, 2H); 8.74(s, 1H); 10.00(s, 1H); 10.98(s, 1H) ppm. | | |
| INTE15 | 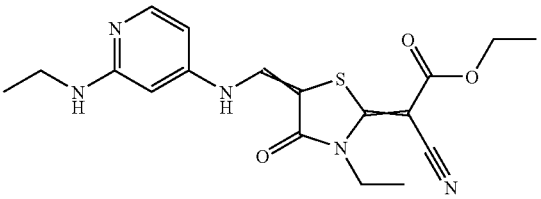<br>Cyano-[3-ethyl-5-[1-(2-ethylamino-pyridin-4-ylamino)-meth-(E/Z)-ylidene]-4-oxo-thiazolidin-(2-(E or Z))-ylidene]-acetic acid ethyl ester | (DMSO-d6, stored with K₂CO₃, main isomer): δ = 1.12(t, 3H); 1.19-1.32(m, 6H); 3.23(m, 2H); 4.15-4.31(m, 4H); 6.25(d, 1H); 6.44(dd, 1H); 6.49(t, 1H); 7.35(d, 1H); 8.11(s, 1H); 10.46(s, 1H) ppm. | 387.46 388 | INTT3/ INTE1 |
| INTE16 | 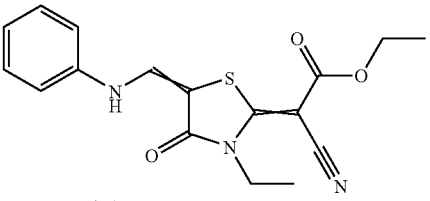<br>Cyano-[3-ethyl-4-oxo-5-[1-phenylamino-meth-(E)-ylidene]-thiazolidin-(2Z)-ylidene]-acetic acid ethyl ester | (DMSO-d6, stored with K₂CO₃, main isomer): δ = 1.18-1.31(m, 6H); 4.15-4.31(m, 4H); 7.10(m, 1H); 7.28-7.41(m, 4H); 8.20(d, 1H); 10.52(d, 1H) ppm. | 343.41 344 | INTT3/ INTE1 |
| INTE17 | 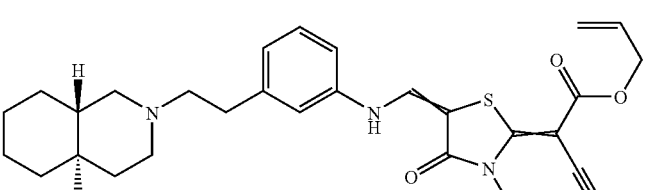<br>Cyano-[3-ethyl-5-[1-{3-[(4aR, 8aS)-2-(decahydro-isoquinolin-2-yl)-ethyl]-phenylamino}-meth-(E/Z)-ylidene]-4-oxo-thiazolidin-(2-(E or Z))-ylidene]-acetic acid allyl ester | (DMSO-d6, stored with K₂CO₃, main Isomer): δ = 0.72-1.28(m, 10H); 1.40-1.69(m, 6H); 1.90(t, 1H); 2.37-2.50(m, 2H); 2.62-2.72(m, 2H); 2.76(d, 2H); 2.90(d, 2H); 4.21(q, 2H); 4.67(d, 2H); 5.22(d, 1H); 5.34(d, 1H); 5.88-6.01(m, 1H); 6.91(d, 1H); 7.08(d, 1H); 7.15-7.26(m, 2H); 8.19(s, 1H); 10.49(s, b, 1H) ppm. | | INTT5/ INTE2 |

SYNTHESIS OF ADDITIONAL INTERMEDIATE PRODUCTS

Intermediate Compound INTA1

Production Variant 1

Cyano-[3-ethyl-4-oxo-5-[1-[3-(2-pyrrolidin-1-yl-ethyl)-phenylamino]-meth-(E/Z)-ylidene]-thiazolidin-(2-(E or Z))-ylidene]-acetic acid

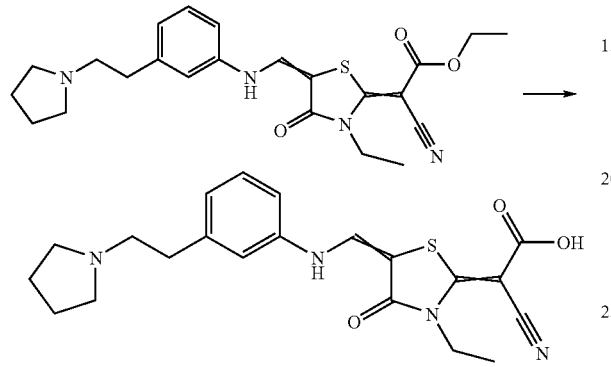

1.1 g of potassium-(tert)-butylate is introduced into 50 ml of tetrahydrofuran at 0° C. and mixed with 45 μl of water. 540 mg of the compound that is described under Intermediate Compound INTE1) is added, and it is stirred for 30 minutes at 0° C., and for 20 hours at room temperature. 0.25 ml of triethylamine and 10.5 ml of 2 M hydrochloric acid in diethyl ether are added at 0° C., and it is stirred for one hour at room temperature. The solvent is condensed under high vacuum, and the residue is further reacted without additional purification.

MW: 412.51; MS (ESI) [M+1]$^+$: 413

Production Variant 2

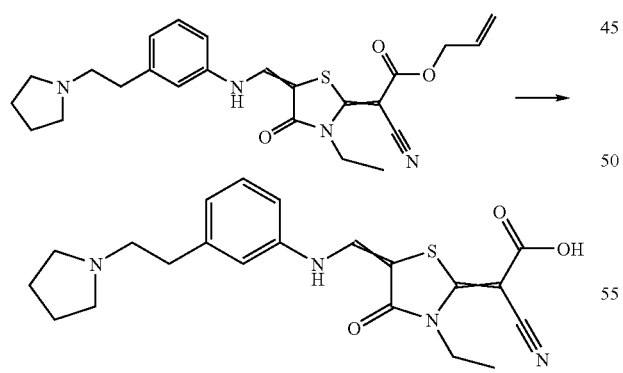

300 mg of the compound that is described under Intermediate Compound INTE2), 80 mg of Pd(PPh$_3$)$_4$ and 0.6 ml of morpholine are dissolved in 18 ml of tetrahydrofuran and stirred for 15 hours. After the addition of 40 ml of diethyl ether, the solid that is obtained is filtered off, dried in a vacuum, and dissolved in 10 ml of dimethylformamide. The solution is added to a suspension of 770 mg of PL-MIA resin of the Polymer Laboratories GmbH Company in 5 ml of dimethylformamide, and it is stirred for 15 hours at room temperature. The reaction mixture is filtered, and the solvent is condensed under high vacuum. 280 mg of the title compound is obtained as a crude product.

1H-NMR (DMSO-d6, stored with K$_2$CO$_3$): δ=1.20 (t, 3H); 1.88 (m, 4H); 2.50 (m, 4H); 3.09 (m, 2H); 3.20 (m, 2H); 4.20 (q, 2H); 6.93 (d, 1H); 7.04-7.12 (m, 2H); 7.23 (t, 1H); 7.88 (s, 1H); 9.97 (s, 1H) ppm.

Intermediate Compound INTA2

Cyano-[3-ethyl-5-[1-(2-ethylamino-pyridin-4-ylamino)-meth-(E/Z)-ylidene]-4-oxo-thiazolidin-(2-(E or Z))-ylidene]-acetic acid

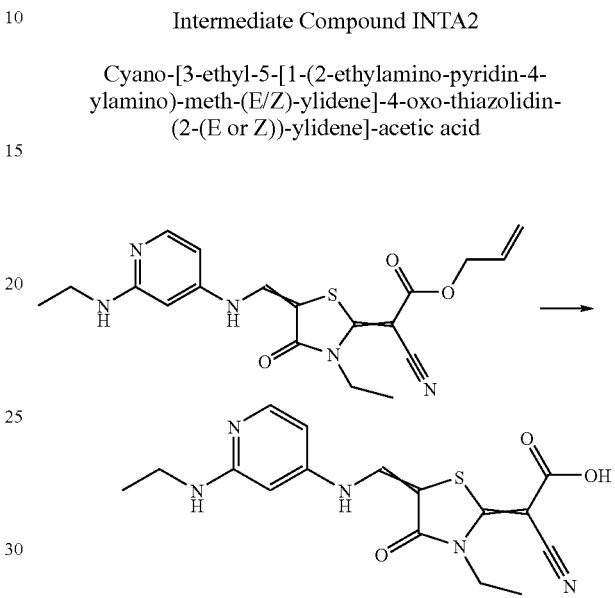

1.2 g of the compound that is described under Intermediate Compound INTE4), 350 mg of Pd(PPh$_3$)$_4$ and 2.6 ml of morpholine are dissolved in 60 ml of tetrahydrofuran and stirred for one hour at room temperature. After 40 ml of hexane is added, the solid that is obtained is filtered off, dried in a vacuum, and dissolved in 20 ml of dimethylformamide. The solution is added to a suspension of 6.0 g of PL-MIA resin of the Polymer Laboratories GmbH Company in 30 ml of dimethylformamide, and it is stirred for 15 hours at room temperature. The reaction mixture is filtered, and the solvent is condensed under high vacuum. 970 mg of the title compound is obtained as a crude product.

MW: 359.41; MS (ESI) [M+1]$^+$: 360

1H-NMR (DMSO-d6, stored with K$_2$CO$_3$): δ=1.11 (t, 3H); 1.22 (t, 3H); 3.23 (m, 2H); 4.22 (q, 2H); 6.25 (s, 1H); 6.42 (d, 1H); 6.54 (s, b, 1H); 7.81 (d, 1H); 7.95 (s, 1H); 10.20 (s, 1H) ppm.

Intermediate Compound INTA3

Cyano-[5-[1-[6-(2,2-dimethyl-propionylamino)-pyridin-2-ylamino]-meth-(E/Z)-ylidene]-3-ethyl-4-oxo-thiazolidin-(2-(E or Z))-ylidene]-acetic acid

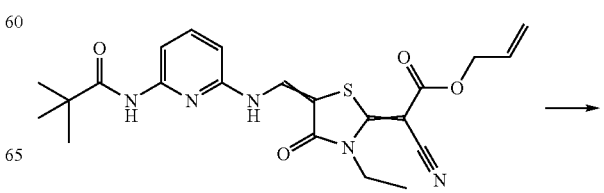

-continued

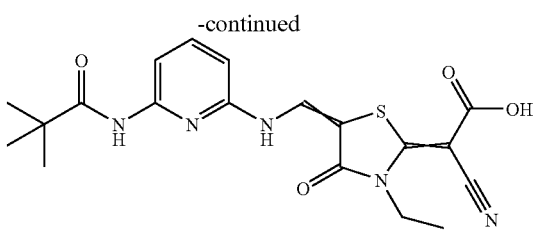

2.2 g of the compound that is described under Intermediate Compound INTE5), 560 mg of Pd(PPh$_3$)$_4$ and 4.2 ml of morpholine are dissolved in 110 ml of tetrahydrofuran and stirred for one hour at room temperature. After 50 ml of hexane is added, the precipitated solid is filtered off, dried in a vacuum, and dissolved in 25 ml of dimethylformamide. The solution is added to a suspension of 9.6 g of PL-MIA resin of the Polymer Laboratories GmbH Company in 50 ml of dimethylformamide and stirred for 15 hours at room temperature. The reaction mixture is filtered, and the solvent is condensed under high vacuum. 2.1 g of the title compound is obtained as a crude product.

MW: 415.47; MS (ESI) [M+1]$^+$: 416

1H-NMR (DMSO-d6, stored with K$_2$CO$_3$): δ=1.15-1.30 (m, 12H); 4.23 (q, 2H); 6.80 (m, 1H); 7.64-7.74 (m, 2H); 8.73 (d, 1H); 9.68 (s, 1H); 10.68 (d, 1H) ppm.

The compounds below are produced analogously to the above-described process.

TABLE 4

Acid-Intermediate Compounds

| Example No. | Structure and Name | $^1$H-NMR | Molecular Weight/ MS (ESI) [M + 1]$^+$ | Educt/ Synthesis Analogously to |
|---|---|---|---|---|
| INTA4 | Cyano-[3-ethyl-4-oxo-5-[1-[4-(2-pyrrolidin-1-yl-ethyl)-phenylamino]-meth-(E/Z)-ylidene]-thiazolidin-(2-(E or Z))-ylidene]-acetic acid | | MS (ESI) [M + 1]$^+$: 413 | MW: 412.51 / INTE6/ INTA1 |
| INTA5 | Cyano-[3-ethyl-4-oxo-5-[1-[3-(3-pyrrolidin-1-yl-propylcarbamoyl)-phenylamino]-meth-(E/Z)-ylidene]-thiazolidin-(2-(E or Z))-ylidene]-acetic acid | | MS (ESI) [M + 1]$^+$: 470 | MW: 469.56 / INTE7/ INTA1 |
| INTA6 | Cyano-[5-[1-[3-(2,2-dimethyl-propionylamino)-phenylamino]-meth-(E/Z)-ylidene]-3-ethyl-4-oxo-thiazolidin-(2-(E or Z))-ylidene]-acetic acid | | MS (ESI) [M + 1]$^+$: 415 | MW: 414.49 / INTE8/ INTA3 |

TABLE 4-continued

Acid-Intermediate Compounds

| Example No. | Structure and Name | ¹H-NMR | Molecular Weight/ MS (ESI) [M + 1]⁺ | Educt/ Synthesis Analogously to |
|---|---|---|---|---|
| INTA7 | 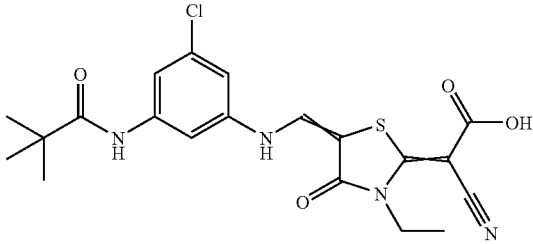<br>[5-[1-[3-Chloro-5-(2,2-dimethyl-propionylamino)-phenylamino]-meth-(E/Z)-ylidene]-3-ethyl-4-oxo-thiazolidin-(2-(E or Z))-ylidene]-cyano-acetic acid | MS (ESI) [M + 1] 449 | MW: 448.93 | INTE10/ INTA3 |
| INTA8 | 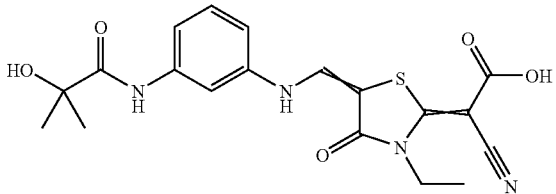<br>Cyano-[3-ethyl-5-[1-[3-(2-hydroxy-2-methyl-propionylamino)-phenylamino]-meth-(E/Z)-ylidene]-4-oxo-thiazolidin-(2-(E or Z))-ylidene]-acetic acid | (DMSO-d6, stored with $K_2CO_3$, main isomer): δ = 1.20(t, 3H); 1.36(s, 6H); 4.18(q, 2H); 5.88(s, 1H); 6.90(d, 1H); 7.20(t, 1H); 7.38(d, 1H); 7.75(s, 1H); 7.81(d, 1H); 9.67(s, 1H); 9.89(d, 1H) ppm. | MW: 416.45<br><br>MS (ESI) [M + 1]⁺: 417 | INTE3/ INTA3 |
| INTA9 | 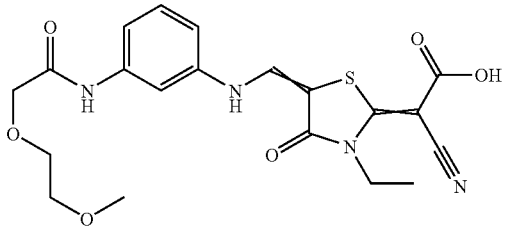<br>Cyano-[3-ethyl-5-[1-{3-[2-(2-methoxy-ethoxy)-acetylamino]-phenylamino}-meth-(E/Z)-ylidene]-4-oxo-thiazolidin-(2-(E or Z))-ylidene]-acetic acid | (DMSO-d6, stored with $K_2CO_3$, main isomer): δ = 1.22(t, 3H); 3.30(s, 2H); 3.54(m, 2H); 3.68(m, 2H); 4.09(s, 2H); 4.23(q, 2H); 7.01(m, 1H), 7.22-7.32(m, 2H); 7.75(s, 1H); 8.04(d, 1H); 9.71(s, 1H); 10.50(d, 1H) ppm. | MW: 446.48<br><br>MS (ESI) [M + 1]⁺: 447 | INTE11/ INTA3 |

TABLE 4-continued

Acid-Intermediate Compounds

| Example No. | Structure and Name | $^1$H-NMR | Molecular Weight/ MS (ESI) [M + 1]$^+$ | Educt/ Synthesis Analogously to |
|---|---|---|---|---|
| INTA10 | 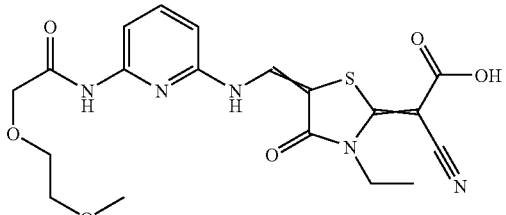 Cyano-[3-ethyl-5-[1-{6-[2-(2-methoxy-ethoxy)-acetylamino]-pyridin-2-ylamino}-meth-(E/Z)-ylidene]-4-oxo-thiazolidin-(2-(E or Z))-ylidene]-acetic acid | (DMSO-d6, stored with K$_2$CO$_3$, main isomer): δ = 1.23(t, 3H); 3.34(s, 3H); 3.51(m, 2H); 3.69(m, 2H); 4.15(s, 2H); 4.22(q, 2H); 6.81(dd, 1H); 7.69-7.78(m, 2H); 7.95(s, 1H); 8.64(d, 1H); 9.98(s, 1H); 10.73(d, 1H) ppm. | MW: 447.47 MS (ESI) [M + 1]$^+$: 448 | INTE13/ INTA3 |
| INTA11 | 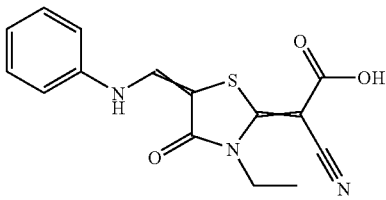 | | 315.35 316 | INTE16/ INTA1 |
| INTA12 | 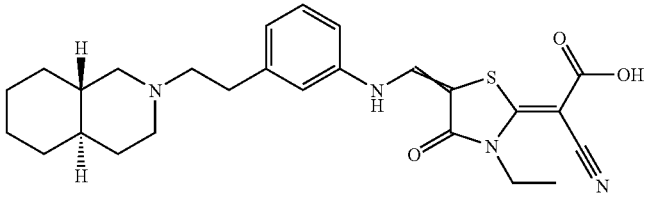 Cyano-[3-ethyl-5-({3-[(4aR, 8aS)-2-(decahydro-isoquinolin-2-yl)-ethyl]-phenylamino}-meth-(E/Z)-ylidene-4-oxo-thiazolidin-(2-(E or Z))-ylidene]-acetic acid | | 480.63 481 | INTE17/ INTA3 |

SYNTHESIS OF ADDITIONAL INTERMEDIATE PRODUCTS

Intermediate Compound INTB1

2-Cyano-2-[3-ethyl-4-oxo-5-[1-[3-(2-pyrrolidin-1-yl-ethyl)-phenylamino]-meth-(E/Z)-ylidene]-thiazolidin-(2-(E or Z))-ylidene]-N-(2-hydroxy-1,1-dimethyl-ethyl)-acetamide

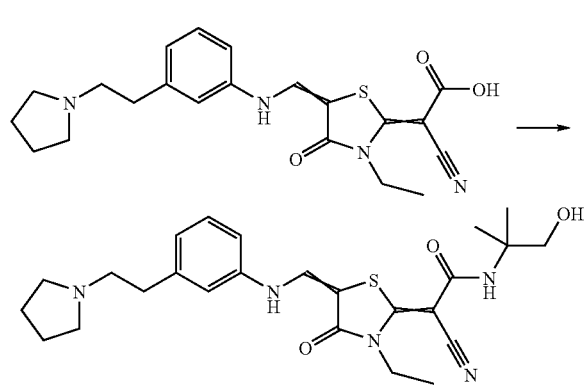

170 mg of the crude product that is described under Intermediate Compound INTA1) (about 0.42 mmol) is dissolved in 10 ml of dimethylformamide, mixed with 248 mg of sodium bicarbonate, 62 μl of 2-amino-2-methyl-propan-1-ol, and 200 mg of TBTU, and stirred for 18 hours at room temperature. The reaction mixture is mixed with semi-saturated sodium bicarbonate solution and extracted with dichloromethane. The organic solution is washed with saturated sodium chloride solution, dried on sodium sulfate, concentrated by evaporation, and after purification by chromatography on silica gel, 61 mg of the title compound is obtained as a pH-dependent 5-(E/Z)-isomer mixture.

1H-NMR (DMSO-d6, stored with $K_2CO_3$, main isomer): δ=1.30 (t, 3H); 1.36 (s, 6H); 1.74 (m, 4H); 2.54 (m, 4H); 2.69 (m, 2H); 2.79 (m, 2H); 3.43 (d, 2H); 4.27 (q, 2H); 5.27 (t, 1H); 6.74 (s, 1H); 7.00 (d, 1H); 7.18 (d, 1H); 7.25-7.35 (m, 2H); 8.19 (s, 1H); 10.31 (s, 1H) ppm.

Intermediate Compound INTB2

N-[3-[[[2-[(E or Z)-2-[[(1-Aminoethylidene)amino]-oxy]-1-cyano-2-oxoethylidene]-3-ethyl-4-oxothiazolidin-5-(E/Z)-ylidene]methyl]amino]phenyl]-2,2-dimethylpropanamide

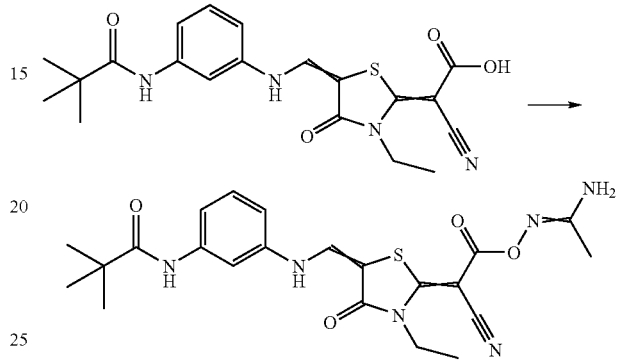

1.39 g of the crude product that is described under Intermediate Compound INTA6) (about 1.0 mmol) is dissolved in 12 ml of dichloromethane and 12 ml of dioxane, mixed with 0.94 ml of diisopropylethylamine, 103 mg of acetamidoxime, and 622 mg of PyBOP and stirred for 4 hours at room temperature. The reaction mixture is mixed with semi-saturated sodium bicarbonate solution and extracted with ethyl acetate. The organic solution is dried on sodium sulfate and concentrated by evaporation.

The solid that is obtained is recrystallized from ethanol. 354 mg of the title compound is obtained as a pH-dependent 5-(E/Z)-isomer mixture.

1H-NMR (DMSO-d6, stored with $K_2CO_3$, main isomer): δ=1.24 (s, 9H); 1.27 (t, 3H); 1.81 (s, 3H); 4.26 (q, 2H); 5.30-6.90 (b, 2H); 6.98 (d, 1H); 7.27 (t, 1H); 7.38 (d, 1H); 7.75 (s, 1H); 8.12 (s, 1H); 9.27 (s, 1H); 10.65 (s, 1H) ppm.

The compounds below are produced analogously to the above-described process.

TABLE 5

| Example No. | Structure and Name | 1H-NMR | Molecular Weight/ MS (ESI) [M + 1]+ | Educt/ Synthesis Analogously to |
|---|---|---|---|---|
| INTB3 | <br>2-Cyano-2-[3-ethyl-4-oxo-5-[1-[4-(2-pyrrolidin-1-yl-ethyl)-phenylamino]-meth-(E/Z)-ylidene]-thiazolidin-(2-(E or Z))-ylidene]-N-(2-hydroxy-1,1-dimethyl-ethyl)-acetamide | (DMSO-d6, stored with $K_2CO_3$, main isomer): δ = 1.22(t, 3H); 1.29(s, 6H); 1.68(m, 4H); 2.45(m, 4H); 2.58(m, 2H); | 483.63/ 484 | INTA4/ INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| | | 2.69(m, 2H); 3.38(d, 2H); 4.20(q, 2H); 5.20(t, 1H), 6.66(s, 1H); 7.15-7.25(m, 4H); 8.08(s, 1H); 10.25(s, 1H) ppm. | | |
| INTB4 | 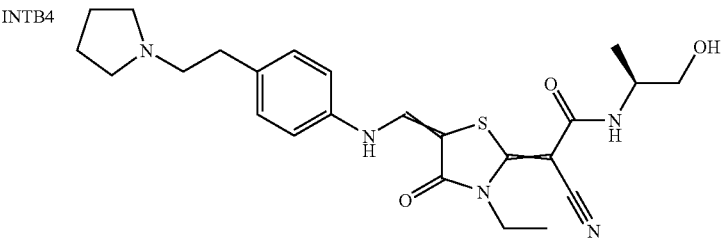 2-Cyano-2-[3-ethyl-4-oxo-5-[1-[4-(2-pyrrolidin-1-yl-ethyl)-phenylamino]-meth-(E/Z)-ylidene]-thiazolidin-(2-(E or Z))-ylidene]-N-((S)-2-hydroxy-1-methyl-ethyl)-acetamide | (DMSO-d6, stored with K$_2$CO$_3$, main isomer): δ = 1.11(d, 3H); 1.25(t, 3H); 1.68(m, 4H); 2.47(m, 4H); 2.59(m, 2H); 2.70(m, 2H); 3.41(m, 1H); 3.91(m, 1H); 4.21(q, 2H); 4.83(t, 1H); 7.03(d, 1H); 7.13-7.24(m, 4H); 8.08(s, 1H); 10.28(s, 1H) ppm. | 469.61/ 470 | INTA4/ INTB1 |
| INTB5 | 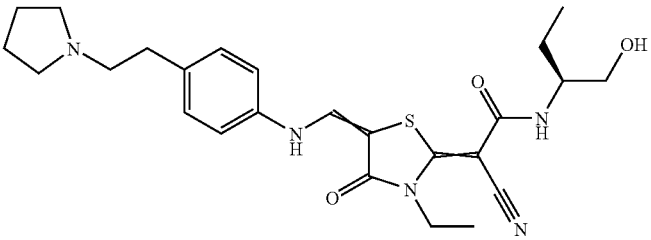 2-Cyano-2-[3-ethyl-4-oxo-5-[1-[4-(2-pyrrolidin-1-yl-ethyl)-phenylamino]-meth-(E/Z)-ylidene]-thiazolidin-(2-(E or Z))-ylidene]-N-((S)-1-hydroxymethyl-propyl)-acetamide | (CDCl$_3$, stored with K$_2$CO$_3$, main isomer): δ = 1.00(t, 3H); 1.27(t, 3H); 1.47-1.73(m, 2H); 1.81(m, 4H); 2.57(m, 2H); 2.67(m, 2H); 2.80(m, 2H); 3.60-3.79(m, 2H); 3.97(m, 1H); 4.38(q, 2H); 6.22(d, 1H); 7.00(d, 2H); 7.21(d, 2H); 7.54(d, 1H); 10.47(d, 1H) ppm. | 483.63/ 484 | INTA4/ INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| INTB6 | 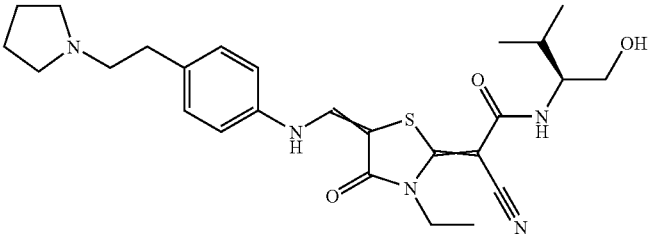<br><br>2-Cyano-2-[3-ethyl-4-oxo-5-[1-[4-(2-pyrrolidin-1-yl-ethyl)-phenylamino]-meth-(E/Z)-ylidene]-thiazolidin-(2-(E or Z))-ylidene]-N-((S)-1-hydroxymethyl-2-methyl-propyl)-acetamide | (CDCl$_3$, stored with K$_2$CO$_3$, main isomer): δ = <br>0.90-1.03(m, 6H);<br>1.40(t, 3H);<br>1.80(m, 4H);<br>1.96(m, 1H);<br>2.57(m, 4H);<br>2.67(m, 2H);<br>2.80(m, 2H),<br>3.63-3.90(m, 3H);<br>4.38(q, 2H);<br>6.30(d, 2H);<br>6.99(d, 2H);<br>7.20(d, 2H);<br>7.52(d, 1H);<br>10.47(d, 1H) ppm. | 497.67/<br>498 | INTA4/<br>INTB1 |
| INTB7 | 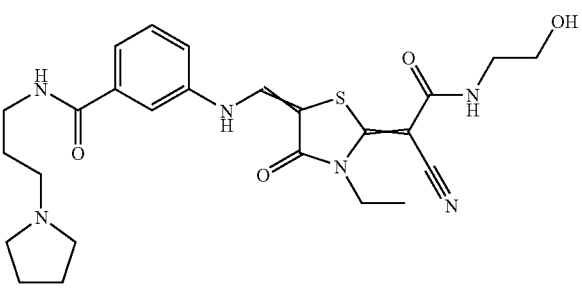<br><br>3-{[2-[1-Cyano-1-(2-hydroxy-ethylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ = <br>1.27(t, 3H);<br>1.58-1.77(m, 6H);<br>2.32-2.47(m, 6H);<br>3.18-3.32(m, 4H);<br>3.48(q, 2H);<br>4.24(q, 2H);<br>4.75(t, 1H);<br>7.34-7.56(m, 4H);<br>7.73(s, 1H);<br>8.19(s, 1H);<br>8.62(t, 1H);<br>10.40(s, 1H) ppm. | MW:<br>512.63<br><br>MS (ESI) [M + 1]$^+$:<br>513 | INTA5/<br>INTB1 |
| INTB8 | 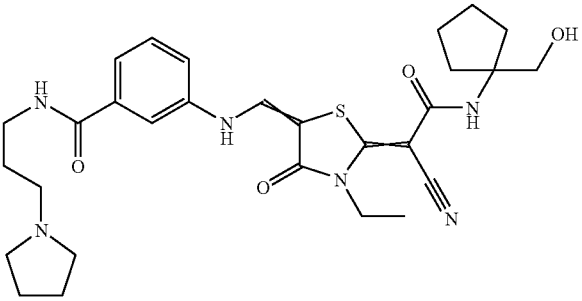<br><br>3-{[2-[1-Cyano-1-(1-hydroxymethyl-cyclopentylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ = <br>1.24(t, 3H);<br>1.40-1.80(m, 12H);<br>1.91(m, 2H);<br>2.33-2.48(m, 6H);<br>3.24-3.38(m, 2H);<br>3.42(s, 2H); | MW:<br>566.72<br><br>MS (ESI) [M + 1]$^+$:<br>567 | INTA5/<br>INTB1 |

TABLE 5-continued

| Example No. | Structure and Name | ¹H-NMR | Molecular Weight/ MS (ESI) [M + 1]⁺ | Educt/ Synthesis Analogously to |
|---|---|---|---|---|
| | | 4.24(q, 2H); 5.11(s, 1H); 6.71(s, 1H); 7.31-7.42(m, 2H); 7.49(m, 1H); 7.70(s, 1H); 8.20(s, 1H); 8.61(t, 1H); 10.35(s, b, 1H) ppm. | | |
| INTB9 | 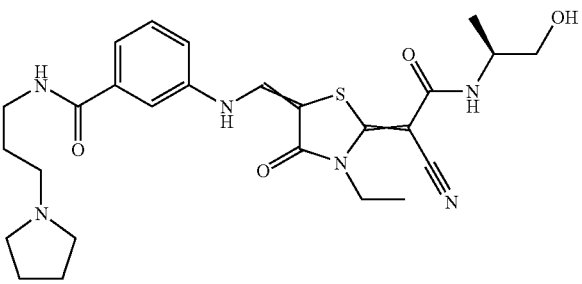 3-{[2-[1-Cyano-1-((S)-2-hydroxy-1-methyl-ethylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | | 526.66/ 527 | INTA5/ INTB1 |
| INTB10 | 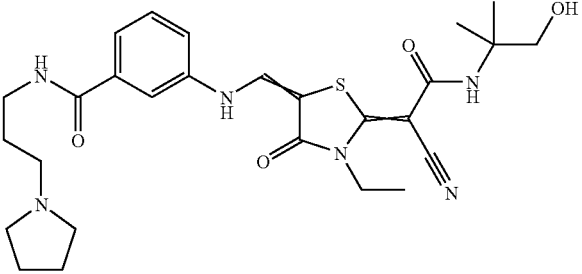 3-{[2-[1-Cyano-1-(2-hydroxy-1,1-dimethyl-ethylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with $K_2CO_3$, main isomer): δ = 1.25(t, 3H); 1.30(s, 6H); 1.60-1.78(m, 6H); 2.36-2.48(m, 6H); 3.21-3.45(m, 4H); 4.21(q, 2H); 5.20(s, 1H); 6.68(s, 1H); 7.33-7.42(m, 2H); 7.50(m, 1H); 7.72(s, 1H); 8.20(s, 1H); 8.61(t, 1H); 10.37(s, b, 1H) ppm. | MW: 540.68 MS (ESI) [M + 1]⁺: 541 | INTA5/ INTB1 |
| INTB11 | 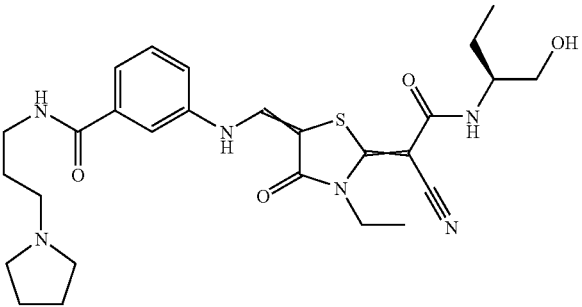 | | 540.69/ 541 | INTA5/ INTB1 |

TABLE 5-continued

| Example No. | Structure and Name | ¹H-NMR | Molecular Weight/ MS (ESI) [M + 1]⁺ | Educt/ Synthesis Analogously to |
|---|---|---|---|---|
| | 3-{[2-[1-Cyano-1-((S)-1-hydroxymethyl-propylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | | | |
| INTB12 | | (DMSO-d6, stored with K₂CO₃, main isomer): δ = | MW: 588.72 | INTA5/ INTB1 |
| | 3-{[2-[1-Cyano-1-((R)-2-hydroxy-1-phenyl-ethylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | 1.26(t, 3H); 1.60-1.77(m, 6H); 2.35-2.48(m, 6H); 3.21-3.40(m, 2H); 3.62-3.79(m, 2H); 4.23(q, 2H); 4.89(q, 1H); 5.06(s, 1H); 7.18-7.43(m, 8H); 7.49(m, 1H); 7.71(s, 1H); 8.19(s, 1H); 8.60(s, 1H); 10.35(s, b, 1H) ppm. | MS (ESI) [M + 1]⁺: 589 | |
| INTB13 | | (DMSO-d6, stored with K₂CO₃, main isomer): δ = | MW: 602.75 | INTA5/ INTB1 |
| | 3-{[2-[1-((S)-1-Benzyl-2-hydroxy-ethylcarbamoyl)-1-cyano-meth-(E or Z)-ylidene]-3-ethyl-4-oxo-thiazolidin-(5-(E/Z))-ylidenemethyl]-amino}-N-(3-pyrrolidin-1-yl-propyl)-benzamide | 1.25(t, 3H); 1.60-1.78(m, 6H); 2.35-2.50(m, 6H); 2.74-2.92(m, 2H); 3.20-3.51(m, 4H); 4.05(m, 1H); 4.23(q, 2H); 4.94(s, 1H); 7.05-7.34(m, 6H); 7.34-7.45(m, 2H); 7.49(m, 1H); 7.72(s, 1H); 8.19(s, 1H); 8.61(s, 1H); 10.35(s, b, 1H) ppm. | MS (ESI) [M + 1]⁺: 603 | |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| INTB14 | 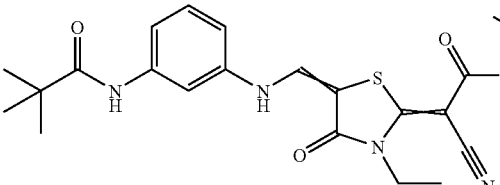<br><br>2-Cyano-2-[5-[1-[3-(2,2-dimethyl-propionylainino)-phenylamino]-meth-(E/Z)-ylidene]-3-ethyl-4-oxo-thiazolidin-(2-(E or Z))-ylidene]-N-(2-hydroxy-1,1-dimethyl-ethyl)-acetamide | (DMSO-d6, stored with K$_2$CO$_3$, main isomer): δ = <br>1.17-1.28(m, 12H); 1.30(s, 6H); 3.38(d, 2H); 4.20(q, 2H); 5.19(t, 1H); 6.68(s, 1 H); 6.94(d, 1H); 7.23(t, 1H); 7.37(d, 1H); 7.70(s, 1H); 8.01(d, 1H); 9.23(s, 1H); 10.38(d, 1H) ppm. | MW: 485.60<br><br>MS (ESI) [M+1]$^+$: 486 | INTA6 INTB1 |
| INTB15 | 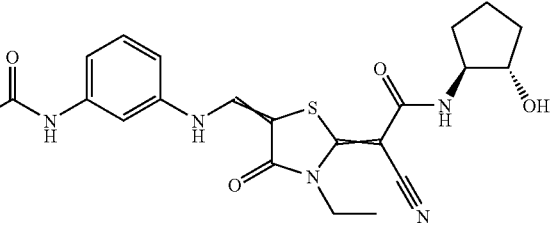<br><br>2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((1S,2S)-2-hydroxy-cyclopentyl)-acetamide | (DMSO-d6, stored with K$_2$CO$_3$, main isomer): δ = <br>1.11-1.31(m, 12H); 1.32-1.69(m, 4H); 1.75-2.02(m, 2H); 3.78-3.91(m, 1 H); 3.91-4.04(m, 1H); 4.22(q, 2H); 4.78(d, 1H); 6.94(d, 1H); 7.24(t, 1H); 7.35(d, 1H); 7.72(s, 1H), 8.01(d, 1H); 9.24(s, 1H); 10.39(d, 1H) ppm. | MW: 497.62<br><br>MS (ESI) [M + 1]$^+$: 498 | INTA6 INTB1 |
| INTB16 | 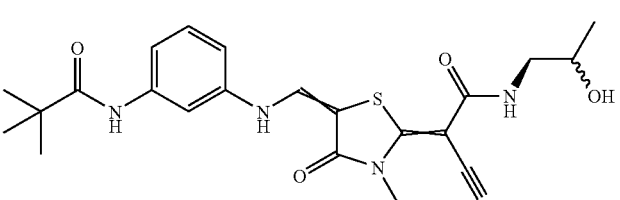<br><br>2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-(2-hydroxy-propyl)-acetamide | (DMSO-d6, stored with K$_2$CO$_3$, main isomer): δ = <br>1.04(d, 3H); 1.16-1.30(m, 1 2H); 2.99-3.14(m, 1H); 3.14-3.29(m, 1H); 3.74(m, 1H); 4.23(q, 1H); 4.80(d, 1H); 6.92(d, 1H); 7.23(t, 1H); 7.28-7.40(m, 2H); 7.19(s, 1H); 8.02(s, 1H); 9.22(s, 1H); 10.40(s, 1H) ppm. | MW: 471.58<br><br>MS (ESI) [M+1]$^+$: 472 | INTA6 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| INTB17 | 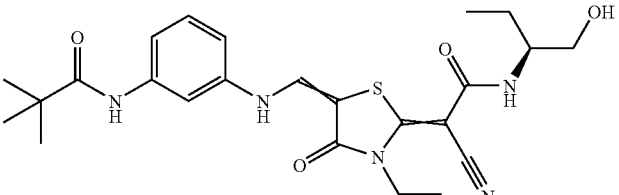<br>2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((S)-1-hydroxymethyl-propyl)-acetamide | (DMSO-d6, stored with K$_2$CO$_3$, main isomer):<br>δ =<br>0.85(t, 3H);<br>1.20-1.31(m, 12H);<br>1.40-1.68(m, 2H);<br>3.45(m, 2H);<br>3.76(m, 1H);<br>4.23(q, 2H);<br>4.28(t, 1H);<br>6.94(d, 1H);<br>7.00(d, 1H);<br>7.24(t, 1H);<br>7.36(d, 1H);<br>7.72(s, 1H);<br>8.02(d, 1H);<br>9.24(s, 1H);<br>10.38(d, 1H) ppm. | MW: 485.60<br>MS (ESI) [M + 1]$^+$: 486 | INTA6 INTB1 |
| INTB18 | 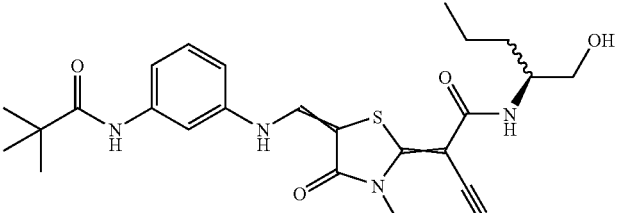<br>2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-(1-hydroxymethyl-butyl)-acetamide | (DMSO-d6, stored with K$_2$CO$_3$, main isomer):<br>δ =<br>0.89(t, 3H);<br>1.15-1.35(m, 14H);<br>1.40-1.55(m, 2H);<br>3.35-3.50(m, 2H);<br>3.87(m, 1H);<br>4.24(q, 2H);<br>4.78(t, 1H);<br>6.95(d, 1H);<br>6.99(d, 1H);<br>7.25(t, 1H);<br>7.36(d, 1H);<br>7.70(s, 1H);<br>8.01(d, 1H);<br>9.24(s, 1H);<br>10.38(d, 1H) ppm. | MW: 499.63<br>MS (ESI) [M + 1]$^+$: 500 | INTA6 INTB1 |
| INTB19 | 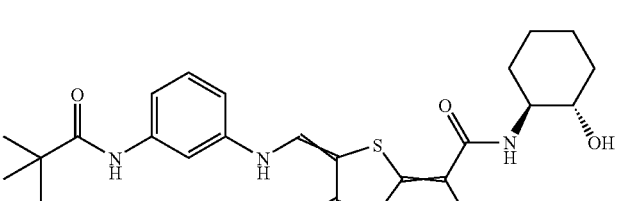<br>2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((1S,2S)-2-hydroxy-cyclohexyl)-acetamide | 1.11-1.35(m, 16H);<br>1.63(s, b, 2H);<br>1.88(s, b, 2H);<br>3.38-3.50(m, 2H);<br>4.23(q, 2H);<br>4.73(d, 1H);<br>6.93(d, 1H);<br>7.02(s, 1H); | MW: 511.65<br>MS (ESI) [M + 1]$^+$: 512 | INTA6 INTB1 |

TABLE 5-continued

| Example No. | Structure and Name | ¹H-NMR | Molecular Weight/ MS (ESI) [M + 1]⁺ | Educt/ Synthesis Analogously to |
|---|---|---|---|---|
| | | 7.23(t, 1H); 7.35(d, 1H); 7.70(s, 1H), 8.02(s, 1H); 9.24(s, 1H); 10.39(s, 1H) ppm. | | |
| INTB20 | 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((S)-1-hydroxymethyl-2-methyl-propyl)-acetamide | (DMSO-d6, stored with K₂CO₃, main isomer): δ = 0.85(d, 3H); 0.90(d, 3H); 1.17-1.30(m, 12H); 1.90(octet, 1H); 3.41-3.60(m, 2H); 3.68(m, 1H); 4.23(q, 2H); 4.75(t, 1H); 6.88(d, 1H); 6.94(d, 1H); 7.25(t, 1H); 7.37(d, 1H); 7.72(d, 1H); 8.02(d, 1H); 9.24(s, 1H); 10.40(d, 1H) ppm. | MW: 499.63  MS (ESI) [M + 1]⁺: 500 | INTA6 INTB1 |
| INTB21 | 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((S)-2-hydroxy-1-methyl-ethyl)-acetamide | (DMSO-d6, stored with K₂CO₃, main isomer): δ = 1.11(d, 2H); 1.19-1.30(m, 12H); 3.41(m, 2H); 3.91(m, 1H); 4.23(q, 2H); 4.83(t, 1H); 6.94(d, 1H); 7.06(d, 1H); 7.24(t, 1H); 7.36(d, 1H); 7.71(s, 1H); 8.02(d, 1H); 9.25(s, 1H); 10.40(d, 1H) ppm. | MW: 471.57  MS (ESI) [M+1]⁺: 472 | INTA6 INTB1 |
| INTB22 | | (DMSO-d6, stored with K₂CO₃, main isomer): δ = | MW: 511.64 | INTA6 INTB1 |

TABLE 5-continued

| Example No. | Structure and Name | ¹H-NMR | Molecular Weight/ MS (ESI) [M + 1]⁺ | Educt/ Synthesis Analogously to |
|---|---|---|---|---|
| | 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-(1-hydroxymethyl-cyclopentyl)-acetamide | 1.17-1.30(m, 12H); 1.44-1.59(m, 2H); 1.59-1.84(m, 4H); 1.84-2.00(m, 2H); 3.42(d, 2H), 4.21(q, 2H); 5.10(t, 1H); 6.70(s, 1H); 6.91(d, 1H); 7.22(t, 1H); 7.35(d, 1H); 7.69(s, 1H); 8.04(s, 1H); 9.21(s, 1H); 10.38(s, 1H) ppm. | MS (ESI) [M + 1]⁺: 512 | |
| INTB23 | 2-{2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-acetylamino}-3-hydroxy-propionic acid methyl ester | (DMSO-d6, stored with K₂CO₃, main isomer): δ = 1.19-1.31(m, 12H); 3.67(s, 3H); 3.69-3.88(m, 2H); 4.25(q, 2H); 4.43(m, 1H); 5.25(t, 1H); 6.93(d, 1H); 7.23(t, 1H); 7.30-7.41(m, 2H); 7.71(s, 1H); 8.07(s, 1H), 9.24(s, 1H); 10.48(s, 1H) ppm. | MW: 515.58 MS (ESI) [M + 1]⁺: 516 | INTA6 INTB1 |
| INTB24 | 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N ((1R,2S)-2-hydroxy-1-methyl-2-((1R,2S)-2-hydroxy-1-methyl-2-phenyl-ethyl)-acetamide | (DMSO-d6, stored with K₂CO₃, main isomer): δ = 0.97(d, 3H); 1.11-1.30(m, 12H); 3.99-4.11(m, 1H); 4.21(q, 2H); 4.75(m, 1 H); 5.60(d, 1H); 6.91(s, b, 1H); 7.05(s, b, 1H); 7.15-7.29(m, 2H); 7.29-7.41(m, 5H); 7.69(s, 1H); 8.06(s, 1H); 9.22(s, 1H); 10.42(s, 1H) ppm. | MW: 547.68 MS (ESI) [M + 1]⁺: 548 | INTA6 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| INTB25 | 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((R)-2-hydroxy-1-phenyl-ethyl) acetamide | (DMSO-d6, stored with K$_2$CO$_3$, main isomer): δ = 1.19-1.32(m, 12H); 3.71(m,2H); 4.24(q, 2H); 4.90(q, 1H); 5.05(t, 1H); 6.91(d, 1H); 7.17-7.27(m, 2H); 7.27-7.40(m, 5H); 7.69(s, 2H); 8.00(s, 1H); 9.21(s, 1H); 10.36(s, 1H) ppm. | MW: 533.65  MS (ESI) [M + 1]$^+$: 534 | INTA6 INTB1 |
| INTB26 | 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((S)-1-hydroxymethyl-2,2-dimethyl-propyl)-acetamide | (DMSO-d6, stored with K$_2$CO$_3$, main isomer): δ = 0.91(s, 9H); 1.20-1.32(m, 12H); 3.58(t, 2H); 3.73(m, 1H); 4.25(q, 2H); 4.68(t, 1H); 6.75(d, 1H); 6.95(d, 1H); 7.24(t, 1H); 7.36(d, 1H), 7.72(s, 1H); 8.02(d, 1H); 9.24(s, 1H); 10.40(d, 1H) ppm. | MW: 513.65  MS (ESI) [M + 1]$^+$: 514 | INTA6 INTB1 |
| INTB27 | 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-((R)-1-hydroxymethyl-3-methyl-butyl)-acetamide | (DMSO-d6, stored with K$_2$CO$_3$, main isomer): δ = 0.83-0.94(m, 6H); 1.18-1.65(m, 15H); 3.41(m, 2H); 3.97(m, 1H); 4.21(q, 2H); 4.78(t, 1H); 6.54(d, 1H); 7.00(d, 1H); | MW: 513.65  MS (ESI) [M + 1]$^+$: 514 | INTA6 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| | | 7.23(t, 1H); 7.35(d, 1H); 7.71(s, 1H); 8.00(d, 1H); 9.24(s, 1H); 10.39(d, 1H) ppm. | | |
| INTB28 | 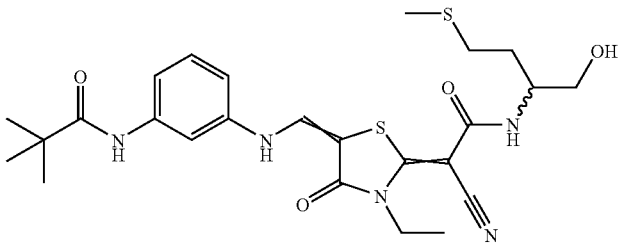<br>2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-(1-hydroxymethyl-3-methylsulfanyl-propyl)-acetamide | (DMSO-d6, stored with K$_2$CO$_3$, main isomer): δ = <br>1.15-1.30(m, 12H); 1.65-1.91(m, 2H); 2.05(s, 3H); 2.40-2.52(m, 2H); 3.38-3.55(m, 2H), 3.90-4.05(m, 1H); 4.23(q, 2H); 4.84(t, 1H); 6.91(d, b, 1H); 7.09(s, b, 1H); 7.23(t, 1H); 7.35(d, 1H); 7.69(s, 1H); 8.04(s, 1H); 9.21(s, 1H); 10.39(s, b, 1H) ppm. | MW: 531.696<br><br>MS (ESI) [M + 1]$^+$: 532 | INTA6 INTB1 |
| INTB29 | 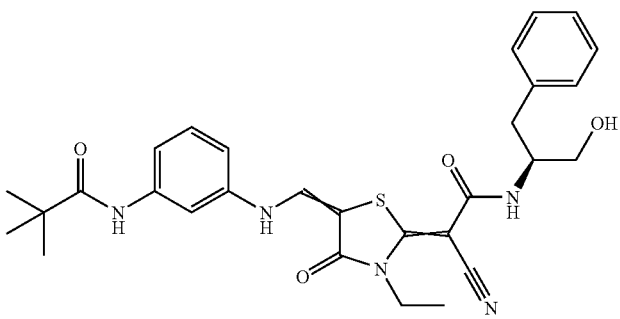<br>N-((S)-1-Benzyl-2-hydroxy-ethyl)-2-cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-acetamide | (DMSO-d6, stored with K$_2$CO$_3$, main isomer): δ = <br>1.13-1.30(m, 1 2H); 2.72-2.93(m, 2H); 3.44(m, 2H); 3.98-4.08(m, 1H); 4.21(q, 2H); 4.94(t, 1H); 6.93(d, 1H); 7.08-7.39(m, 8H); 7.70(s, 1H); 8.02(s, 1H); 9.23(s, 1H); 10.40(s, 1H) ppm. | MW: 547.67<br><br>MS (ESI) [M + 1]$^+$: 548 | INTA6 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| INTB30 | 2-[5-[1-[3-Chloro-5-(2,2-dimethyl-propionylamino)-phenylamino]-meth-(E/Z)-ylidene]-3-ethyl-4-oxo-thiazolidin-(2-(E or Z))-ylidene]-2-cyano-N-((1S,2S)-2-hydroxy-cyclopentyl)-acetamide | (DMSO-d6, stored with K$_2$CO$_3$, main isomer): δ = 1.17-1.31(m, 12H); 1.39-1.52(m, 2H); 1.62(m, 2H); 1.77-2.01(m, 2H); 3.85(m, 1H); 4.00(m, 1H); 4.23(q, 2H); 4.78(d, 1H); 7.02(s, 1H); 7.39(s, 1H); 7.51(s, 1H), 7.65(s, 1H); 8.01(s, 1H); 9.34(s, 1H); 10.37(s, 1H) ppm. | 532.06 533 | INTA7 INTB1 |
| INTB31 | 2-[5-[1-[3-Chloro-5-(2,2-dimethyl-propionylamino)-phenylamino]-meth-(E/Z)-ylidene]-3-ethyl-4-oxo-thiazolidin-(2-(E or Z))-ylidene]-2-cyano-N-(2-hydroxy-1,1-dimethyl-ethyl)-acetamide | (DMSO-d6, stored with K$_2$CO$_3$, main isomer): δ = 1.13-1.28(m, 12H); 1.30(s, 6H); 3.36(d, 2H); 4.20(q, 2H); 5.16(s, b, 1H); 6.35-6.70(s, b, 1H); 6.70-6.98(s, b, 1H); 7.48(s, 2H); 8.13(s, 1H); 9.27(s, 1H); 10.37(s, 1H) ppm. | 520.05 521 | INTA7 INTB1 |
| INTB32 | 2-Cyano-2-[3-ethyl-5-[1-[3-(2-hydroxy-2-methyl-propionylamino)-phenylamino]-meth-(E/Z)-ylidene]-4-oxo-thiazolidin-(2-(E or Z))-ylidene]-N-((1S,2S)-2-hydroxy-cyclopentyl)-acetamide | (DMSO-d6, stored with K$_2$CO$_3$, main isomer): δ = 1.26(t, 3H); 1.35(s, 6H); 1.40-1.54(m, 2H); 1.54-1.69(m, 2H); 1.75-2.03(m, 2H); 3.85(m, 1H); 3.99(m, 1H); 4.23(q, 2H); 4.78(d, 1H); 5.75(s, 1H); 6.96(d, 1H); | 499.59 500 | INTA8 INTB1 |

TABLE 5-continued

| Example No. | Structure and Name | ¹H-NMR | Molecular Weight/ MS (ESI) [M + 1]⁺ | Educt/ Synthesis Analogously to |
|---|---|---|---|---|
| | | 7.25(t, 1H); 7.34(d, 1H); 7.42(d, 1H); 7.86(s, 1H); 8.04(d, 1H); 9.64(s, 1H); 10.38(d, 1H) ppm. | | |
| INTB33 | 2-Cyano-2-[3-ethyl-5-[1-{3-[2-(2-methoxy-ethoxy)-acetylamino]-phenylamino}-meth-(E/Z)-ylidene]-oxo-thiazolidin-(2-(E or Z))-ylidene]-N-((1S,2S)-2-hydroxy-cyclopentyl)-acetamide | (DMSO-d6, stored with K₂CO₃, main isomer): δ = 1.24(t, 3H); 1.37-1.53(m, 2H); 1.61(m, 2H); 1.75-2.03(m, 2H); 3.30(s, 3H); 3.54(m, 2H); 3.69(m, 2H); 3.85(m, 1H), 3.99(m, 1H); 4.09(s, 2H); 4.25(q, 2H); 4.79(d, 1H); 7.00(m, 1H); 7.22-7.30(m, 2H); 7.36(d, 1H); 7.72(s, 1H); 8.01(d, 1H); 9.71(s, 1H); 10.41(d, 1H) ppm. | 529.62 530 | INTA9 INTB1 |
| INTB34 | 2-Cyano-2-[3-ethyl-5-[1-{3-[2-(2-methoxy-ethoxy)-acetylamino]-phenylamino}-meth-(E/Z)-ylidene]-4-oxo-thiazolidin-(2-(E or Z))-ylidene]-N-(2-hydroxy-1,1-dimethyl-ethyl)-acetamide | (DMSO-d6, stored with K₂CO₃, main isomer): δ = 1.24(t, 3H); 1.30(s, 6H); 3.31(s, 3H); 3.38(d, 2H); 3.55(m, 2H); 3.69(m, 2H); 4.09(s, 2H), 4.21(q, 2H); 5.20(t, 1H); 6.70(s, 1H), 7.01(m, 1H); 7.23-7.32(m, 2H); 7.74(s, 1H); 8.02(d, 1H); 9.70(s, 1H); 10.40(d, 1H) ppm. | 517.60 518 | INTA9 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| INTB35 | 2-Cyano-2-[5-[1-[6-(2,2-dimethyl-propionylamino)-pyridin-2-ylamino]-meth-(E/Z)-ylidene]-3-ethyl-4-oxo-thiazolidin-(2-(E or Z))-ylidene]-N-((1S,2S)-2-hydroxy-cyclopentyl)-acetamide | (DMSO-d6, stored with K$_2$CO$_3$, main isomer): δ = 1.18-1.32(m, 1 2H); 1.38-1.54(m, 2H); 1.61(m, 2H); 1.77-2.03(m, 2H); 3.85(m, 1H); 4.00(m, 1H); 4.23(q, 2H); 4.79(d, 1H); 6.78(d, 1H); 7.41(d, 1H); 7.65-7.76(m, 2H), 8.74(s, 1H); 9.68(s, 1H); 10.70(s, 1H) ppm. | 498.61 499 | INTA9 INTB1 |
| INTB36 | 2-Cyano-2-[5-[1-[6-(2,2-dimethyl-propionylamino)-pyridin-2-ylainino]-meth-(E/Z)-ylidene]-3-ethyl-4-oxo-thiazolidin-(2-(E or Z))-ylidene]-N-(2-hydroxy-1,1-dimethyl-ethyl)-acetamide | (DMSO-d6, stored with K$_2$CO$_3$, main isomer): δ = 1.06(t, 3H); 1.25(s, 9H); 1.30(s, 6H); 3.39(d, 2H); 4.21(q, 2H); 5.20(t, 1H); 6.72(s, 1H); 6.79(dd, 1H); 7.65-7.77(m, 2H); 8.55(s, 1H); 9.68(s, 1H); 10.68(s, 1H) ppm. | 486.59 487 | INTA9 INTB1 |
| INTB37 | 2-Cyano-2-[3-ethyl-5-[1-{6-[2-(2-methoxy-ethoxy)-acetylamino]-pyridin-2-ylamino}-meth-(E/Z)-ylidene]-4-oxo-thiazolidin-(2-(E or Z))-ylidene]-N-((1S,2S)-2-hydroxy-cyclopentyl)-acetamide | (DMSO-d6, stored with K$_2$CO$_3$, main isomer): δ = 1.26(t, 3H); 1.35-1.54(m, 2H); 1.62(m, 2H); 1.75-2.04(m, 2H); 3.33(s, 3H); 3.52(m, 2H); 3.79(m, 2H); 3.84(m, 2H); 3.99(m, 2H); 4.15(s, 2H); 4.23(q, 2H); 4.80(d, 1H); | 530.60 531 | INTA10 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| | | 6.81(dd, 1H); 7.41(d, 1H); 7.68-7.81(m, 2H); 8.65(s, 1H); 9.97(s, 1H); 10.79(s, 1H) ppm. | | |
| INTB38 | 2-Cyano-2-[3-ethyl-5-[1-{6-[2-(2-methoxy-ethoxy)-acetylamino]-pyridin-2-ylamino}-meth-(E/Z)-ylidene]-4-oxo-thiazolidin-(2-(E or Z))-ylidene]-N-(2-hydroxy-1,1-dimethyl-ethyl)-acetamide | (DMSO-d6, stored with K$_2$CO$_3$, main isomer): δ = 1.23(t, 3H); 1.30(s, 6H); 3.32(s, 3H); 3.38(d, 2H); 3.51(m, 2H), 3.68(m, 2H); 4.15(s, 2H); 4.20(q, 2H); 5.71(t, 1H); 6.71(s, 1H); 6.80(d, 1H); 7.69-7.80(m, 2H); 8.69(s, 1H); 9.95(s, 1H); 10.75(s, 1H) ppm. | 518.59 519 | INTA10 INTB1 |
| INTB39 | 2-Cyano-2-[3-ethyl-5-[1-(2-ethylamino-pyridin-4-ylamino)-meth-(E/Z)-ylidene]-4-oxo-thiazolidin-(2-(E or Z))-ylidene]-N-((1S,2S)-2-hydroxy-cyclopentyl)-acetamide | (DMSO-d6, stored with K$_2$CO$_3$, main isomer): δ = 1.11(t, 3H); 1.25(t, 3H); 1.53(m, 2H); 1.61(m, 2H); 1.77-2.02(m, 2H); 3.22(m, 2H); 3.84(m, 1H); 4.00(m, 1H); 4.22(q, 2H); 4.78(d, 1H); 6.24(s, 1H); 6.38-6.49(m, 2H); 7.41(d, 1H); 7.93(d, 1H); 8.00(d, 1H); 10.21(d, 1H) ppm. | 442.54 443 | INTA2 INTB1 |
| INTB40 | | (DMSO-d6, stored with K$_2$CO$_3$, main isomer): δ = | 430.53 431 | INTA2 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| | 2-Cyano-2-[3-ethyl-5-[1-(2-ethylamino-pyridin-4-ylainino)-meth-(E/Z)-ylidene]-4-oxo-thiazolidin-(2-(E or Z))-ylidene]-N-(2-hydroxy-1,1-dimethyl-ethyl)-acetamide | 1.11(t, 3H); 1.24(t, 3H); 1.30(s, 6H); 3.22(m, 2H); 3.28(d, 2H); 4.20(q, 2H); 5.20(t, 1H); 6.23(s, 1H); 6.37-6.49(m, 2H); 6.71(s, 1H); 7.83(d, 1H); 8.00(s, 1H); 10.20(s, 1H) ppm. | | |
| INTB41 | 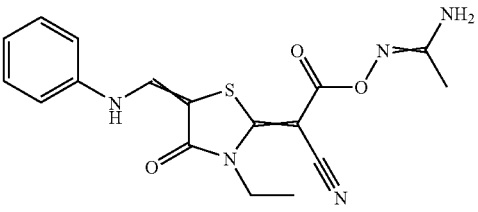 2-Cyano-2-[3-ethyl-4-oxo-5-[1-phenylamino-meth-(E/Z)-ylidene]-thiazolidin-(2-(E or Z))-ylidene]-acetamide (name approximated) | (DMSO-d6, stored with K$_2$CO$_3$, main isomer): δ = 1.27(t, 3H); 1.82(s, 3H); 4.26(q, 2H); 7.05-7.15(m, 1H); 7.28-7.42(m, 4H); 8.20(s, 1H); 10.58(s, 1H) ppm. | 371.42 372 | INTA11 INTB2 |
| INTB42 | 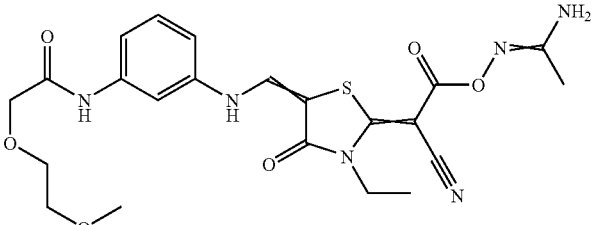 N-[3-[[[2-[(E or Z)-2-[[(1-Aminoethylidene)amino]oxy]-1-cyano-2-oxoethylidene]-3-ethyl-4-oxo-thiazolidin-5-(E/Z)-ylidene]methyl]amino]phenyl]-2-(2-methoxy-ethoxy)-acetamide | (DMSO-d6, stored with K$_2$CO$_3$, main isomer): δ = 1.27(t, 3H); 1.81(s, 3H); 3.31(s, 3H); 3.55(t, 2H); 3.68(t, 2H); 4.10(s, 2H); 4.26(q, 2H); 5.35-6.90(b, 2H); 6.99-7.17(m, 1H); 7.26-7.34(m, 2H); 7.77(s, 1H); 8.13(s, 1H); 9.73(s, 1H); 10.69(s, 1H) ppm. | 502.55 503 | INTA11 INTB2 |
| INTB43 | 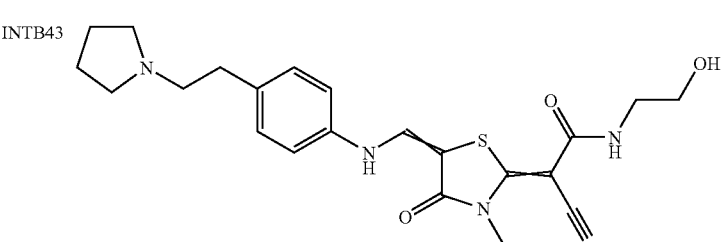 2-Cyano-2-[3-ethyl-4-oxo-5-[1-[4-(2-pyrrolidin-1-yl-ethyl)-phenylamino]-meth-(E/Z)-ylidene]-thiazolidin-(2-(E or Z))-ylidene]-N-(2-hydroxy-ethyl)- | (DMSO-d6, stored with K$_2$CO$_3$, main isomer): δ = 1.21(t, 3H); 1.68(m, 4H); 2.35-2.49(m, 2H); 2.54-2.62(m, 2H); | MW: 455.58 MS (ESI) [M + 1]$^+$: 456 | INTA4 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| | acetamide | 2.62-2.72(m, 2H); 3.24(q, 2H); 3.45(q, 2H); 4.20(q, 2H); 4.74(t, 1H); 7.06-7.19(m, 3H); 7.86-7.06(m, 2H); 8.20(s, 1H); 10.30(s, 1H) ppm. | | |
| INTB44 | 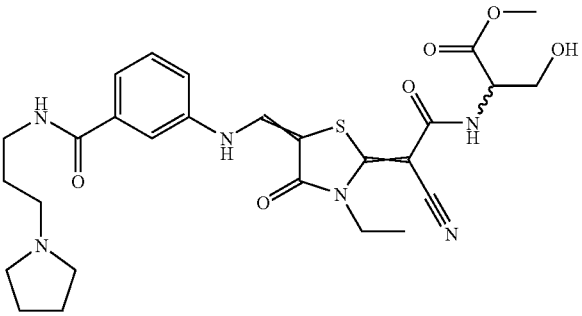<br>2-{2-Cyano-2-[3-ethyl-4-oxo-5-[1-[3-(3-pyrrolidin-1-yl-propylcarbamoyl)-phenylamino]-meth-(E/Z)-ylidene]-thiazolidin-(2-(E or Z))-ylidene]-acetylamino}-3-hydroxy-propionic acid methyl ester | (DMSO-d6, stored with K$_2$CO$_3$, main isomer): δ = 1.26(t, 3H); 1.60-1.79(m, 6H); 2.35-2.48(m, 6H); 3.19-3.48(m, 2H); 3.68(s, 3H); 3.70-3.89(m, 2H); 4.27(q, 2H); 4.45(m, 1H); 5.26(s, 1H); 7.32-7.46(m, 3H); 7.50(m, 1H); 7.72(s, 1H); 8.22(s, 1H); 8.61(t, 1H); 10.49(s, 1H) ppm. | MW: 570.66<br><br>MS (ESI) [M + 1]$^+$: 571 | INTA5 INTB1 |
| INTB45 | 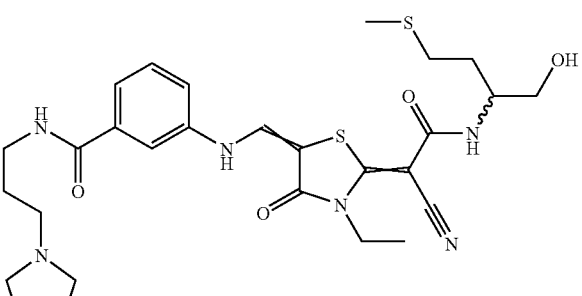<br>3-{[2-[1-Cyano-1-(1-hydroxymethyl-3-methylsulfanyl-propylcarbamoyl)-meth-(E or Z)-ylidene]-3-ethyl-4-oxo-thiazolidin-(5 -(E/Z))-ylidenemethyl]-amino}-N-(3-pyrrolidin-1-yl-propyl)-benzamide | (DMSO-d6, stored with K$_2$CO$_3$, main isomer): δ = 1.25(t, 3H); 1.60-1.90(m, 8H); 2.04(s, 3H); 2.32-2.48(m, 8H); 3.20-3.51(m, 4H); 3.98(m, 1H); 4.25(q, 2H), 4.85(s, 1H); 7.14(d, 1H); 7.33-7.46(m, 2H); 7.50(m, 1H); 7.71(s, 1H); 8.20(s, 1H); 8.62(t, 1H); 10.32(s, b, 1H) ppm. | MW: 570.66<br><br>MS (ESI) [M + 1]$^+$: 587 | INTA5 INTB1 |

TABLE 5-continued

| Example No. | Structure and Name | $^1$H-NMR | Molecular Weight/ MS (ESI) [M + 1]$^+$ | Educt/ Synthesis Analogously to |
|---|---|---|---|---|
| INTB46 | 3-{[2-[1-Cyano-1-(1-hydroxymethyl-butylcarbamoyl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ = 0.89(t, 3H); 1.18-1.39(m, 5H); 1.39-1.60(m, 2H); 1.60-1.79(m, 6H); 2.35-2.48(m, 6H); 3.20-3.50(m, 4H); 3.80-3.94(m, 1H); 4.23(q, 2H); 4.79(s, 1H); 6.99(d, 1H); 7.31-7.45(m, 2H), 7.49(d, 1H); 7.70(s, 1H); 8.20(s, 1H), 8.61(s, 1H); 10.39(s, b, 1H) ppm. | MW: 554.71 MS (ESI) [M + 1]$^+$: 555 | INTA5 INTB1 |
| INTB47 | 2-Cyano-2-[5-[1-[3-(2,2-dimethyl-propionylamino)-phenylamino]-meth-(E/Z)-ylidene]-3-ethyl-4-oxo-thiazolidin-(2-(E or Z))-ylidene]-N-(2-hydroxy-ethyl)-acetamide | (DMSO-d6, stored with K$_2$CO$_3$, main isomer): δ = 1.16-1.30(m, 12H); 3.28(q, 2H); 3.48(q, 2H); 4.24(q, 2H); 4.75(t, 1H); 6.91(d, 1H); 7.21(t, 1H); 7.34(d, 1H); 7.40(s, 1H); 7.68(s, 1H); 8.03(s, 1H); 9.21(s, 1H); 10.48(s, 1H) ppm. | MW: 457.55 MS (ESI) [M + 1]$^+$: 458 | INTA6 INTB1 |
| INTB48 | 2-Cyano-2-[3-ethyl-5-[1-{3-[(4aR,8aS)-2-(decahydro-isoquinolin-2-yl)-ethyl]-phenylamino}-meth-(E/Z)-ylidene]-4-oxo-thiazolidin-(2-(E or Z))-ylidene]-N-(2-hydroxy-1,1-dimethyl-ethyl)-acetamide | (DMSO-d6, stored with K$_2$CO$_3$, main isomer): δ = 0.70-1.30(m, 16H); 1.40-1.71(m, 6H); 1.88(t, 1H); 2.35-2.50(m, 2H); 2.60-2.71(m, 1H); 2.75(d, 1H); | | INTA12 INTB1 |

TABLE 5-continued

| Example No. | Structure and Name | ¹H-NMR | Molecular Weight/ MS (ESI) [M + 1]⁺ | Educt/ Synthesis Analogously to |
|---|---|---|---|---|
| | | 2.88(d, 1H); 3.33(d, 2H); 4.16(q, 2H); 5.14(t, 1H); 6.60(s, b, 1H); 6.86(d, 1H); 6.97-7.23(m, 3H); 8.09(s, 1H); 10.20(s, b, 1H) ppm. | | |

SYNTHESIS OF THE COMPOUNDS OF GENERAL FORMULA (1) ACCORDING TO THE INVENTION

Example 1

(4,4-Dimethyl-4,5-dihydro-oxazol-2-yl)-[3-ethyl-4-oxo-5-[1-[3-(2-pyrrolidin-1-yl-ethyl)-phenylamino]-meth-(E/Z)-ylidene]-thiazolidin-(2-(E or Z))-ylidene]-acetonitrile

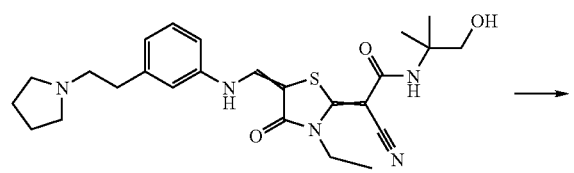

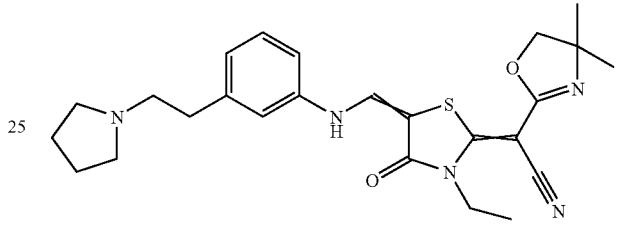

46 mg of the compound that is described under Intermediate Compound INTB1) is dissolved in 10 ml of tetrahydrofuran, mixed with 74 mg of Burgess' reagent and stirred for 2 hours at room temperature. 75 mg of sodium dihydrogen phosphate and 1 ml of dimethylformamide are added, and it is stirred for 4 hours at 40° C. The reaction mixture is mixed with saturated sodium bicarbonate solution and extracted in succession with ethyl acetate and a mixture that consists of dichloromethane and methanol (100:1). The organic phases are combined, dried on sodium sulfate, concentrated by evaporation, and after purification by chromatography on silica gel, 6 mg of the title compound is obtained.

1H-NMR (DMSO-d6, stored with $K_2CO_3$, main isomer): δ=1.18-1.33 (m, 9H); 1.68 (m, 4H); 2.45-2.54 (m, b, 4H); 2.56-2.67 (m, 2H); 2.67-2.78 (m, 2H); 4.00 (s, 2H); 4.24 (q, 2H); 6.92 (d, 1H); 7.08 (d, 1H); 7.14 (s, 1H); 7.22 (t, 1H); 8.15 (s, 1H); 10.38 (s, 1H) ppm.

The following compounds of general formula (I) are produced analogously to the above-described process.

TABLE 6

Compounds of General Formula (I)

| Example No. | Structure and Name | ¹H-NMR | Molecular Weight/ MS (ESI) [M + 1]⁺ | Educt/ Synthesis Analogously to |
|---|---|---|---|---|
| 2 | | (CDCl₃, main isomer): δ = | MW: 465.62 | INTB3/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| | (4,4-Dimethyl-4,5-dihydro-oxazol-2-yl)-[3-ethyl-4-oxo-5-[1-[4-(2-pyrrolidin-1-yl-ethyl)-phenylamino]-meth-(E/Z)-ylidene}-thiazolidin-(2-(E or Z))-ylidene]-acetonitrile | 1.37 (s, 6 H); 1.41 (t, 3 H); 1.69-1.88 (m, 4 H); 2.57 (m, 4 H); 2.62-2.73 (m, 2 H); 2.76-2.86 (m, 2 H), 4.03 (s, 2 H); 4.40 (q, 2 H); 6.96 (d, 2 H); 7.20 (d, 2 H); 7.51 (d, 1 H); 10.41 (d, 1 H) ppm. | MS (ESI) [M + 1]$^+$: 466 | |
| 3 | [3-Ethyl-4-oxo-5-[1-[4-(2-pyrrolidin-1-yl-ethyl)-phenylamino]-meth-(E/Z)-ylidene]-thiazolidin-(2-(E or Z))-ylidene]-((S)-4-methyl-4,5-dihydro-oxazol-2-yl)-acetonitrile | (DMSO-d6, stored with K$_2$CO$_3$, main isomer): δ = 1.10-1.34 (m, 6 H); 1.60-1.75 (m, 4 H); 2.37-2.48 (m, 4 H); 2.55-2.75 (m, 4 H); 3.85 (t, 1 H); 4.17-4.45 (m, 4 H); 7.09-7.27 (m, b, 4 H); 8.10 (s, 1 H); 10.40 (s, 1 H) ppm. | MW: 451.59 MS (ESI) [M + 1]$^+$: 452 | INTB4/1 |
| 4 | ((S)-4-Ethyl-4,5-dihydro-oxazol-2-yl)-[3-ethyl-4-oxo-5-[1-[4-(2-pyrrolidin-1-yl-ethyl)-phenylamino]-meth-(E/Z)-ylidene]-thiazolidin-(2-(E or Z))-ylidene]-acetonitrile | (CDCl$_3$, main isomer): δ = 1.01 (t, 3 H); 1.40 (t, 3 H); 1.53-1.70 (m, 2 H); 1.76-1.91 (m, 4 H); 2.55-2.68 (m, 4 H); 2.68-2.79 (m, 2 H); 2.79-2.91 (m, 2 H); 3.97 (t, 1 H); 4.19-4.33 (m, 1 H); 4.35-4.49 (m, 3 H); 6.96 (d, 2 H); 7.20 (d, 2 H); 7.51 (d, 1 H); 10.41 (d, 1 H) ppm. | MW: 465.62 MS (ESI) [M + 1]$^+$: 466 | INTB5/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| 5 | 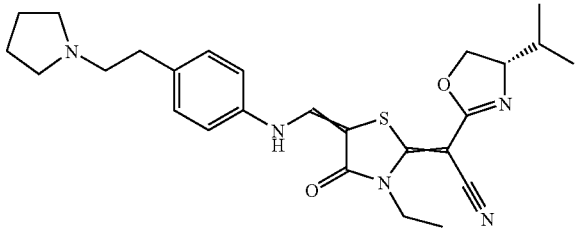<br><br>[3-Ethyl-4-oxo-5-[1-[4-(2-pyrrolidin-1-yl-ethyl)-phenylamino]-meth-(E/Z)-ylidene]-thiazolidin-(2-(E or Z))-ylidene]-((S)-4-isopropyl-4,5-dihydro-oxazol-2-yl)-acetonitrile | (DMSO-d6, stored with K$_2$CO$_3$, main isomer): δ =<br>0.88 (d, 3 H);<br>0.96 (d, 3 H);<br>1.26 (t, 3 H);<br>1.61-1.81 (m, 5 H);<br>2.39-2.49 (m, 4 H);<br>2.53-2.65 (m, 2 H),<br>2.65-2.76 (m, 2 H),<br>4.00-4.15 (m, 2 H);<br>4.18-4.36 (m, 3 H),<br>7.13-7.30 (m, 4 H);<br>8.10 (s, 1 H);<br>10.38 (s, 1 H) ppm. | MW: 479.65<br><br>MS (ESI)<br>[M + 1]$^+$: 480 | INTB6/1 |
| 6 | 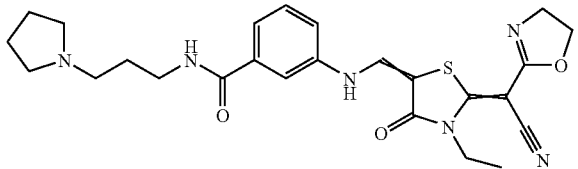<br><br>3-{2-[1-Cyano-1-(4,5-dihydro-oxazol-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ =<br>1.25 (t, 3 H);<br>1.60-1.80 (m, b, 6 H);<br>2.39-2.55 (m, b, 6 H);<br>3.25-3.39 (m, b, 2 H);<br>4.00 (t, 2 H);<br>4.25 (q, 2 H);<br>4.31 (t, 2 H);<br>7.33-7.47 (m, 2 H);<br>7.47-7.57 (m, 1 H);<br>7.76 (s, 1 H);<br>8.24 (s, 1 H);<br>8.63 (t, 1 H);<br>10.50 (s, b, 1 H) ppm. | MW: 494.61<br><br>MS (ESI)<br>[M + 1]$^+$: 495 | INTB7/1 |
| 7 | 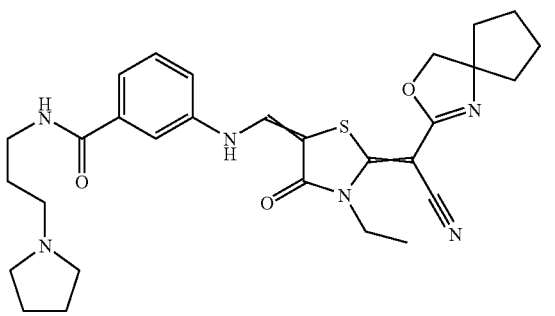<br><br>3-{2-[1-Cyano-1-(3-oxa-1-aza-spiro[4.4]non-1-en-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ =<br>1.26 (t, 3 H);<br>1.57-1.92 (m, 14 H);<br>2.37-2.51 (m, 6 H);<br>3.21-3.32 (m, 2 H);<br>4.15 (s, 2 H);<br>4.25 (q, 2 H);<br>7.30-7.48 (m, 2 H);<br>7.52 (s, 1 H); | MW: 548.70<br><br>MS (ESI)<br>[M + 1]$^+$: 549 | INTB8/1 |

TABLE 6-continued

Compounds of General Formula (I)

| Example No. | Structure and Name | $^1$H-NMR | Molecular Weight/ MS (ESI) $[M + 1]^+$ | Educt/ Synthesis Analogously to |
|---|---|---|---|---|
| | | 7.72 (s, 1 H); 8.23 (s, 1 H); 8.62 (t, 1 H); 10.49 (s, 1 H) ppm. | | |
| 8 | 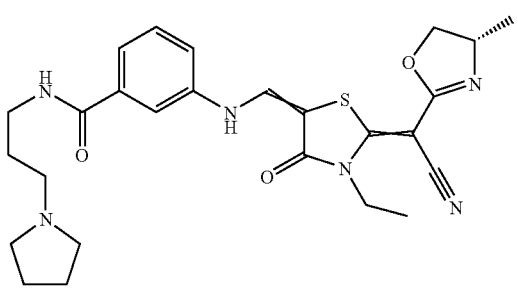 3-{[2-[1-Cyano-1-((S)-4-methyl-4,5-dihydro-oxazol-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ = 1.13-1.29 (m, 6 H); 1.60-1.78 (m, 6 H); 2.34-2.50 (m, 6 H); 3.18-3.30 (m, 2 H); 3.65-3.73 (m, 1 H); 4.13-4.36 (m, 4 H); 7.09 (d, 1 H), 7.25 (t, 1 H); 7.34 (d, 1 H); 7.45 (s, 1 H); 8.39 (s, 1 H); 8.52 (t, 1 H); 10.50 (s, 1 H) ppm. | MW: 508.64  MS (ESI) $[M + 1]^+$: 509 | INTB9/1 |
| 9 | 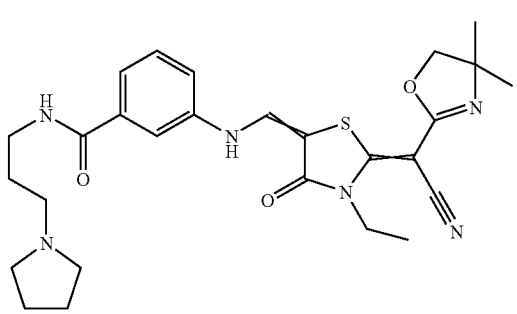 3-{[2-[1-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ = 1.15-1.38 (m, 9 H); 1.76-2.07 (m, 6 H); 2.84-3.24 (m, 6 H); 3.24-3.37 (m, 2 H); 4.01 (s, 2 H); 4.25 (q, 2 H); 7.08 (s, 1 H); 7.31 (s, 1 H); 7.37-7.50 (m, 2 H); 8.15 (m, 1 H); 8.34 (s, 1 H); 10.51 (d, 1 H) ppm. | MW: 522.67  MS (ESI) $[M + 1]^+$: 523 | INTB10/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| 10 | 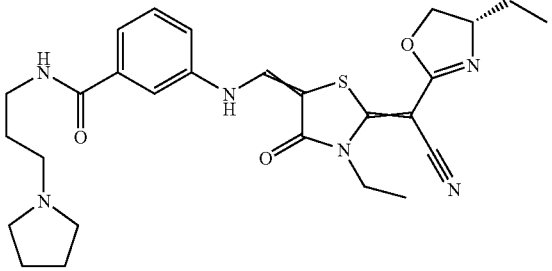<br><br>3-{[2-[1-Cyano-1-((S)-4-ethyl-4,5-dihydro-oxazol-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ =<br>0.93 (t, 3 H);<br>1.23 (t, 3 H);<br>1.45-1.61 (m, 2 H);<br>1.61-1.78 (m, 6 H);<br>2.33-2.50 (m, 6 H);<br>3.20-3.31 (m, 2 H);<br>3.92 (m, 1 H);<br>4.10-4.38 (m, 4 H);<br>7.16-7.72 (m, 4 H);<br>8.30 (s, 1 H);<br>8.59 (s, 1 H);<br>10.51 (s, 1 H) ppm. | MW: 522.67<br><br>MS (ESI) [M + 1]$^+$: 523 | INTB11/1 |
| 11 | 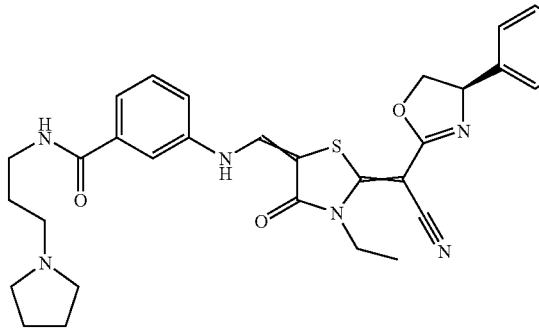<br><br>3-{[2-[1-Cyano-1-((R)-4-phenyl-4,5-dihydro-oxazol-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide | (DMSO-d6, stored with K$_2$CO$_3$, main isomer): δ =<br>1.29 (t, 3 H);<br>1.59-1.80 (m, 6 H);<br>2.32-2.50 (m, 6 H);<br>3.18-3.31 (m, 2 H);<br>4.17 (t, 1 H);<br>4.31 (q, 2 H);<br>4.75 (t, 1 H);<br>5.42 (t, 1 H);<br>7.20-7.58 (m, 8 H);<br>7.71 (s, 1 H);<br>8.25 (s, 1 H),<br>8.61 (t, 1 H);<br>10.50 (s, 1 H) ppm. | MW: 570.71<br><br>MS (ESI) [M + 1]$^+$: 571 | INTB12/1 |
| 12 | 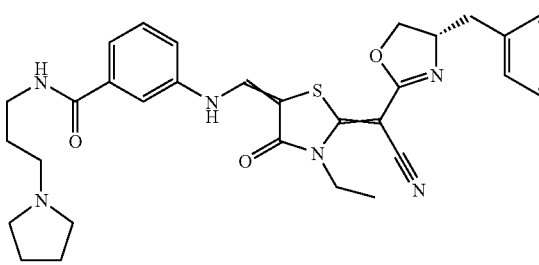 | (DMSO-d6, stored with K$_2$CO$_3$, main isomer): δ = | MW: 584.74 | INTB13/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| | 3-{[2-[1-((S)-4-Benzyl-4,5-dihydro-oxazol-2-yl)-1-cyano-meth-(E or Z)-ylidene]-3-ethyl-4-oxo-thiazolidin-(5-(E/Z))-ylidenemethyl]-amino}-N-(3-pyrrolidin-1-yl-propyl)-benzamide | 1.25 (t, 3 H); 1.59-1.82 (m, 6 H); 2.32-2.50 (m, 6 H); 2.65-2.80 (m, 1 H); 3.05 (dd, 1 H); 3.20-3.31 (m, 2 H); 4.03 (t, 1 H); 4.17-4.33 (m, 3 H); 4.49-4.62 (m, 1 H); 6.98-7.55 (m, 10 H); 8.20 (s, 1 H); 10.51 (s, 1 H) ppm. | MS (ESI) [M + 1]$^+$: 585 | |
| 13 | N-(3-{[2-[1-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 1.14-1.35 (m, 18 H); 3.99 (d, 2 H); 4.24 (q, 2 H); 6.94 (d, 1 H); 7.25 (t, 1 H); 7.35 (d, 1 H); 7.70 (s, 1 H); 8.08 (s, 1 H); 9.22 (s, 1 H); 10.50 (s, 1 H) ppm. | MW: 467.59 MS (ESI) [M + 1]$^+$: 468 | INTB14/1 |
| 14 | N-(3-{[2-[(3aS,6aR)-1-Cyano-1-4,5,6,6a-tetrahydro-3aH-cyclopentaoxazol-2-yl-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 1.14-1.29 (m, 12 H); 1.29-1.48 (m, 1 H); 1.53-1.85 (m, 4 H); 1.85-1.98 (m, 1 H); 4.23 (q, 2 H); 4.68 (t, 1 H); 5.03 (t, 1 H); 6.92 (d, 1 H); 7.23 (t, 1 H); 7.35 (d, 1 H); 7.69 (s, 1 H), 8.08 (s, 1 H); 9.23 (s, 1 H); 10.49 (s, 1 H) ppm. | MW: 467.60 MS (ESI) [M + 1]$^+$: 480 | INTB15/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| 15 | N-(3-{[2-[1-Cyano-1-(5-methyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 1.18-1.29 (m, 12 H); 1.33 (d, 3 H); 3.52 (dd, 1 H); 4.10 (dd, 1 H); 4.25 (q, 2 H); 4.79 (m, 1 H); 6.94 (d, 1 H); 7.24 (t, 1 H); 7.38 (d, 1 H); 7.72 (s, 1 H); 8.06 (s, 1 H); 10.49 (s, 1 H) ppm. | MW: 453.56 MS (ESI) [M + 1]$^+$: 454 | INTB16/1 |
| 16 | N-(3-{[2-[1-Cyano-1-((S)-4-ethyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 0.94 (t, 3 H); 1.14-1.33 (m, 12 H); 1.49-1.66 (m, 2 H); 3.93-4.05 (m, 1 H); 4.16-4.30 (m, 3 H); 4.36 (t, 1 H); 6.86 (d, 1 H); 7.25 (t, 1 H); 7.37 (d, 1 H); 7.72 (s, 1 H); 8.05 (d, 1 H); 9.25 (s, 1 H); 10.50 (d, 1 H) ppm. | MW: 467.59 MS (ESI) [M + 1]$^+$: 468 | INTB17/1 |
| 17 | N-(3-{[2-[1-Cyano-1-(4-propyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 0.93 (t, 3 H); 1.13-1.30 (m, 12 H); 1.31-1.64 (m, 4 H); 3.97 (t, 1 H); 4.19-4.31 (m, 3 H); 4.38 (t, 1 H); 6.95 (d, 1 H); 7.25 (t, 1 H); 7.38 (d, 1 H); 7.73 (s, 1 H), 8.06 (d, 1 H); | MW: 481.62 MS (ESI) [M + 1]$^+$: 482 | INTB18/1 |

TABLE 6-continued

Compounds of General Formula (I)

| Example No. | Structure and Name | ¹H-NMR | Molecular Weight/ MS (ESI) [M + 1]⁺ | Educt/ Synthesis Analogously to |
|---|---|---|---|---|
| | | 9.25 (s, 1 H); 10.50 (d, 1 H) ppm. | | |
| 18 | 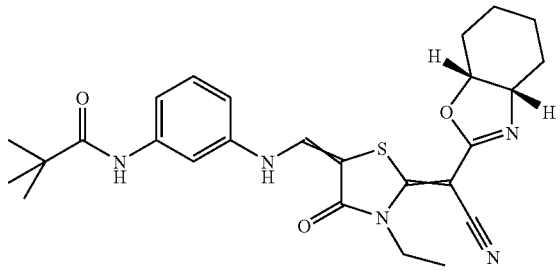 N-(3-{[2-[(3aS,7aR)-1-Cyano-1-3a,4,5,6,7,7a-hexahydro-benzooxazol-2-yl-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K₂CO₃, main isomer): δ = 1.16-1.30 (m, 12 H); 1.32-1.51 (m, 4 H); 1.72-1.90 (m, 4 H); 4.10 (m, 1 H); 4.26 (q, 2 H); 4.60 (m, 1 H); 6.95 (d, 1 H); 7.24 (t, 1 H); 7.37 (d, 1 H); 7.73 (s, 1 H); 8.06 (d, 1 H); 9.24 (s, 1 H); 10.50 (d, 1 H) ppm. | MW: 493.63 MS (ESI) [M + 1]⁺: 494 | INTB19/1 |
| 19 | 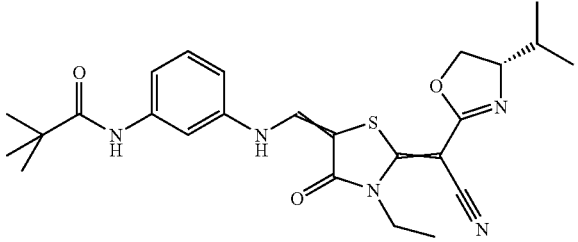 N-(3-{[2-[1-Cyano-1-((S)-4-isopropyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K₂CO₃, main isomer): δ = 0.90 (d, 3 H); 0.99 (d, 3 H); 1.13-1.33 (m, 12 H); 1.73 (m, 1 H); 4.00-4.15 (m, 2 H); 4.17-4.38 (m, 3 H); 7.05 (d, 1 H); 7.25 (t, 1 H); 7.38 (d, 1 H); 7.73 (s, 1 H); 8.08 (d, 1 H); 9.26 (s, 1 H); 10.50 (d, 1 H) ppm. | MW: 481.62 MS (ESI) [M + 1]⁺: 482 | INTB20/1 |
| 20 | 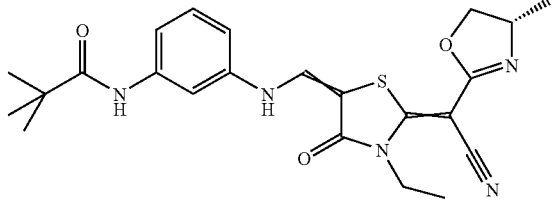 N-(3-{[2-[1-Cyano-1-((S)-4-methyl-4,5-dihydro-oxazol-2-yl)-meth-(E or Z)-ylidene]-3-ethyl-4-oxo-thiazolidin-(5-(E/Z))-ylidenemethyl]-amino- | (DMSO-d6, stored with K₂CO₃, main isomer): δ = 1.12-1.30 (m, 15); 3.72-3.87 (m, 1 H); 4.17-4.42 (m, 4 H); 6.83 (s, b, 1 H); | MW: 453.56 MS (ESI) [M + 1]⁺: 454 | INTB21/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| | phenyl)-2,2-dimethyl-propionamide | 7.18 (t, 1 H); 7.32 (d, 1 H); 7.56 (s, 1 H); 8.17 (s, 1 H); 9.25 (s, 1 H); 10.51 (s, 1 H) ppm. | | |
| 21 | N-(3-{[2-[1-Cyano-1-(3-oxa-1-aza-spiro[4.4]non-1-en-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 1.14-1.31 (m, 12 H); 1.57-1.74 (m, 4 H); 1.74-1.90 (m, 4 H); 4.13 (s, 2 H); 4.25 (q, 2 H); 6.96 (d, 1 H); 7.27 (t, 1 H); 7.38 (d, 1 H); 7.75 (s, 1 H); 8.15 (d, 1 H); 9.26 (s, 1 H); 10.43 (d, 1 H) ppm. | MW: 493.63 MS (ESI) [M + 1]$^+$: 494 | INTB22/1 |
| 22 | 2-{Cyano-[5-[1-[3-(2,2-dimethyl-propionylamino)-phenylamino]-meth-(E/Z)-ylidene]-3-ethyl-4-oxo-thiazolidin-(2-(E or Z))-ylidene]-methyl}-4,5-dihydro-oxazole-4-carboxylic acid methyl ester | (DMSO-d6, stored with K$_2$CO$_3$, main isomer): δ = 1.15-1.31 (m, 9 H); 3.71 (s, 3 H); 4.27 (q, 2 H); 4.44-4.56 (m, 2 H); 4.96 (t, 1 H); 6.95 (d, 1 H); 7.25 (t, 1 H); 7.38 (d, 1 H); 7.75 (s, 1 H); 8.10 (d, 1 H); 9.26 (s, 1 H); 10.54 (d, 1 H) ppm. | MW: 497.57 MS (ESI) [M + 1]$^+$: 498 | INTB23/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| 23 | 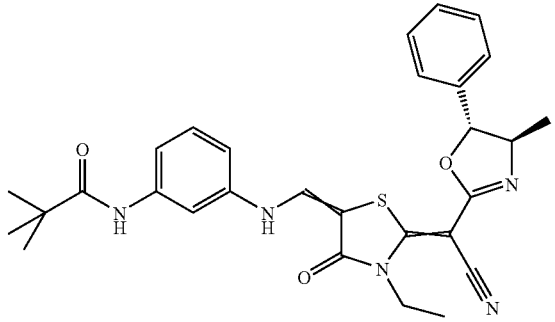<br>N-(3-{[2-[1-Cyano-1-((4R,5R)-4-methyl-5-phenyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ =<br>1.20-1.33 (m, 1 2 H);<br>1.40 (d, 1 H);<br>4.13 (m, 1 H);<br>4.29 (q, 2 H);<br>5.27 (d, 1 H);<br>6.95 (d, 1 H);<br>7.25 (t, 1 H);<br>7.32-7.48 (m, 6 H);<br>7.75 (s, 1 H);<br>8.10 (d, 1 H);<br>9.25 (s, 1 H);<br>10.53 (d, 1 H) ppm. | MW: 529.66<br><br>MS (ESI) [M + 1]$^+$: 530 | INTB24/1 |
| 24 | 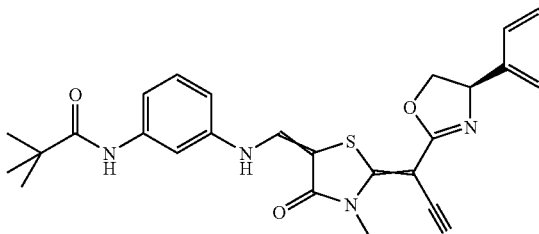<br>N-(3-{[2-[1-Cyano-1-((R)-4-phenyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ =<br>1.17-1.35 (m, 12 H);<br>4.07 (t, 1 H);<br>4.30 (q, 2 H);<br>4.74 (t, 1 H);<br>5.43 (t, 1 H);<br>6.91 (d, 1 H);<br>7.18-7.43 (m, 7 H);<br>7.70 (s, 1 H);<br>8.08 (d, 1 H);<br>9.24 (s, 1 H);<br>10.51 (d, 1 H) ppm. | MW: 515.64<br><br>MS (ESI) [M + 1]$^+$: 516 | INTB25/1 |
| 25 | 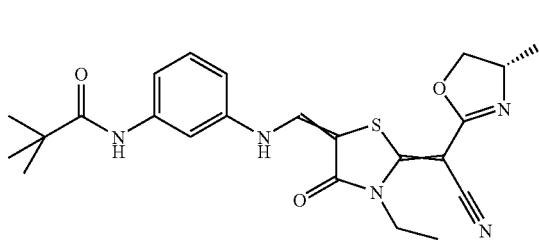<br>N-(3-{[2-[1-((S)-4-tert-Butyl-4,5-dihydro-oxazol-2-yl)-1-cyano-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ =<br>0.91 (s, 9 H);<br>1.15-1.34 (m, 12 H);<br>3.97-4.07 (m, 1 H);<br>4.13-4.33 (m, 4 H);<br>6.96 (d, 1 H);<br>7.26 (t, 1 H); | MW: 495.65<br><br>MS (ESI) [M + 1]$^+$: 496 | INTB26/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| | | 7.38 (d, 1 H); 7.23 (s, 1 H); 8.05 (d, 1 H); 9.25 (s, 1 H); 10.49 (d, 1 H) ppm. | | |
| 26 | 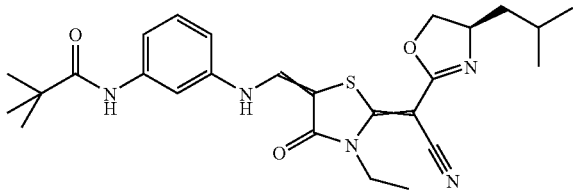 N-(3-{[2-[1-Cyano-1-((R)-4-isobutyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 0.89–1.00 (m, 6 H); 1.14–1.41 (m, 13 H); 1.49–1.61 (m, 1 H); 1.69–1.82 (m, 1 H); 3.92 (t, 1 H); 4.19–4.35 (m, 3 H); 4.40 (t, 1 H); 6.94 (d, 1 H); 7.25 (t, 1 H); 7.37 (d, 1 H); 7.72 (s, 1 H); 8.08 (s, 1 H); 9.26 (s, 1 H); 10.50 (s, 1 H) ppm. | MW: 495.65 MS (ESI) [M + 1]$^+$: 496 | INTB27/1 |
| 27 | 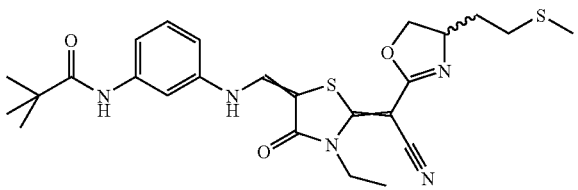 N-(3-{[2-[1-Cyano-1-[4-(2-methylsulfanyl-ethyl)-4,5-dihydro-oxazol-2-yl]-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 1.15–1.33 (m, 12 H); 1.79 (q, 2 H); 2.61 (m, 2 H); 4.03 (t, 1 H); 4.26 (q, 2 H); 4.30–4.44 (m, 2 H); 6.95 (d, 1 H); 7.25 (t, 1 H); 7.38 (d, 1 H); 7.75 (s, 1 H); 8.06 (d, 1 H); 9.26 (s, 1 H); 10.50 (d, 1 H) ppm. | MW: 513.68 MS (ESI) [M + 1]$^+$: 514 | INTB28/1 |
| 28 | 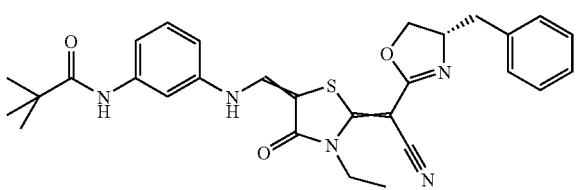 N-(3-{[2-[1-((S)-4-Benzyl-4,5-dihydro-oxazol-2-yl)-1-cyano-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 1.16–1.31 (m, 12 H); 2.73 (dd, 1 H); 3.07 (dd, 1 H); 3.97–4.09 (m, 1 H); 4.19–4.33 (m, 3 H), 4.57 (m, 1 H); 6.97 (d, 1 H); | MW: 529.66 MS (ESI) [M + 1]$^+$: 530 | INTB29/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| | | 7.19-7.41 (m, 7 H); 7.75 (s, 1 H); 8.09 (d, 1 H); 9.26 (s, 1 H); 10.57 (d, 1 H) ppm. | | |
| 29 | 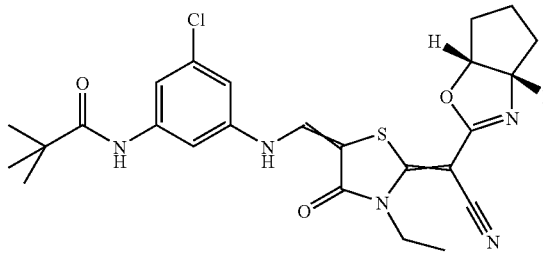<br>N-(3-Chloro-5-{[2-[(3aS,6aR)-1-cyano-1-4,5,6,6a-tetrahydro-3aH-cyclopentaoxazol-2-yl-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 1.13-1.41 (m, 13 H); 1.53-1.82 (m, 4 H); 1.82-1.98 (m, 1 H); 4.23 (q, 2 H); 4.69 (t, 1 H); 5.04 (t, 1 H); 7.00 (s, 1 H); 7.51 (s, 1 H); 7.64 (s, 1 H); 8.05 (s, 1 H); 9.36 (s, 1 H); 10.43 (s, 1 H) ppm. | MW: 514.05<br><br>MS (ESI) [M + 1]$^+$: 515 | INTB30/1 |
| 30 | 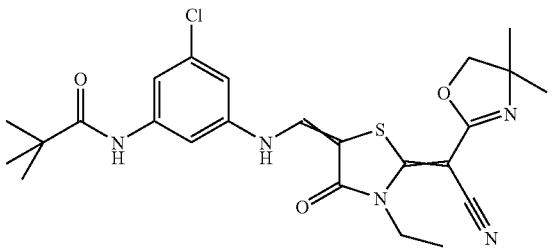<br>N-(3-Chloro-5-{[2-[1-cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide | (DMSO-d6, stored with K$_2$CO$_3$, main isomer): δ = 1.13-1.35 (m, 18 H); 4.00 (s, 2 H); 4.22 (q, 2 H); 7.01 (s, 1 H); 7.50 (s, 1 H); 7.64 (s, 1 H); 8.07 (s, 1 H); 9.35 (s, 1 H); 10.43 (s, 1 H) ppm. | MW: 502.04<br><br>MS (ESI) [M + 1]$^+$: 503 | INTB31/1 |
| 31 | 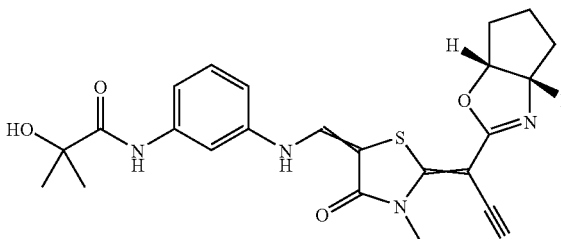<br>N-(3-{[2-[(3aS,6aR)-1-Cyano-1-4,5,6,6a-tetrahydro-3aH-cyclopentaoxazol-2-yl-meth-(E or Z)-ylidene]-3-ethyl-4-oxo-thiazolidin-(5- | (DMSO-d6, stored with K$_2$CO$_3$, main isomer): δ = 1.17-1.42 (m, 1 H); 1.25 (t, 3 H); 1.37 (s, 6 H); 1.52-1.82 (m, 1 H); | MW: 481.57<br><br>MS (ESI) [M + 1]$^+$: 482 | INTB32/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| | (E/Z))-ylidenemethyl]-amino}-phenyl)-2-hydroxy-2-methyl-propionamide | 1.82-1.98 (m, 1 H); 4.25 (q, 2 H); 4.69 (t, 1 H); 5.04 (t, 1 H); 5.25 (s, 1 H); 6.95 (d, 1 H), 7.24 (t, 1 H); 7.43 (d, 1 H); 7.84 (s, 1 H); 8.08 (s, 1 H); 9.63 (s, 1 H); 10.47 (s, 1 H) ppm. | | |
| 32 | N-(3-{[2-[(3aS,6aR)-1-Cyano-1-4,5,6,6a-tetrahydro-3aH-cyclopentaoxazol-2-yl-meth-(E or Z)-ylidene]-3-ethyl-4-oxo-thiazolidin-(5-(E/Z))-ylidenemethyl]-amino}-phenyl)-2-(2-methoxy-ethoxy)-acetamide | (DMSO-d6, stored with K$_2$CO$_3$, main isomer): δ = 1.18-1.46 (m, 1 H); 1.24 (t, 3 H); 1.50-1.83 (m, 4 H); 1.83-1.98 (m, 1 H); 3.30 (s, 3 H); 3.54 (t, 2 H); 3.68 (t, 2 H); 4.09 (s, 2 H); 4.24 (q, 2 H); 4.69 (t, 1 H); 5.05 (t, 1 H); 6.94-7.04 (m, 1 H); 7.22-7.31 (m, 2 H); 7.74 (s, 1 H); 8.05 (s, 1 H); 9.70 (s, 1 H); 10.51 (s, 1 H) ppm. | MW: 511.60  MS (ESI) [M + 1]$^+$: 512 | INTB33/1 |
| 33 | N-(3-{[2-[1-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2-(2-methoxy-ethoxy)-acetamide | (DMSO-d6, stored with K$_2$CO$_3$, main isomer): δ = 1.25 (t, 3 H); 1.30 (m, 6 H); 3.30 (s, 3 H); 3.54 (t, 2 H); 3.68 (t, 2 H); 4.01 (s, 2 H); 4.19 (s, 2 H); 4.24 (q, 2 H); 6.96-7.03 (m, 1 H); 7.23-7.31 (m, 2 H); 7.78 (s, 1 H); 8.06 (s, 1 H); 9.71 (s, 1 H); 10.52 (s, 1 H) ppm. | MW: 499.59  MS (ESI) [M + 1]$^+$: 500 | INTB34/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| 34 | 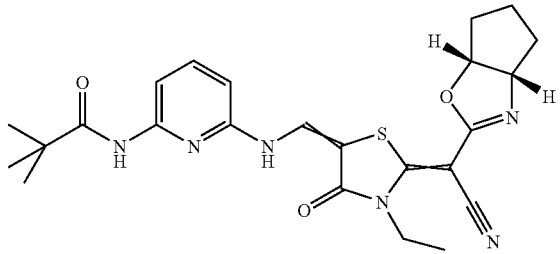<br>N-(6-{2-[(3aS,6aR)-1-Cyano-1-4,5,6,6a-tetrahydro-3aH-cyclopentaoxazol-2-yl-meth-(E or Z)-ylidene]-3-ethyl-4-oxo-thiazolidin-(5-(E/Z))-ylidenemethyl]-amino}-pyridin-2-yl)-2,2-dimethyl-propionamide | (DMSO-d6, stored with K$_2$CO$_3$, main isomer): δ =<br>1.15-1.45 (m, 13 H);<br>1.53-1.82 (m, 4 H);<br>1.82-1.98 (m, 1 H);<br>4.24 (q, 2 H);<br>4.69 (t, 1 H);<br>5.04 (t, 1 H);<br>6.81 (dd, 1 H);<br>7.66-7.78 (m, 2 H);<br>8.79 (d, 1 H);<br>9.70 (s, 1 H);<br>10.77 (d, 1 H) ppm. | MW: 480.59<br><br>MS (ESI)<br>[M + 1]$^+$: 481 | INTB35/1 |
| 35 | 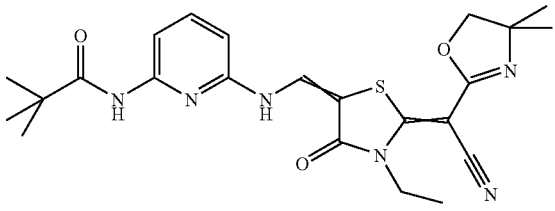<br>N-(6-{2-[1-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-pyridin-2-yl)-2,2-dimethyl-propionamide | (DMSO-d6, stored with K$_2$CO$_3$, main isomer): δ =<br>1.20-1.29 (m, 12 H);<br>1.30 (s, 6 H);<br>4.01 (s, 2 H);<br>4.25 (q, 2 H);<br>6.81 (dd, 1 H);<br>7.68-7.77 (m, 2 H);<br>8.80 (s, 1 H);<br>9.70 (s, 1 H);<br>10.80 (s, 1 H) ppm. | MW: 468.58<br><br>MS (ESI)<br>[M + 1]$^+$: 469 | INTB36/1 |
| 36 | 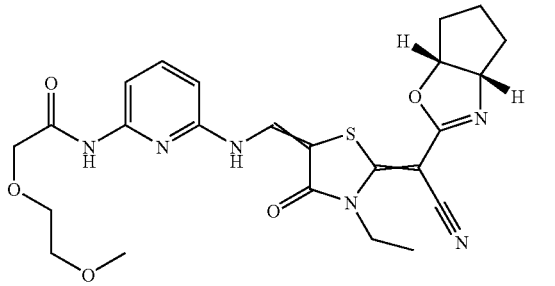<br>N-(6-{2-[(3aS,6aR)-1-Cyano-1-4,5,6,6a-tetrahydro-3aH-cyclopentaoxazol-2-yl-meth-(E or Z)-ylidene]-3-ethyl-4-oxo-thiazolidin-(5-(E/Z))-ylidenemethyl]-amino}-pyridin-2-yl)-2-(2-methoxy-ethoxy)-acetamide | (DMSO-d6, stored with K$_2$CO$_3$, main isomer): δ =<br>1.15-1.49 (m, 4 H);<br>1.49-1.82 (m, 4 H);<br>1.82-1.98 (m, 1 H);<br>3.32 (s, 3 H);<br>3.51 (t, 2 H);<br>3.69 (t, 2 H);<br>4.14 (d, 2 H);<br>4.22 (q, 2 H);<br>4.68 (t, 1 H);<br>5.03 (t, 1 H);<br>6.80 (d, 1 H); | MW: 512.59<br><br>MS (ESI)<br>[M + 1]$^+$: 513 | INTB37/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| | | 7.66-7.79 (m, 2 H); 8.74 (s, 1 H); 9.94 (s, 1 H); 10.82 (s, 1 H) ppm. | | |
| 37 | 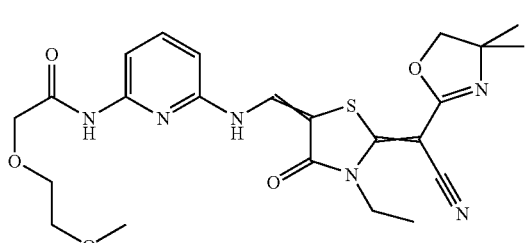<br><br>N-(6-{[2-[1-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-pyridin-2-yl)-2-(2-methoxy-ethoxy)-acetamide | (DMSO-d6, stored with K$_2$CO$_3$, main isomer): δ = 1.25 (t, 3 H); 1.30 (s, 6 H); 3.32 (s, 3 H); 3.52 (t, 2 H); 3.69 (t, 2 H); 4.01 (s, 2 H); 4.16 (s, 2 H); 4.24 (q, 2 H); 6.83 (dd, 1 H); 7.72-7.80 (m, 2 H); 8.72 (s, 1 H); 9.98 (s, 1 H); 10.87 (s, 1 H) ppm. | MW: 500.58<br><br>MS (ESI) [M + 1]$^+$: 501 | INTB38/1 |
| 38 | 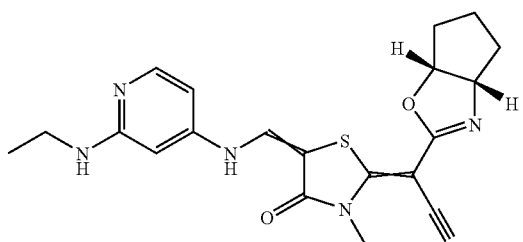<br><br>[3-Ethyl-5-[1-(2-ethylamino-pyridin-4-ylamino)-meth-(E/Z)-ylidene]-4-oxo-thiazolidin-(2-(E or Z))-ylidene]-(3aS,6aR)-4,5,6,6a-tetrahydro-3aH-cyclopentaoxazol-2-yl-acetonitrile | (DMSO-d6, stored with K$_2$CO$_3$, main isomer): δ = 1.12 (t, 3 H); 1.25 (t, 3 H); 1.28-1.42 (m, 1 H); 1.52-1.82 (m, 4 H); 1.83-1.97 (m, 1 H); 3.22 (pentuplet, 2 H); 4.23 (q, 2 H); 4.70 (t, 1 H); 5.05 (t, 1 H); 6.23 (s, 1 H); 6.38-6.50 (m, 2 H), 7.82 (d, 1 H); 8.06 (s, 1 H); 10.33 (s, 1 H) ppm. | MW: 424.53<br><br>MS (ESI) [M + 1]$^+$: 425 | INTB39/1 |
| 39 | 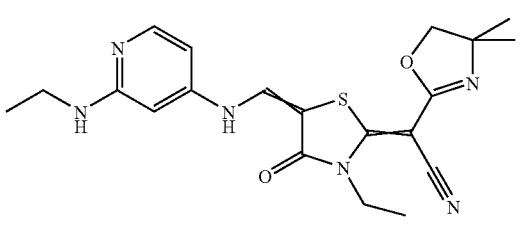<br><br>(4,4-Dimethyl-4,5-dihydro-oxazol-2-yl)-[3-ethyl-5-[1-(2-ethylamino- | (DMSO-d6, stored with K$_2$CO$_3$, main isomer): δ = 1.20 (t, 3 H); 1.31 (t, 3 H); | MW: 412.52<br><br>MS (ESI) | INTB40/1 |

TABLE 6-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| | pyridin-4-ylamino)-meth-(E/Z)-ylidene]-4-oxo-thiazolidin-(2-(E or Z))-ylidene]-acetonitrile | 1.36 (s, 6 H); 3.30 (pentuplet, 2 H); 4.08 (s, 2 H); 4.30 (q, 2 H); 6.31 (s, 1 H); 6.46-6.57 (m, 2 H); 7.90 (d, 1 H); 8.10 (d, 1 H); 10.42 (d, 1 H) ppm. | [M + 1]$^+$: 413 | |
| 40 | (4,4-Dimethyl-4,5-dihydro-oxazol-2-yl)-[3-ethyl-5-[1-{3-[(4aR,8aS)-2-(decahydro-isoquinolin-2-yl)-ethyl]-phenylamino}-meth-(E/Z)-ylidene]-4-oxo-thiazolidin-(2-(E or Z))-ylidene]-acetonitrile | (DMSO-d6, stored with K$_2$CO$_3$, Main Isomer): δ = 0.70-1.33 (m, 16 H); 1.36-1.72 (m, 6 H); 1.89 (t, 1 H); 2.35-2.50 (m, 2 H); 2.59-2.95 (m, 4 H); 3.95 (s, 2 H); 4.19 (q, 2 H); 6.87 (d, 1 H); 6.97-7.25 (m, 3 H); 8.10 (s, 1 H); 10.32 (s, b, 1 H) ppm. | MW: 533.74 MS (ESI) [M + 1]$^+$: 534 | INTB48/1 |

SYNTHESIS OF ADDITIONAL COMPOUNDS OF GENERAL FORMULA (1) ACCORDING TO THE INVENTION

Example 41

2-{Cyano-[5-1-[[3-(2,2-dimethyl-propionylamino)-phenylamino]-meth-(E/Z)-ylidene]-3-ethyl-4-oxo-thiazolidin-(2-(E or Z))-ylidene]-methyl}-oxazole-4-carboxylic acid methyl ester

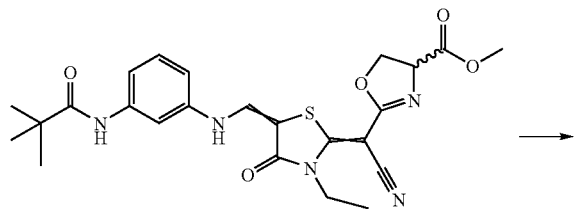

→

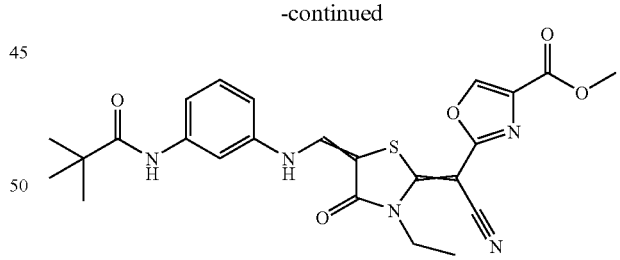

100 mg of the compound that is described under Example 22) is dissolved in 6 ml of benzene. 54 mg of DDQ is added, and it is stirred under reflux for 10 minutes. The reaction mixture is mixed with water and extracted with ethyl acetate. The organic solution is washed with saturated sodium chloride solution, dried on sodium sulfate, concentrated by evaporation, and after purification by chromatography on silica gel and subsequent crystallization from ethanol, 11 mg of the title compound is obtained as a pH-dependent 5-(E/Z)-isomer mixture.

1H-NMR (DMSO-d6, stored with K$_2$CO$_3$, main isomer): δ=1.24 (s, 9H); 1.30 (t, 3H); 3.86 (s, 3H); 4.30 (q, 2H);

6.89-7.02 (m, 1H); 7.19-7.33 (m, 2H); 7.39 (d, 1H); 7.73 (s, 1H); 8.17 (s, 1H); 8.86 (s, 1H); 9.26 (s, 1H); 10.81 (s, 1H) ppm.

Example 42

N-(3-{[2-[1-Cyano-1-(3-methyl-[1,2,4]oxadiazol-5-yl)-meth-(E or Z)-ylidene]-3-ethyl-4-oxo-thiazolidin-(5-(E/Z))-ylidenemethyl]-amino}-phenyl)-2,2-dimethyl-propionamide

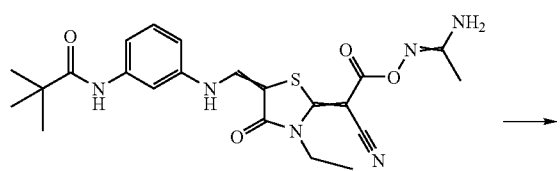

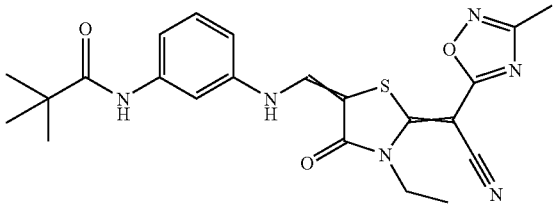

205 mg of the compound that is described under Intermediate Compound INTB2) is dissolved in 16 ml of tetrahydrofuran, mixed with 270 mg of Burgess' reagent and stirred for one hour under reflux. The reaction mixture is mixed with semi-saturated sodium bicarbonate solution and extracted with dichloromethane. The organic phase is dried on sodium sulfate, concentrated by evaporation, and after purification by chromatography on silica gel, 27 mg of the title compound is obtained.

1H-NMR (DMSO-d6, stored with $K_2CO_3$, main isomer): δ=1.24 (s, 9H); 1.31 (t, 3H); 2.40 (s, 3H); 4.32 (q, 2H); 7.00 (d, 1H); 7.28 (t, 1H); 7.39 (d, 1H); 7.79 (s, 1H); 8.20 (s, 1H); 9.28 (s, 1H); 10.83 (s, b, 1H) ppm.

The following compounds of general formula (I) can be produced analogously.

TABLE 7

Compounds of General Formula (I)

| Example No. | Structure and Name | 1H-NMR | Molecular Weight/ MS (ESI) [M + 1]+ | Educt/ Synthesis Analogously to |
|---|---|---|---|---|
| 43 | [3-Ethyl-4-oxo-5-[1-phenylamino-meth-(E/Z)-ylidene]-thiazolidin-(2-(E or Z))-ylidene]-(3-methyl-[1,2,4]oxadiazol-5-yl)-acetonitrile | (DMSO-d6, stored with $K_2CO_3$, main isomer): δ = 1.31(t, 3H); 2.40(s, 3H); 4.31(q, 2H); 7.07-7.18(m, 1H); 7.30-7.44(m, 4H); 8.26(d, 1H); 10.62(d, 1H)ppm. | MW: 353.41 MS (ESI) [M + 1]+: 354 | INTB41/42 |
| 44 | N-(3-{[2-[1-Cyano-1-(3-methyl-[1,2,4]oxadiazol-5-yl)-meth-(E or Z)-ylidene]-3-ethyl-4-oxo-thiazolidin-(5-(E/Z))-ylidenemethyl]-amino}-phenyl)-2-(2-methoxy-ethoxy)-acetamide | (DMSO-d6, stored with $K_2CO_3$, main isomer): δ = 1.30(t, 3H); 2.40(s, 3H); 3.32(s, 3H); 3.55(t, 2H); 3.68(t, 2H); 4.10(s, 2H); 4.31(q, 2H); 7.02-7.11(m, 1H); 7.27-7.37(m,2H); 7.83(s, 1H); 8.21(s, 1H); 9.77(s, 1H); 10.86(s, 1H)ppm. | MW: 484.54 MS (ESI) [M + 1]+: 485 | INTB42/42 |

Example 45

[3-Ethyl-4-oxo-5-[1-phenylamino-meth-(E/Z)-ylidene]-thiazolidin-(2-(E or Z))-ylidene]-pyridin-2-yl-acetonitrile

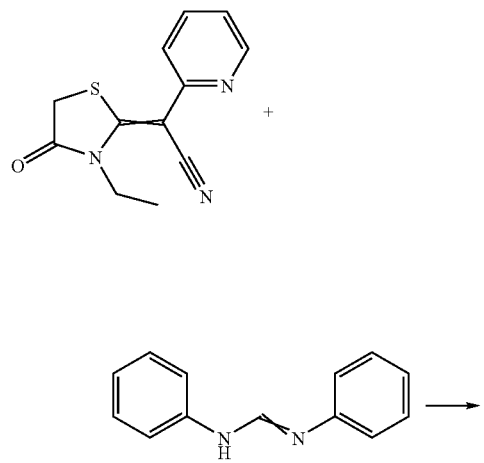

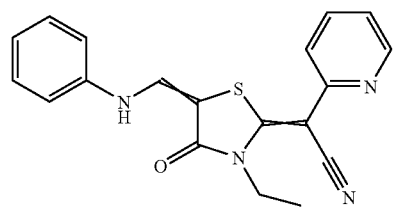

0.72 g (2.94 mmol) of the compound that is produced under INTT6) and 0.63 g (3.21 mmol) of N,N'-diphenylformamidine are heated together for 20 minutes at 140° C. After cooling, about 0.40 g of the crude product is dissolved in 7 ml of dimethyl sulfoxide (with 0.1% added TFA). The solution that is obtained is purified by reverse-phase chromatography (acetonitrile/water, 0.1% TFA). After freeze-drying, 0.28 g of the title compound is obtained.

$^1$H NMR (DMSO-d6, main isomer): δ=1.31 (t, 3H); 4.36 (q, 2H); 7.05 (t, 1 H); 7.22 (dd, 2H); 7.27-7.37 (m, 3H); 7.62 (d, 1H); 7.89 (t, 1H); 8.05 (d, 1H); 8.62 (d, 1H); 10.19 (d, 1H) ppm.

MW: 348.43; MS (ES+) found:[M+1]$^+$: 349.

The following compounds of general formula (I) are produced analogously to the above-described process.

TABLE 8

| | Compounds of General Formula (I) | | | |
|---|---|---|---|---|
| Example No. | Structure and Name | $^1$H-NMR | Molecular Weight/ MS (ESI) [M + 1]$^+$ | Educt/ Synthesis Analogously to |
| 46 | [3-Ethyl-4-oxo-5-[1-phenylamino-meth-(E/Z)-ylidene]-thiazolidin-(2-(E or Z))-ylidene]-pyridin-3-yl-acetonitrile | (DMSO-d6, Main Isomer): δ = 1.33(t, 3H); 4.21(q, 2H); 7.00(t, 1H); 7.17(d, 2H); 7.29(t, 2H); 7.59(dd, 1H); 7.99-8.04(m, 2H); 8.64(d, 1H); 8.75(d, 1H); 9.77(d, 1H)ppm. | MW: 348.43 MS (ES+) [M + 1]+: 349 | INTT7/45 |
| 47 | [3-Ethyl-4-oxo-5-[1-phenylamino-meth-(E/Z)-ylidene]-thiazolidin-(2-(E or Z))-ylidene]-pyridin-4-yl-acetonitrile | (DMSO-d6, Main Isomer): δ = 1.29(t, 3H); 4.19(q, 2H); 7.05(t, 1H); 7.24(d, 2H); 7.33(t, 2H); 7.73(dd, 2H); 8.13(d, 1H); 8.72(dd, 2H); 10.08(d, 1H)ppm. | MW: 348.43 MS (ES+) [M + 1 +: 349 | INTT8/45 |

TABLE 8-continued

Compounds of General Formula (I)

| Example No. | Structure and Name | ¹H-NMR | Molecular Weight/ MS (ESI) [M + 1]⁺ | Educt/ Synthesis Analogously to |
|---|---|---|---|---|
| 48 | 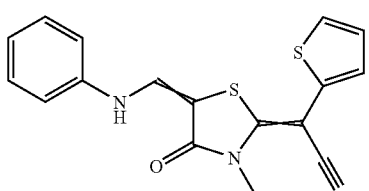<br>3-Ethyl-4-oxo-5-[1-phenylamino-meth-(E/Z)-ylidene]-thiazolidin-(2-(E or Z))-ylidene]-thiophen-2-yl-acetonitrile | (DMSO-d6, Main Isomer): δ = 1.29(t, 3H); 4.19(q, 2H); 7.01(t, 1H); 7.16(dd, 1H); 7.20(d, 2H); 7.27-7.32(m, 3H); 7.71(dd, 1H); 8.03(d, 1H); 9.85(d, 1H)ppm. | MW: 353.47 MS (ES+) [M + 1]+: 354 | INTT9/45 |
| 49 | 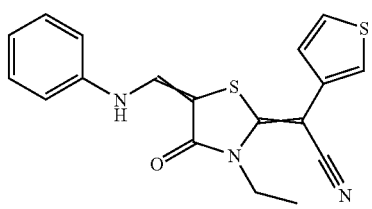<br>[3-Ethyl-4-oxo-5-[1-phenylamino-meth-(E/Z)-ylidene]-thiazolidin-(2-(E or Z))-ylidene]-thiophen-3-yl-acetonitrile | (DMSO-d6, Main Isomer): δ = 1.29(t, 3H); 4.19(q, 2H); 7.00(t, 1H); 7.18(d, 2H); 7.25(d, 1H); 7.29(t, 2H); 7.68-7.72(m, 1H); 7.76(m, 1H); 7.99(d, 1H); 9.76(d, 1H)ppm. | MW: 353.47 MS (ES+) [M + 1]+: 354 | INTT10/45 |
| 50 | 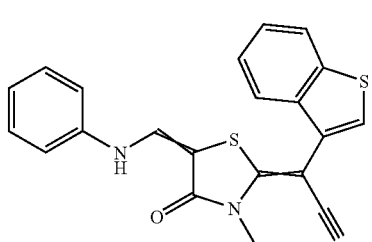<br>Benzo[b]thiophen-3-yl-[3-ethyl-4-oxo-5-[1-phenylamino-meth-(E/Z)-ylidene]-thiazolidin-(2-(E or Z))-ylidene]-acetonitrile | (DMSO-d6, Main Isomer): δ = 1.39(t, 3H); 4.27(q, 2H); 6.97(t, 1H); 7.12(d, 2H); 7.26(t, 2H); 7.44-7.51(m, 2H); 7.81(dd, 1H); 7.98(d, 1H); 8.09(dd, 1H); 8.11(s, 1H); 9.63(d, 1H)ppm. | MW: 403.53 MS (ES+) [M + 1]+: 405 | INTT11/45 |
| 51 | 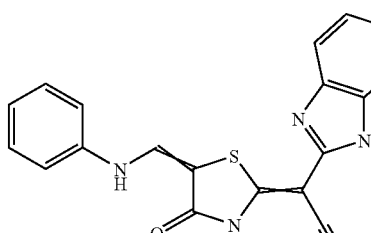<br>[3-Ethyl-4-oxo-5-[1-phenylamino-meth-(E/Z)-ylidene]-thiazolidin-(2-(E or Z))-ylidene]-(1-methyl-1H-benzoimidazol-2-yl)-acetonitrile | (DMSO-d6, Main Isomer): δ = 1.36(br t, 3H); 3.88(s, 3H); 4.29(br q, 2H);) 7.03(t, 1H); 7.21(d, 2H); 7.27-7.37(m, 4H); 7.63(d, 1H); 7.68(d, 1H); 8.10(d, 1H); 10.01(d, 1H)ppm. | MW: 401.49 MS (ES+) [M + 1]+: 402 | INTT12/45 |

TABLE 8-continued

Compounds of General Formula (I)

| Example No. | Structure and Name | $^1$H-NMR | Molecular Weight/ MS (ESI) [M + 1]$^+$ | Educt/ Synthesis Analogously to |
|---|---|---|---|---|
| 52 | Benzothiazol-2-yl-[3-ethyl-4-oxo-5-[1-phenylamino-meth-(E/Z)-ylidene]-thiazolidin-(2-(E or Z))-ylidene]-acetonitrile | (DMSO-d6, Main Isomer): δ = 1.33(t, 3H); 4.33(q, 2H); 7.11(t, 1H); 7.33-7.42(m, 5H); 7.54(t, 1H); 7.92(d, 1H); 8.08(d, 1H); 8.22(d, 1H); 10.56(d, 1H)ppm. | MW: 404.52 MS (ES+) [M + 1]: 405 | INTT13/45 |
| 53 | [3-Ethyl-4-oxo-5-[1-phenylamino-meth-(E/Z)-ylidene]-thiazolidin-(2-(E or Z))-ylidene]-(4-methyl-thiazol-2-yl)-acetonitrile | (DMSO-d6, Main Isomer): δ = 1.28(t, 3H); 2.44(s, 3H); 4.27(q, 2H); 7.08(t, 1H); 7.19(s, 1H); 7.29-7.39(m, 4H); 8.12(d, 1H); 10.33(d, 1H)ppm. | MW: 368.48 MS (ES+) [M + 1]+: 369 | INTT14/45 |
| 54 | [3-Ethyl-4-oxo-5-[1-phenylamino-meth-(E/Z)-ylidene]-thiazolidin-(2-(E or Z))-ylidene]-(1-methyl-1H-pyrrol-2-yl)-acetonitrile | (DMSO-d6, Main Isomer): δ = 1.30(t, 3H); 3.55(s, 3H); 4.19(q, 2H); 6.09(t, 1H); 6.20(q, 1H); 6.92(t, 1H); 6.99(t, 1H); 7.17(d, 2H); 7.29(t, 2H); 7.98(d, 1H); 9.75(d, 1H)ppm. | MW: 350.45 MS (ES+) [M + 1]: 351 | INTT15/45 |

EXAMPLES

The following examples describe the biological action of the compounds according to the invention:

PLK Enzyme Assay

Recombinant human Plk-1 (6× His) was purified from baculovirus-infected insect cells (Hi5).

10 ng of (produced in a recombinant manner and purified) PLK enzyme is incubated for 90 minutes at room temperature with biotinylated casein and 33P-γ-ATP as a substrate in a volume of 15 μl in 384-well Greiner small-volume microtiter plates (final concentrations in the buffer: 660 ng/ml of PLK; 0.7 lmol of casein, 0.5 gmol of ATP incl. 400 nCi/ml of 33P-γ-ATP; 10 mmol of MgCl2, 1 mmol of MnCl2; 0.01% NP40; 1 mmol of DTT, protease inhibitors; 0.1 mmol of Na2VO3 in 50 mmol of HEPES, pH 7.5). To complete the reaction, 5 μl of stop solution (500 μmol of ATP; 500 mmol of EDTA; 1% Triton X100; 100 mg/ml of streptavidin-coated SPA beads in PBS) is added. After the microtiter plate is sealed by film, the beads are sedimented by centrifuging (10 minutes, 1500 rpm). The incorporation of 33P-γ-ATP in casein is intended as a measurement of enzyme activity by β-counting. The extent of the inhibitor activity is referenced against a solvent control (=uninhibited enzyme activity=0% inhibition) and the mean value of several batches that contained 300 μmol of wortmannin (=completely inhibited enzyme activity=100% inhibition).

Test substances are used in various concentrations (0 μmol, as well as in the range of 0.01-30 μmol). The final concentration of the solvent dimethyl sulfoxide is 1.5% in all batches.

Proliferation Assay

Cultivated human MaTu breast tumor cells were flattened out at a density of 5000 cells/measuring point in a 96-well multititer plate in 200 μl of the corresponding growth medium. After 24 hours, the cells of one plate (zero-point plate) were colored with crystal violet (see below), while the medium of the other plates was replaced by fresh culture medium (200 μl), to which the test substances were added at various concentrations (0 μm, as well as in the range of 0.01-30 μm; the final concentration of the solvent dimethyl sulfoxide was 0.5%). The cells were incubated for 4 days in the presence of test substances. The cell proliferation was determined by coloring the cells with crystal violet: the cells were fixed by adding 20 μl/measuring point of an 11% glutaric aldehyde solution for 15 minutes at room temperature. After three washing cycles of the fixed cells with water, the plates were dried at room temperature. The cells were colored by adding 100 μl/measuring point of a 0.1% crystal violet solution (pH was set at 3 by adding acetic acid). After three washing cycles of the colored cells with water, the plates were dried at room temperature. The dye was dissolved by adding 100 μl/measuring point of a 10% acetic acid solution. The extinction was determined by photometry at a wavelength of 595 nm. The change of cell growth, in percent, was calculated by standardization of the measured values to the extinction values of the zero-point plate (=0%) and the extinction of the untreated (0 μm) cells (=100%).

TABLE 9

Assay Data

| Example No. | Structure | PLK-1 IC50 [nM] Inhibition | Inhibition of the Tumor Cell Proliferation (MaTu) IC50 [μM] |
|---|---|---|---|
| 15 | 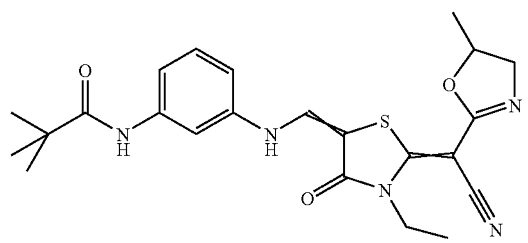 | 55 | 2.1 |
| 20 | 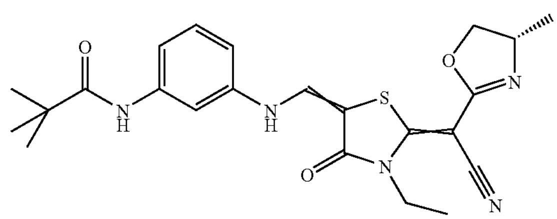 | 140 | 3.2 |
| 31 | 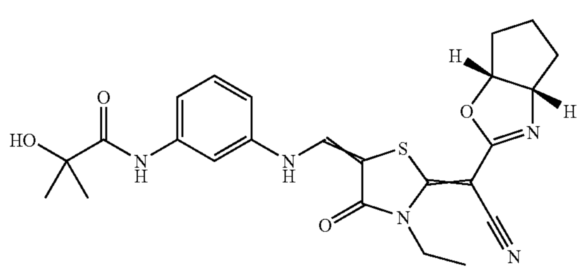 | 53 | 1.2 |
| 37 | 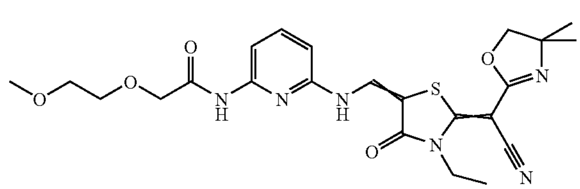 | 69 | 3.6 |

TABLE 9-continued

Assay Data

| Example No. | Structure | PLK-1 IC50 [nM] Inhibition | Inhibition of the Tumor Cell Proliferation (MaTu) IC50 [µM] |
|---|---|---|---|
| 38 | 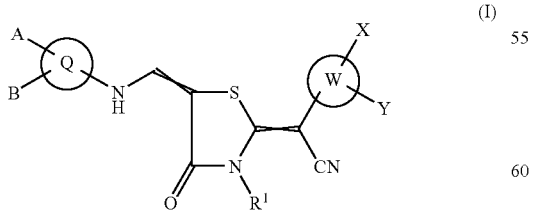 | 24 | 1.2 |

From Table 1, it thus can be seen that the compounds of general formula (I) have an inhibitory action both on the enzyme and in the proliferation test.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102005005395.5, filed Feb. 3, 2005 and U.S. Provisional Application Ser. No. 60/651,232, filed Feb. 3, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:
1. A compound of formula I

(I)

in which
Q stands for aryl or heteroaryl,
A and B, independently of one another, stand for hydrogen, halogen, hydroxy, amino or nitro, or for $C_1$-$C_6$-alkyl or $C_1$-$C_6$-alkoxy that optionally is substituted in one or more places, in the same way or differently, with halogen, hydroxy, $C_2$-$C_9$-heterocycloalkyl or with the group —$NR^3R^4$ or —CO($NR^3$)-M, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the ring is optionally substituted in one or more places, in the same way or differently, with cyano, halogen, or with $C_1$-$C_6$-alkyl, $C_3$-$C_6$-cycloalkyl, or $C_1$-$C_6$-hydroxyalkyl that is substituted in one or more places, in the same way or differently, with halogen, or with the group —$COR^2$ or —$NR^3R^4$, or for —$NR^3R^4$, —$NR^3$(CO)-L, —$NR^3$(CO)—$NR^3$-L, —$COR^2$, —CO($NR^3$)-M, —$NR^3$(CS)$NR^3R^4$, —$NR^3SO_2$-L, —$SO_2$—$NR^3R^4$ or —$SO_2$($NR^3$)-M, L stands for $C_1$-$C_6$-alkyl or heteroaryl that optionally is substituted in one or more places, in the same way or differently, with hydroxy, $C_1$-$C_6$-hydroxyalkoxy, $C_1$-$C_6$-alkoxyalkoxy, $C_2$-$C_6$-heterocycloalkyl or with the group -$NR^3R^4$, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the ring is optionally substituted in one or more places, in the same way or differently, with cyano, halogen, or with $C_1$-$C_6$-alkyl, $C_3$-$C_6$-cycloalkyl, or $C_1$-$C_6$-hydroxyalkyl that is substituted in one or more places, in the same way or differently, with halogen, or with the group —$COR^2$ or —$NR^3R^4$, M stands for $C_1$-$C_6$-alkyl that optionally is substituted in one or more places, in the same way or differently, with the group —$NR^3R^4$ or $C_2$-$C_6$-heterocycloalkyl, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the ring is optionally substituted in one or more places, in the same way or differently, with cyano, halogen or with $C_1$-$C_6$-alkyl, $C_3$-$C_6$-cycloalkyl, or $C_1$-$C_6$-hydroxyalkyl that is substituted in one or more places, in the same way or differently, with halogen, or with the group —$COR^2$ or —$NR^3R^4$, W stands for heteroaryl or $C_2$-$C_9$-heterocycloalkyl, wherein the heterocycloalkyl in the ring contains at least one nitrogen, oxygen or sulfur atom, which is the same or different, and optionally is interrupted by one or more —(CO)— or —$SO_2$— groups in the ring, and optionally one or more double bonds are contained in the ring, X and Y, independently of one another, stand for hydrogen or $C_1$-$C_6$-alkyl or aryl that optionally is substituted in one or more places, in the same way or differently, with halogen, hydroxy, $C_1$-$C_6$-alkoxy, $C_1$-$C_6$-alkylthio or aryl, or for the group —$COOR^5$ or —$CONR^3R^4$, or X and Y together with the same atom or adjacent atoms of W form a $C_3$-$C_6$-cycloalkyl ring or a $C_2$-$C_6$-heterocycloalkyl ring, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the ring is optionally substituted in one or more places, in the same way or differently, with $C_1$-$C_6$-alkyl, $C_3$-$C_6$-cycloalkyl, $C_1$-$C_6$-hydroxyalkyl or with the group —$NR^3R^4$, $R^1$ stands for $C_1$-$C_4$-alkyl, $C_3$-cycloalkyl, allyl or propargyl that optionally is substituted in one or more places, in the same way or differently, with cyano or halogen, $R^2$ stands for hydroxy, $C_1$-$C_6$-alkyl, $C_1$-$C_6$-alkoxy or for the group —$NR^3R^4$, $R^3$ and $R^4$, independently of one another, stand for hydrogen or for $C_1$-$C_6$-alkyl, $C_1$-$C_6$-alkoxy, —CO-$C_1$-$C_6$-alkyl or aryl that optionally is substituted in one or more places, in the same way or differently, with halogen, hydroxy, $C_2$-$C_6$-heterocycloalkyl, $C_1$-$C_6$-hydroxyalkoxy or with the group —$NR^3R^4$, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and wherein the $C_2$-$C_6$-heterocycloalkyl ring in each case optionally is substituted in one or more places, in the same way or differently, with cyano, halogen, $C_1$-$C_6$-alkyl, $C_1$-$C_6$-hydroxyalkyl, $C_1$-$C_6$-alkoxy, $C_3$-$C_6$-cycloalkyl, or with the group —$NR^3R^4$ or —CO—$NR^3R^4$, or $R^3$ and $R^4$ together form a $C_2$-$C_6$-heterocycloalkyl ring, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the heterocycloalkyl ring is optionally substituted in one or more places, in the same way or differently, with halogen, $C_1$-$C_6$-alkyl, $C_3$-$C_6$-cycloalkyl, $C_1$-$C_6$-hydroxyalkyl, $C_1$-$C_6$-alkoxyalkyl, cyano, hydroxy or with the group —$NR^3R^4$, and $R^5$ stands for $C_1$-$C_6$-alkyl that optionally is substituted in one or more places, in the same way or differently, with halogen, hydroxy, $C_2$-$C_6$-heterocycloalkyl, $C_1$-$C_6$-hydroxyalkoxy or with the group —$NR^3R^4$, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the heterocycloalkyl ring is optionally substituted in one or more places, in the same way or differently, with $C_1$-$C_6$-alkyl, $C_3$-$C_6$-cycloalkyl, $C_1$-$C_6$-hydroxyalkyl, $C_1$-$C_6$-alkoxyalkyl, cyano, hydroxy or with the group —$NR^3R^4$, or a stereoisomer, diastereomer, enantiomer, or salt thereof.

2. A compound according to claim 1, in which

Q stands for phenyl, pyridyl, naphthyl, quinolinyl, benzimidazolyl, indolyl, indazolyl, thiazolyl, imidazolyl or pyrimidinyl.

3. A compound according to claim 1, in which

Q stands for phenyl, pyridyl, naphthyl, indolyl or pyrimidinyl,

M stands for $C_1$-$C_6$-alkyl that optionally is substituted in one or more places, in the same way or differently, with $C_2$-$C_6$-heterocycloalkyl, wherein the heterocycloalkyl in the ring contains at least one nitrogen, oxygen or sulfur atom, which is the same or different, $R^3$ and $R^4$, independently of one another, stand for hydrogen or for $C_1$-$C_6$-alkyl, $C_1$-$C_6$-alkoxy or CO—$C_1$-$C_6$-alkyl that optionally is substituted in one or more places, in the same way or differently, with halogen, hydroxy, or $C_1$-$C_6$-hydroxyalkoxy, and $R^5$ stands for $C_1$-$C_6$-alkyl that optionally is substituted in one or more places, in the same way or differently, with halogen, hydroxy, C2326-heterocycloalkyl, $C_1$-$C_6$-hydroxyalkoxy or with the group —$NR^3R^4$, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring.

4. A compound according to claim 1, in which

Q stands for phenyl or pyridyl,

W stands for oxazole, 4,5-dihydrooxazole, oxadiazole, triazole, thiazole, pyridine, thiophene, benzo thiophene, benzoimidazole, benzothiazole or pyrrole, X and Y, independently of one another, stand for hydrogen or for $C_1$-$C_6$-alkyl or aryl that optionally is substituted in one or more places, in the same way or differently, with halogen, hydroxy, $C_1$-$C_6$-alkoxy, $C_1$-$C_6$-alkylthio or aryl, or for the group —$COOR^5$ or —$CONR^3R^4$, or X and Y together with the same atom or adjacent atoms or W form a cyclopropyl ring, a cyclobutyl ring, a cyclopentyl ring or a cyclohexyl ring, $R^1$ stands for $C_1$-$C_4$-alkyl that optionally is substituted in one or more places, in the same way or differently, with halogen, and $R^5$ stands for $C_1$-$C_6$-alkyl that optionally is substituted in one or more places, in the same way or differently, with halogen, hydroxy, or $C_1$-$C_6$-hydroxyalkoxy.

5. A compound according to claim 1, in which

A and B, independently of one another, stand for hydrogen or halogen or for $C_1$-$C_3$-alkyl or $C_1$-$C_6$alkoxy that optionally is substituted in one or more places, in the same way or differently, with pyrrolidinyl, piperidinyl, piperazinyl, morpholinyl, thiomorpholinyl, tetrahydroisoquinolinyl or decahydroisoquinolinyl, wherein the pyrrolidinyl, piperidinyl, piperazinyl, morpholinyl, thiomorphol inyl, tetrahydroisoquinol inyl or decahydroisoquinolinyl is optionally substituted in one or more places, in the same way or differently, with halogen or with $C_1$-$C_6$-alkyl that optionally is substituted in one or more places, in the same way or differently, with halogen, or with the group —$COR^2$, or for —$NR^3R^4$, —$NR^3$(CO)-L or —CO($NR^3$-M, L stands for $C_1$-$C_6$-alkyl that optionally is substituted in one or more places, in the same way or differently, with hydroxy, $C_1$-$C_6$-alkoxyalkoxy, pyrrolidinyl, piperidinyl, piperazinyl, morpholinyl, thiomorpholinyl or decahydroisoquinolinyl, wherein the pyrrolidinyl, piperidinyl, piperazinyl, morpholinyl, thiomorpholinyl or decahydroisoquinolinyl is optionally substituted in one or more places, in the same way or differently, with halogen or with $C_1$-$C_6$-alkyl that optionally is substituted in one or more places, in the same way or differently, with halogen, or with the group —$COR^2$, M stands for $C_1$-$C_6$-alkyl that optionally is substituted in one or more places, in the same way or differently, with pyrrolidinyl, X and Y, independently of one another, stand for hydrogen, or for $C_1$-$C_6$-alkyl or phenyl that optionally is substituted in one or more places, in the same way or differently, with halogen, $C_1$-$C_6$-alkoxy, $C_1$-$C_6$-alkylthio or phenyl, or for the group —$COOR^5$ or —$CONR^3R^4$, or X and Y together with the same atom or adjacent atoms of W form a cyclopentyl ring or a cyclohexyl ring, $R^2$ stands for $C_1$-$C_6$-alkyl, $R^3$ and $R^4$, independently of one another, stand for hydrogen or $C_1$-$C_6$-alkyl, and $R^5$ stands for $C_1$-$C_6$-alkyl.

6. A compound according to claim 1, in which

A and B, independently of one another, stand for hydrogen or halogen, or for $C_1$-$C_3$-alkyl that optionally is substituted in one or more places, in the same way or differently, with pyrrolidinyl, piperidinyl, piperazinyl, morpholinyl, thiomorpholinyl, tetrahydroisoquinolinyl or decahydroisoquinolinyl, or for —$NR^3R^4$, —$NR^3(CO)$-L or —$CO(NR^3)$-M, L stands for $C_1$-$C_6$-alkyl that optionally is substituted in one or more places, in the same way or differently, with hydroxy, or $C_1$-$C_6$-alkoxyalkoxy, M stands for $C_1$-$C_6$-alkyl that is substituted with pyrrolidinyl, and $R^1$ stands for $C_1$-$C_4$-alkyl.

7. A compound according to claim 1, in which

A and B independently of one another, stand for hydrogen or halogen, or for $C_1$-$C_3$-alkyl that optionally is substituted in one or more places, in the same way or differently, with pyrrolidinyl or decahydroisoquinolinyl, or for —$NR^3R^4$, —$NR^3(CO)$-L or —$CO(NR^3)$-M, L stands for isopropyl, tert-butyl or methyl that optionally is substituted in one or more places, in the same way or differently, with hydroxy or $C_1$-$C_6$-alkoxyalkoxy, M stands for $C_1$-$C_3$-alkyl that is substituted with pyrrolidinyl, X and Y, independently of one another, stand for hydrogen, or for methyl, ethyl, isopropyl, propyl, isobutyl, tert-butyl or phenyl that optionally is substituted in one or more places, in the same way or differently, with halogen, $C_1$-$C_6$-alkoxy, $C_1$-$C_6$-alkylthio or phenyl, or for the group —$COOR^5$ or —$CONR^3R^4$, or X and Y together with the same atom or adjacent atoms of W form a cyclopentyl ring or a cyclohexyl ring, $R^1$ stands for ethyl, $R^2$ and $R^2$, independently of one another, stand for hydrogen or $C_1$-$C_3$-alkyl, and $R^5$ stands for methyl.

8. A pharmaceutical composition comprising a compound according to claim 1 and a pharmaceutical acceptable carrier.

9. A compound of claim 1, which is in the form of a salt.

10. A compound of formula I

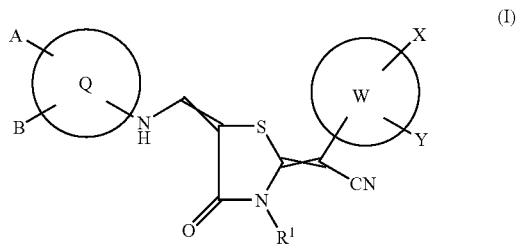

in which

Q stands for aryl or heteroaryl,

A and B, independently of one another, stand for hydrogen, halogen, hydroxy, amino or nitro, or for $C_1$-$C_6$-alkyl or $C_1$-$C_6$-alkoxy that optionally is substituted in one or more places, in the same way or differently, with halogen, hydroxy, $C_2$-$C_9$-heterocycloalkyl or with the group —$NR^3R^4$ or —$CO(NR^3)$-M, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the ring is optionally substituted in one or more places, in the same way or differently, with cyano, halogen, or with $C_1$-$C_6$-alkyl, $C_3$-$C_6$-cycloalkyl, or $C_1$-$C_6$-hydroxyalkyl that is substituted in one or more places, in the same way or differently, with halogen, or with the group —$COR^2$ or —$NR^3R^4$ or for —$NR^3R^4$, —$NR^3(CO)$-L, —$NR^3(CO)$—$NR^3$-L, —$COR^2$, —$CO(NR^3)$-M, —$NR^3(CS)NR^3R^4$, —$NR^3SO_2$-L, —$SO_2$—$NR^3R^4$ or —$SO_2(NR^3)$-M, L stands for $C_1$-$C_6$-alkyl or heteroaryl that optionally is substituted in one or more places, in the same way or differently, with hydroxy, $C_1$-$C_6$-hydroxyalkoxy, $C_1$-$C_6$-alkoxyalkoxy, $C_2$-$C_6$-heterocycloalkyl or with the group -$NR^3R^4$, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the ring is optionally substituted in one or more places, in the same way or differently, with cyano, halogen, or with $C_1$-$C_6$-alkyl, $C_3$-$C_6$-cycloalkyl, or $C_1$-$C_6$-hydroxyalkyl that is substituted in one or more places, in the same way or differently, with halogen, or with the group —$COR^2$ or —$NR^3R^4$, M stands for $C_1$-$C_6$-alkyl that optionally is substituted in one or more places, in the same way or differently, with the group —$NR^3R^4$ or $C_2$-$C_6$-heterocycloalkyl, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the ring is optionally substituted in one or more places, in the same way or differently, with cyano, halogen or with $C_1$-$C_6$-alkyl, $C_3$-$C_6$-cycloalkyl, or $C_1$-$C_6$-hydroxyalkyl that is substituted in one or more places, in the same way or differently, with halogen, or with the group —$COR^2$ or —$NR^3R^4$, W stands for heteroaryl or $C_2$-$C_9$-heterocycloalkyl, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, X and Y, independently of one another, stand for hydrogen or $C_1$-$C_6$-alkyl or aryl that optionally is substituted in one or more places, in the same way or differently, with halogen, hydroxy, $C_1$-$C_6$-alkoxy, $C_1$-$C_6$-alkylthio or aryl, or for the group —$COOR^5$ or —$CONR^3R^4$, or X and Y together with the same atom or adjacent atoms of W form a $C_3$-$C_6$-cycloalkyl ring or a $C_2$-$C_6$-heterocycloalkyl ring, wherein the heterocycloalkyl in the ring contains at least one nitrogen, oxygen or sulfur atom, which is the same or different, and is optionally interrupted by one or more —(CO)— or $SO_2$— groups in the ring, and optionally one or more double bonds are contained in the ring, and the ring is optionally substituted in one or more places, in the same way or differently, with $C_1$-$C_6$-alkyl, $C_3$-$C_6$-cycloalkyl, $C_1$-$C_6$-hydroxyalkyl or with the group —$NR^3R^4$, $R^1$ stands for $C_1$-$C_4$-alkyl, $C_3$-cycloalkyl, allyl or propargyl that optionally is substituted in one or more places, in the same way or differently, with cyano or halogen, $R^2$ stands for hydroxy, $C_1$-$C_6$-alkyl, $C_1$-$C_6$-alkoxy or for the group —$NR^3R^4$, $R^3$ and $R^4$, independently of one another, stand for hydrogen or for $C_1$-$C_6$-alkyl, $C_1$-$C_6$-alkoxy, —CO—$C_1$-$C_6$-alkyl or aryl that optionally is substituted in one or more places, in the same way or differently, with halogen, hydroxy, $C_2$-$C_6$-heterocycloalkyl, $C_1$-$C_6$-hydroxyalkoxy or with the group —$NR^3R^4$, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and wherein the $C_2$-$C_6$-heterocycloalkyl ring in each case optionally is substituted in one or more places, in the same way or differently, with cyano, halogen, $C_1$-$C_1$-alkyl, $C_1$-$C_6$-hydroxyalkyl, $C_1$-$C_6$-alkoxy, $C_3$-$C_6$-cycloalkyl, or with the group —$NR^3R^4$ or —CO—$NR^3R^4$, or $R^3$ and $R^4$ together form a $C_2$-$C_6$-heterocycloalkyl ring, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the heterocycloalkyl ring is optionally substituted in one or more places, in the same way or differently, with halogen, $C_1$-$C_6$-alkyl, $C_3$-$C_6$-cycloalkyl, $C_1$-$C_6$hydroxyalkyl, $C_1$-$C_6$-alkoxyalkyl, cyano, hydroxy or with the group —$NR^3R^4$, and $R^5$ stands for $C_1$-$C_6$-alkyl that optionally is substituted in one or more places, in the same way or differently, with halogen, hydroxy, $C_3$-$C_6$-heterocycloalkyl, $C_1$-$C_6$-hydroxyaikoxy or with the group —$NR^3R^4$, wherein the heterocycloalkyl in the ring contains at least one nitrogen, oxygen or sulfur atom, which is the same or different, and is optionally interrupted by one or more —(CO)— or —$SO_2$— groups in the ring, and optionally one or more double bonds are contained in the ring, and the heterocycloalkyl ring is optionally substituted in one or more places, in the same way or differently, with $C_1$-$C_6$-alkyl, $C_3$-$C_6$-cycloalkyl, $C_1$-$C_6$-hydroxyalkyl, $C_1$-$C_6$-alkoxyalkyl, cyano, hydroxy or with the group —$NR^3R^4$.

11. A compound according to claim 1, which is (4,4-Dimethyl-4,5-dihydro-oxazol-2-yl)-[3-ethyl-4-oxo-5-[1-[3-(2-pyrrolidin-1-yl-ethyl)-phenylamino]-meth-(E/Z)-ylidene]-thiazolidin-(2-(E or Z))-ylidene]-acetonitrile;

(4,4-Dimethyl-4,5-dihydro-oxazol-2-yl)-[3-ethyl-4-oxo-5-[1[4-(2-pyrrolidin-1-yl-ethyl)-phenylamino]-meth-(E/Z)-ylidene]-thiazolidin-(2-(E or Z))-ylidene]-acetonitrile;

[3-Ethyl-4-oxo-5-[1-[4-(2-pyrrolidin-1-yl-ethyl)-phenylamino]-meth-(E/Z)-ylidene]-thiazolidin-(2-(E or Z))-ylidene]-((S)-4-methyl-4,5-dihydro-oxazol-2-yl)-acetonitrile;

((S)-4-Ethyl-4,5-dihydro-oxazol-2-yl)-[3-ethyl-4-oxo-5-[1-[4-(2-pyrrolidin-1-yl-ethyl)-phenylarmino]-meth-(E/Z)-ylidenel]-thiazolidin-(2-(E or Z))-ylidene]-acetonitrile;

[3-Ethyl-4-oxo-5-[1-[4-(2-pyrrolidin-1-yl-ethyl)-phenylamino]-meth-(E/Z)-ylidene]-thiazolidin-(2-(E or Z))-ylidene]-((S)-4-isopropyl-4,5-dihydro-oxazol-2-yl)-acetonitrile;

3-{[2-[1-Cyano-1-(4,5-dihydro-oxazo-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide;

3-{[2-[-Cyano-1-(3-oxa-1-aza-spiro[4.4]non-1-en-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide;

3-{[2-[1-Cyano-1-((S)-4-methyl-4,5-dihydro-oxazol-2-yl)-meth-(E or Z)-ylidene]-3-ethyl-4-oxo-thiazolidin-(5-(E/Z))-ylidenemethyl]-amino}-N-(3-pyrrolidin-1-yl-propyl)-benzamide;

3-{[2-[1-Cyano-1-(4,4-dimethyl -4,5-dihydro-oxazo 1-2-yl)-meth-(E or Z)-ylidene]-3-ethyl -4-oxo -thiazolidin-(5-(E/Z))-ylidenemethyl]-amino}-N-(3-pyrrolidin-1-yl-propyl)-benzmnide;

3-{[2-[1-Cyano-1-((S)-4-ethyl-4,5-dihydro-oxazol-2-yl)-meth-(E or Z)-ylidene]-3-ethyl-4-oxo -thiazolidin-(5-(E/Z))-ylidenemethyl]-amino}-N-(3-pyrrolidin-1-yl-propyl)-benzamide;

3-{[2-[1-Cyano-1-((R)-4-ethyl-4,5-dihydro-oxazol-2-yl)-meth-(E or Z)-ylidene]-3-ethyl-4-oxo -thiazolidin-(5-(E/Z))-ylidenemethyl]-amimo}-N-(3-pyrrolidin-1-yl-propyl)-benzamide;

3-{[2-[1-((S)-4-Benzyl-4,5-dihydro-oxazol-2-yl)-1-cyano-meth-(E or Z)-ylidene]-3-ethyl-4-oxo -thiazolidin-(5-(E/Z))-ylidenemethyl]-amino}-N-(3-pyrrolidin-1-yl-propyl)-benzamide;

N-(3-{[2-]1-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionainide;

N-(3-{[2-[(3aS,6aR)-1-Cyano-1-4,5,6,6a-tetrahydro-3aH-cycopentaoxazol]-2-yl-meth-(E or Z)-ylidene]-3-ethyl-4-oxo-thiazolidin-(5-(E/Z))-ylidenemethyl]-amino}-phenyl)-2,2-dimethyl -propionamide;

N-(3-{[2-[1-Cyano-1-(5-methyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide;

N-(3-{[2-[1-Cyano-1-((S)-4-ethyl-4,5-dihydro-oxazo-2-yl)-meth-(E or Z)-ylidene]-3-ethyl-4-oxo-thiazolidin-(5-(E/Z))-ylidenemethyl]-amino}-phenyl)-2,2-dimethyl-propionamide;

N-(3-{[2[1-Cyano-1-(4-propyl-4,5-dihydro-oxazol-2-yl)-meth-(E or Z)-ylidene ]-3-ethyl-4-oxo -thiazolidin-(5-(E/Z))-ylidenemethyl]-amino}-phenyl)-2,2-dimethyl-propionamide;

N-(3-{[2-[(3aS ,7aR)-1-Cyano-1-3a,4, 5, 6, 7, 7a-hexahydro-benzooxazol-2-yl-meth-(E or Z)-ylidene]-3-ethyl-4-oxo-thiazolidin-(5-(E/Z))-ylidenemethyl]-amino}-phenyl)-2,2-dimethyl -propionamide;

N-(3-{[2-[1-Cyano-1-((S)-4-isopropyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide;

N-(3-{[2-[1-Cyano-1-((S)-4-methyl-4,5-dihydro-oxazol-2-yl)-meth-(E or Z)-ylidene]-3-ethyl-4-oxo-thiazolidin-( 5-(E/Z))-ylidenemethyl]-amino}-phenyl)-2,2-dimethyl-propionamide;

N-(3-{[2-[1Cyano-1-(3-oxa-1-aza-spiro [4.4]non-1-en-2-yl)-meth-(E or Z)-ylidene]-3-ethyl-4-oxo-thiazolidin-(5-(E/Z))-ylidenemethyl]-amino}-phenyl)-2,2-dimethyl-propionamide;

2-{Cyano-[5-[1-[3-(2,2-dimethyl-propionylamino)-phenylamino]-meth-(E/Z)-ylidene]-3-ethyl-4-oxo-thiazolidin-(2-(E or Z))-ylidene]-methyl}-4,5-dihydro-oxazole-4-carboxylic acid methyl ester;

N-(3-{[2-[Cyano-1-((4R,5R)-4-methyl-5-phenyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl -propionamide;

N-(3-{[2-[1-Cyano-1-((R)-4-phenyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2,2-dimethyl-propionamide;

N-(3-{[2-((S)-4-tert-Butyl-4,5-dihydro-oxazol-2-yl)-1-cyano-meth-(E or Z)-ylidene]-3-ethyl-4-oxo-thiazolidin-(5-(E/Z))-ylidenemethyl]-amino}-phenyl)-2,2-dimethyl-propionamide;

N-(3-{[2-[1-Cyano-1-((R)-4-isobutyl-4,5-dihydro-oxazol-2-yl-meth-(E or Z)-ylidene]-3-ethyl-4-oxo-thiazol-(5-(E/Z))-ylidenemethyl]-amino}-phenyl)-2,2-dimethyl-propionamide;

N-(3-{[2-[1-Cyano-1-[4-(2-methylsulfanyl-ethyl)-4,5-dihydro-oxaol-2-yl]-meth-(E or Z)-ylidene]-3-ethyl-4-oxo-thiazolidin-(5-(E/Z))-ylidenemethyl]-amino}-phenyl)-2,2-dimethy -propionamide;

N-(3-[2-1-((S)-4-Benzyl-4,5-dihydro-oxazol-2-yl)-1-cyano-meth-(E or Z)-ylidene]-3-ethyl-4-oxo-thiazolidin-(5-(E/Z))-ylidenemethyl]-amino}-phenyl)-2,2-dimethyl -propionamide;

N-(3-Chloro-5-{[2-[(3aS,6aR)-1-cyano-1-4,5 ,6,6a-tetrahydro-3aH-cyclopentaoxazol-2-y]-meth-(E or Z)-ylidene]-3-ethyl-4-oxo-thiazolidin-(5-(E/Z))-ylidenemethyl]-amino}-phenyl)-2,2-dimethyl-propionamide;

N-(3-Chloro-5-{[2-[1-cyano-1-(4,4-dimethyl-4,5-dihydro-oxazol-2-yl)-meth-(E or Z)-ylidene]-3-ethyl-4-oxo-thiazolidin-(5-E/Z))-ylidenemethyl]-amino}-phenyl)-2,2-dimethyl-propionamide;

N-(3-{[2-[(3aS,6aR)-1-Cyano-1-4,5,6,6a-tetrahydro-3aH-cyclopentaoxazol-2-yl-meth-(E or Z)-ylidene]-3-ethyl-4-oxo-thiazolidin-(5-(E/Z))-ylidenemethyl]-amino}-phenyl)-2-hydroxy-2-methyl-propionamide;

N-(3-{[2[(3aS ,6aR)-1-Cyano-1-4,5,6,6a-tetrahydro-3aH-cyclopentaoxazol -2-yl-meth-(E or Z)-ylidene]-3-ethyl-4-oxo-thiazolidin-(5-(E/Z))-ylidenemethyl]-amino}-phenyl)-2-(2-methoxy -ethoxy)-acetamide;

N-(3-{[2-[1-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-phenyl)-2-(2-methoxy-ethoxy)-acetamide;

N-(6-{[(2-[(3aS,6aR)-1-Cyano-1-4,5,6,6a-tetrahydro-3aH-cyclopentaoxazol-2-yl-meth-(E or Z)-ylidene]-3-ethyl-4-oxo-thiazolidin-(5-(E/Z))-ylidenemethyl]-amino}-pyridin-2-yl)-2,2-dimethyl -propionamide;

N-(6-{[2-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-pyridin-2-yl)-2,2-dimethyl-propionamide;

N-(6-{[2-[(3aS,6aR)-1-Cyano-1-4,5,6,6a-tetrahydro-3aH-cyclopentaoxazol-2-yl-meth-(E or Z)-ylidene]-3-ethyl-4-oxo-thiazolidin-(5-(E/Z))-ylidenemethyl]-amino}-pyridin-2-yl)-2-(2-methoxy -ethoxy)-acetamide;

N-(6-{[2-[1-Cyano-1-(4,4-dimethyl-4,5-dihydro-oxazol-2-yl)-meth-(E or Z)-ylidene]-3-ethyl-4-oxo-thiazolidin-(5-(E/Z))-ylidenemethyl]-amino}-pyridin-2-yl)-2-(2-methoxy-ethoxy)-acetamide;

[3-Ethyl-5-[1-(2-ethylamino-pyridin-4-ylamino)-meth-(E/Z)-ylidene]-4-oxo-thiazolidin-(2-(E or Z))-ylidene]-(3 aS ,6aR)-4 ,5 ,6,6a-tetrahydro-3aH-cyclopentaoxazol-2-yl-acetonitrile;

(4,4-Dimethyl-4,5-dihydro-oxazol-2-yl)-[3-ethyl-5-[1-(2-ethylamino-pyridin-4-ylamino)-meth -(E/Z)-ylidene]-4-oxo-thiazolidin-(2-(E or Z))-ylidene]-acetonitrile;

(4,4-Dimethyl-4,5-dihydro-oxazol-2-yl)-1-ethyl-5-[1-{3-[(4aR,8aS)-2-(decahydro-isoquinohn -2-yl)-ethyl]-phenylamino}-meth-(E/Z)-ylidene]-4-oxo-thiazolidin-(2-(E or Z))-ylidene]-acetonitrile;

2-{Cyano-[5-[1-[3-(2,2-dimethyl-propionylamino)-phenylamino]-meth-(E/Z)-ylidene ]-3-ethyl-4-oxo-thiazolidin-(2-(E or Z))-ylidene]-methyl}-oxazole-4-carboxylicacid methyl ester;

N-(3-{[2-[1-Cyano-1-(3-methyl-[1,2,4]oxadiazol-5-yl)-meth-(E or Z)-ylidene]-3-ethyl-4-oxo-thiazolidin-(5-(E/Z))-ylidenemethyl]-amino}-phenyl)-2,2-dimethyl-propionamide;

[3-Ethyl-4-oxo-5-[1-phenylamino-meth-(E/Z)-ylidene]-thiazolidin-(2-(E or Z))-ylidene]-(3-methyl-[1,2,4]oxadiazol-5-yl)-acetonitrile;

N-(3-{[2-[1-Cyano-1-(3-methyl-[1,2,4]oxadiazol-5-yl)-meth-(E or Z)-ylidene]-3-ethyl-4-oxo -thiazolidin-(5-(E/Z))-ylidenemethyl]-amino}-phenyl)-2-(2-methoxy-ethoxy)-acetamide;

[3-Ethyl-4-oxo-5-[1-phenylamino-meth-(E/Z)-ylidene]-thiazolidin-(2-(E or Z))-ylidenel-pyridin -2-yl-acetonitrile;

[3-Ethyl-4-oxo-5-[1-phenylamino-meth-(E/Z)-ylidene]-thiazolidin-(2-(E or Z))-ylidene]-pyridin -3-yl-acetonitrile;

[3-Ethyl-4-oxo-5-[1-phenylamino-meth-(E/Z)-ylidene]-thiazolidin-(2-(E or Z))-ylidene]-pyridin -4-yl-acetonitrile;

3-Ethyl-4-oxo-5-[1-phenylamino-meth-(E/Z)-ylidene]-thiazlidin-(2-(E or Z))-ylidene]-thiophen -2-yl-acetonltdle;

[3-Ethyl-4-oxo-5-[1-phenylamino-meth-(E/Z)-ylidene]-thiazolidin-(2-(E or Z))-ylidene]-thiophen-3-yl-acetonitrile;

Benzo[b]thiophen-3-yl-[3-ethyl-4-oxo-5-[1-phenylamino-meth-(E/Z)-ylidene]-thiazolidin-(2-(E or Z))-ylidene]-acetonitrile;

[3-Ethyl-4-oxo-5-[1-phenylamino-meth-(E/Z)-ylidene]-thiazolidin-(2-(E or Z))-ylidene](1-methyl-1H-benzoimidazol-2-yl)-acetonitrile;

Benzothiazol-2-yl-[3-ethyl-4-oxo-5-[1-phenylamino-meth-(E/Z)-ylidene]-thiazolidin-(2-QB or Z))-ylidene]-acetonitile;

[3-Ethyl-4-oxo-5-[1-phenylamino-meth-(E/Z)-ylidenel-thiazolidin-(2-(E or Z))-ylidene]-(4-methyl-tiazol-2-yl)-acetonitrile; or

[3-Ethyl-4-oxo-5-[1-phenylamino-meth-(E or Z)-ylidene]-thiazolidin-(2-(E or Z))-ylidene]-(1-methyl-1H-pyrrol-2-yl)-acetonitrile.

12. A compound according to claim 1, which is

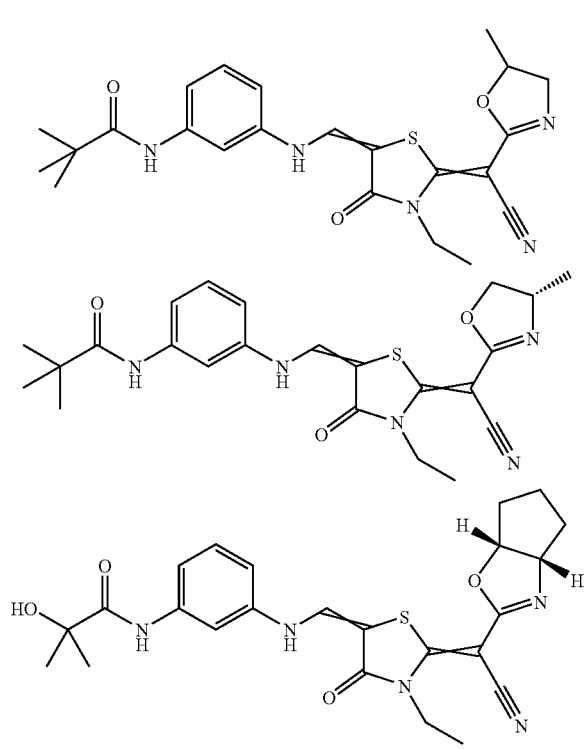

-continued

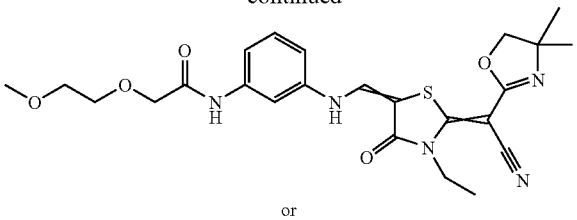

or

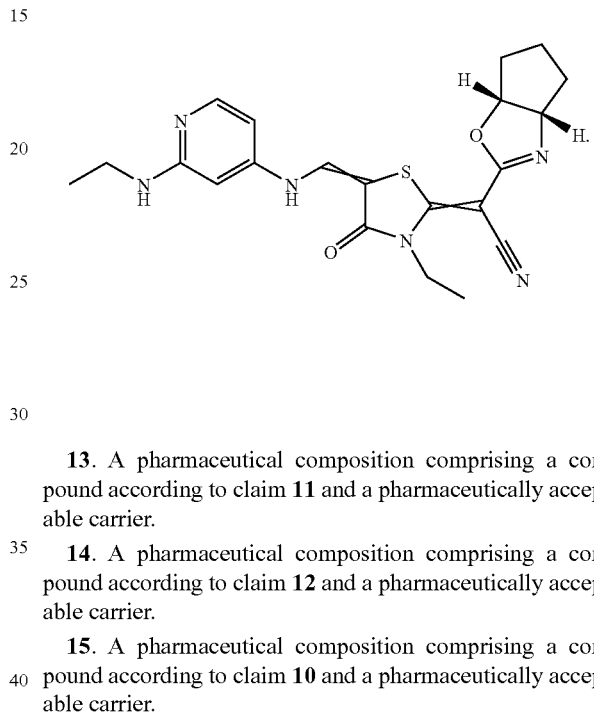

13. A pharmaceutical composition comprising a compound according to claim 11 and a pharmaceutically acceptable carrier.

14. A pharmaceutical composition comprising a compound according to claim 12 and a pharmaceutically acceptable carrier.

15. A pharmaceutical composition comprising a compound according to claim 10 and a pharmaceutically acceptable carrier.

* * * * *

UNITED STATES PATENT AND TRADEMARK OFFICE
CERTIFICATE OF CORRECTION

PATENT NO. : 7,511,059 B2
APPLICATION NO. : 11/345666
DATED : March 31, 2009
INVENTOR(S) : Volker Schulze et al.

It is certified that error appears in the above-identified patent and that said Letters Patent is hereby corrected as shown below:

On Title page Item (73) Assignee: "Schering Ag" should read --Bayer Schering Pharma Aktiengesellschaft--.

Signed and Sealed this

First Day of June, 2010

David J. Kappos
*Director of the United States Patent and Trademark Office*

UNITED STATES PATENT AND TRADEMARK OFFICE
CERTIFICATE OF CORRECTION

PATENT NO.        : 7,511,059 B2
APPLICATION NO.   : 11/345666
DATED             : March 31, 2009
INVENTOR(S)       : Schulze et al.

It is certified that error appears in the above-identified patent and that said Letters Patent is hereby corrected as shown below:

Column 146, line 27 reads "halogen, hydroxy, C2326-heterocycloalkyl, $C_1$-$C_6$-hy-" should read
-- halogen, hydroxy, $C_{2-6}$-heterocycloalkyl, $C_1$-$C_6$-hy- --

Column 146, line 61 reads "thiomorphol inyl, tetrahydroisoquinol inyl or decahy-" should read
-- thiomorpholinyl, tetrahydroisoquinolinyl or decahy --

Column 147, line 4 reads "inyl, piperazinyl, morphol inyl, thiomorpholinyl or" should read
-- inyl, piperazinyl, morpholinyl, thiomorpholinyl or --

Column 147, line 32 reads "thiomorphol inyl, tetrahydroisoquinol inyl or decahy-" should read
-- thiomorpholinyl, tetrahydroisoquinolinyl or decahy- --

Column 147, line 62 reads "$R^2$ and $R^2$, independently of one another, stand for hydro-" should read
-- $R^3$ and $R^4$, independently of one another, stand for hydro- --

Column 148, line 22 reads "cloalkyl or with the group -NR $3R^4$ or -CO($NR^3$)-" should read
-- cloalkyl or with the group -$NR^3$ $R^4$ or -CO($NR^3$)- --

Column 149, line 42 reads "same way or differently, with cyano, halogen, $C_1$-$C_1$-" should read
-- same way or differently, with cyano, halogen, $C_1$-$C_6$- --

Column 150, line 26 reads "3-{[2-[1-Cyano-1-(4,5-dihydro-oxazo-2-yl)-meth-(E or" should read
-- 3-{[2-[1-Cyano-1-(4,5-dihydro-oxazol-2-yl)-meth-(E or --

Column 150, line 39 reads "3-{[2-[1-Cyano-1-(4,4-dimethyl - 4,5-dihydro-oxazo 1-2-" should read
-- 3-{[2-[1-Cyano-1-(4,4-dimethyl - 4,5-dihydro-oxazol-2- --

Column 150, line 42 reads "yl-propyl)-benzmnide;" should read -- yl-propyl)benzamide; --

Signed and Sealed this
Second Day of October, 2012

David J. Kappos
*Director of the United States Patent and Trademark Office*

CERTIFICATE OF CORRECTION (continued)

U.S. Pat. No. 7,511,059 B2

Column 150, line 47 reads "3-{[2-[1-Cyano-1-((R)-4-ethyl-4,5-dihydro-oxazol-2-yl)-" should read
-- 3-{[2-[1-Cyano-1-((R)-4-phenyl-4,5-dihydro-oxazol-2-yl)- --

Column 150, line 59 reads "dimethyl-propionainide;" should read
-- dimethyl-propionamide; --

Column 150, line 61 reads "3aH-cycopentaoxazol]-2-yl-meth-(E or Z)-ylidene]-3-" should read
-- 3aH-cycopentaoxazol-2-yl-meth-(E or Z)-ylidene]-3- --

Column 151, line 1 reads "N-(3-{[2-[1-Cyano-1-((S)-4-ethyl-4,5-dihydro-oxazo-2-" should read
-- N-(3-{[2-[1-Cyano-1-((S)-4-ethyl-4,5-dihydro-oxazol-2- --

Column 151, line 29 reads "N-(3-{[2-[Cyano-1-((4R,5R)-4-methyl-5-phenyl-4,5-di-" should read
-- N-(3-{[2-1-Cyano-1-((4R,5R)-4-methyl-5-phenyl-4,5-di- --

Column 151, line 42 reads "azol-2-yl-meth-(E or Z)-ylidene]-3-ethyl-4-oxo-thia-" should read
-- azol-2-yl)-meth-(E or Z)-ylidene]-3-ethyl-4-oxo-thia- --

Column 151, line 43 reads "zol-(5-(E/Z))-ylidenemethyl]-amino}-phenyl)-2,2-" should read
-- zolidin-(5-(E/Z))-ylidenemethyl]-amino}-phenyl)-2,2- --

Column 151, line 46 reads "hydro-oxao1-2-yl]-meth-(E or Z)-ylidene]-3-ethyl-4-" should read
-- hydro-oxazol-2-yl]-meth-(E or Z)-ylidene]-3-ethyl-4- --

Column 151, line 48 reads "nyl)-2,2-dimethy - propionamide;" should read
-- nyl)-2,2-dimethyl - propionamide; --

Column 151, line 49 reads "N-(3-[2-1-((S)-4-Benzyl-4,5-dihydro-oxazol-2-yl)-1-cy-" should read
-- N-(3-{[2-1-((S)-4-Benzyl-4,5-dihydro-oxazol-2-yl)-1-cy- --

Column 151, line 50 reads "ano-meth-(E or Z)-yidene]-3-ethyl-4-oxo-thiazolidin-" should read
-- ano-meth-(E or Z)-ylidene]-3-ethyl-4-oxo-thiazolidin- --

Column 151, line 54 reads "rahydro-3aH-cyclopentaoxazol-2-y]-meth-(E or" should read
-- rahydro-3aH-cyclopentaoxazol-2-yl-meth-(E or --

Column 152, line 11 reads "N-(6-{[2-Cyano-1-(4,4-dimethyl-4,5-dihydro-oxazol-2-" should read
-- N-(6-{[2-[1-Cyano-1-(4,4-dimethyl-4,5-dihydro-oxazol-2- --

Column 152, line 31 reads "(4,4-Dimethyl-4,5-dihydro-oxazol-2-yl)-1-ethyl-5-[1-{3-" should read
-- (4,4-Dimethyl-4,5-dihydro-oxazol-2-yl)-[3-ethyl-5-[1-{3- --

Column 152, line 34 reads "(2-(E or Z))-ylidene1]-acetonitrile;" should read
-- (2-(E or Z))-ylidene]-acetonitrile; --

CERTIFICATE OF CORRECTION (continued)
U.S. Pat. No. 7,511,059 B2

Column 152, line 38 reads "boxylicacid methyl ester;" should read -- boxylic acid methyl ester; --

Column 152, line 51 reads "thiazolidin-(2-(E or Z))-ylidene1-pyridin -2-yl-acetoni-" should read -- thiazolidin-(2-(E or Z))-ylidene]-pyridin -2-yl-acetoni- --

Column 152, line 61 reads "1td1e;" should read -- itrile; --

Column 153, line 2 reads "thiazolidin-(2-(E or Z))-ylidene](1-methyl-1H-ben-" should read -- thiazolidin-(2-(E or Z))-ylidene]-(1-methyl-1H-ben- --

Column 153, line 5 reads "meth-(E/Z)-ylidene]-thiazolidin-(2-QB or Z))-ylidene]-" should read -- meth-(E/Z)-ylidene]-thiazolidin-(2-E or Z))-ylidene]- --

Column 153, line 10 reads "[3-Ethyl-4-oxo-5-[1-phenylamino-meth-(E or" should read -- [3-Ethyl-4-oxo-5-[1-phenylamino-meth-(E/Z) or --

Column 153, line 11 reads "Z)-ylidene]-thiazolidin-(2-(E or Z))-ylidene]-(1-me-" should read -- -ylidene]-thiazolidin-(2-(E or Z))-ylidene]-(1-me- --